(12) United States Patent
Mao et al.

(10) Patent No.: US 10,053,484 B2
(45) Date of Patent: *Aug. 21, 2018

(54) HETEROCYCLE-SUBSTITUTED XANTHENE DYES

(71) Applicant: Biotium, Inc., Fremont, CA (US)

(72) Inventors: Fei Mao, Fremont, CA (US); Wai-Yee Leung, San Ramon, CA (US); Ching-Ying Cheung, San Ramon, CA (US); Hye Eun Hoover, Alameda, CA (US)

(73) Assignee: Biotium, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/375,649

(22) Filed: Dec. 12, 2016

(65) Prior Publication Data

US 2017/0247402 A1   Aug. 31, 2017

Related U.S. Application Data

(63) Continuation of application No. 12/850,578, filed on Aug. 4, 2010, now Pat. No. 9,579,402.

(60) Provisional application No. 61/266,955, filed on Dec. 4, 2009.

(51) Int. Cl.
| | |
|---|---|
| *C07H 15/26* | (2006.01) |
| *C07D 405/04* | (2006.01) |
| *C07D 405/14* | (2006.01) |
| *C07D 491/14* | (2006.01) |
| *C07D 491/147* | (2006.01) |
| *C07K 1/13* | (2006.01) |
| *C07K 16/00* | (2006.01) |
| *C07D 491/22* | (2006.01) |
| *C07F 9/6558* | (2006.01) |

(52) U.S. Cl.
CPC .......... *C07H 15/26* (2013.01); *C07D 405/04* (2013.01); *C07D 405/14* (2013.01); *C07D 491/147* (2013.01); *C07D 491/22* (2013.01); *C07F 9/65586* (2013.01); *C07K 1/13* (2013.01); *C07K 16/00* (2013.01)

(58) Field of Classification Search
CPC .... C07H 15/16; C07D 405/04; C07D 405/14; C07D 491/14; C07D 491/147; C07F 9/65586; C07K 1/13; C07K 16/00
See application file for complete search history.

(56) References Cited

U.S. PATENT DOCUMENTS

| | | | |
|---|---|---|---|
| 4,520,110 A | 5/1985 | Stryer et al. | |
| 4,683,195 A | 7/1987 | Mullis et al. | |
| 4,683,202 A | 7/1987 | Mullis | |
| 4,711,955 A | 12/1987 | Ward et al. | |
| 4,731,433 A | 3/1988 | Yatsu et al. | |
| 4,889,818 A | 12/1989 | Gelfand et al. | |
| 5,047,519 A | 9/1991 | Hobbs, Jr. et al. | |
| 5,338,671 A | 8/1994 | Scalice et al. | |
| 5,366,860 A | 11/1994 | Bergot et al. | |
| 5,494,810 A | 2/1996 | Barany et al. | |
| 5,623,080 A | 4/1997 | Neckers et al. | |
| 5,714,327 A | 2/1998 | Houthoff et al. | |
| 5,714,386 A | 2/1998 | Roederer | |
| 5,750,409 A | 5/1998 | Herrmann et al. | |
| 5,773,258 A | 6/1998 | Birch et al. | |
| 5,792,389 A | 8/1998 | Hammond et al. | |
| 5,824,477 A | 10/1998 | Stanley | |
| 5,871,928 A | 2/1999 | Fodor et al. | |
| 6,008,379 A | 12/1999 | Benson et al. | |
| 6,033,850 A | 3/2000 | Purvis | |
| 6,040,193 A | 3/2000 | Winkler et al. | |
| 6,130,101 A | 10/2000 | Mao et al. | |
| 6,162,931 A | 12/2000 | Gee et al. | |
| 6,262,776 B1 | 7/2001 | Griffis | |
| 6,291,203 B1 | 9/2001 | Poot et al. | |
| 6,403,320 B1 | 6/2002 | Read et al. | |
| 6,479,303 B1 | 11/2002 | Waggoner et al. | |
| 6,576,424 B2 | 6/2003 | Fodor et al. | |
| 6,917,726 B2 | 7/2005 | Levene et al. | |
| 6,974,873 B2 | 12/2005 | Leung et al. | |
| 7,013,054 B2 | 3/2006 | Levene et al. | |
| 7,170,050 B2 | 1/2007 | Turner et al. | |
| 7,181,122 B1 | 2/2007 | Levene et al. | |
| 7,267,673 B2 | 9/2007 | Pilcher et al. | |
| 7,292,742 B2 | 11/2007 | Levene et al. | |

(Continued)

FOREIGN PATENT DOCUMENTS

| | | |
|---|---|---|
| WO | WO-0013026 A1 | 3/2000 |
| WO | WO-2004065548 A2 | 8/2004 |

(Continued)

OTHER PUBLICATIONS

Momse et al., 3 Pharm. Bull. 321-2 (1955) (CAS Abstr.) (Year: 1955).*

Cai et al. Design and synthesis of rhodamine 110 derivative and caspase-3 substrate for enzyme and cell-based fluorescent assay. Bioorg Med Chem Lett. Jan. 8, 2001;11(1):39-42.

Gannon, et al. Rhodamine inhibitors of P-glycoprotein: an amide/thioamide "switch" for ATPase activity. Journal of medicinal chemistry 52.10 (2009): 3328-3341.

(Continued)

*Primary Examiner* — Timothy R Rozof

(74) *Attorney, Agent, or Firm* — Wison, Sonsini, Goodrich & Rosati

(57) ABSTRACT

The present invention relates to fluorescent dyes in general. The present invention provides a wide range of fluorescent dyes and kits containing the same, which are applicable for labeling a variety of biomolecules, cells and microorganisms. The present invention also provides various methods of using the fluorescent dyes for research and development, forensic identification, environmental studies, diagnosis, prognosis, and/or treatment of disease conditions.

17 Claims, 12 Drawing Sheets

(56) References Cited

U.S. PATENT DOCUMENTS

| | | | |
|---|---|---|---|
| 7,367,994 | B2 | 5/2008 | Lagrange |
| 8,436,170 | B2 | 5/2013 | Mao et al. |
| 8,709,830 | B2 | 4/2014 | Mao et al. |
| 9,006,437 | B2 | 4/2015 | Mao et al. |
| 9,097,667 | B2 | 8/2015 | Mao et al. |
| 9,579,402 | B2 | 2/2017 | Mao et al. |
| 2004/0242902 | A1 | 12/2004 | Lam et al. |
| 2005/0112781 | A1 | 5/2005 | Lee et al. |
| 2005/0272053 | A1 | 12/2005 | Mao et al. |
| 2006/0019274 | A1 | 1/2006 | Goel |
| 2006/0179585 | A1 | 8/2006 | Zilles et al. |
| 2006/0211028 | A1 | 9/2006 | Mao et al. |
| 2006/0211029 | A1 | 9/2006 | Mao et al. |
| 2008/0044805 | A1 | 2/2008 | Whitten et al. |
| 2008/0177086 | A1 | 7/2008 | Frank et al. |
| 2009/0192298 | A1 | 7/2009 | Burgess |
| 2009/0227467 | A1* | 9/2009 | Chang ............... G01N 33/5061 506/9 |
| 2010/0009454 | A1 | 1/2010 | Mao et al. |
| 2010/0197030 | A1 | 8/2010 | Mao et al. |
| 2010/0317016 | A1 | 12/2010 | Mao et al. |
| 2010/0323453 | A1 | 12/2010 | Mao et al. |
| 2011/0136201 | A1 | 6/2011 | Mao et al. |
| 2014/0011208 | A1 | 1/2014 | Mao et al. |

FOREIGN PATENT DOCUMENTS

| | | | |
|---|---|---|---|
| WO | WO-2005003086 | A2 | 1/2005 |
| WO | WO-2004065548 | A3 | 4/2005 |
| WO | WO-2005003086 | A3 | 2/2006 |

OTHER PUBLICATIONS

Balakrishanan, et al. Chemical modification of poly(vinyl chloride) resin using poly(ethylene glycol) to improve blood compatibility. Biomaterials. 2005;26(17):3495-502.

Boyarski, et al. Photostable, amino reactive and water-soluble fluorescent labels based on sulfonated rhodamine with a rigidized xanthene fragment. Chemistry. 2008;14(6):1784-92.

Brinkley, et al. A brief survey of methods for preparing protein conjugates with dyes, haptens, and cross-linking reagents. Bioconjug Chem. Jan.-Feb. 1992;3(1):2-13.

Browne, et al. Emerging Technologies. BioProbes. Mar. 2007;52:2-11.

Cha, et al. Rhodamine-labeled 2beta-carbomethoxy-3beta-(3,4-dichlorophenyl)tropane analogues as high-affinity fluorescent probes for the dopamine transporter. J Med Chem. Dec. 1, 2005;48(24):7513-6.

David, et al. Synthesis of fluorescent rhodamine dyes using an extension of the Heck reaction. Neurology. Tetrahedron Letters. Mar. 10, 2008;49(11):1860-1864.

De Mesmaeker, et al. Backbone modifications for antisense oligonucleotides. Pure & Appl. Chem. 1997;69(3):437-440.

European search report and search opinion dated Apr. 5, 2013 for EP Application No. 10834885.5.

European search report dated Aug. 22, 2012 for EP Application No. 10739088.2.

Fried, et al. Equilibria and kinetics of lac repressor-operator interactions by polyacrylamide gel electrophoresis. Nucleic Acids Res. 1981;9(23):6505-25.

Garner, et al. A gel electrophoresis method for quantifying the binding of proteins to specific DNA regions: application to components of the Escherichia coli lactose operon regulatory system. Nucleic Acids Research. 1981;9(13):3047-60.

Giaid, et al. Non-isotopic RNA probes. Comparison between different labels and detection systems. Histochemistry. 1989;93(2):191-6.

Gunzenhauser, et al. Halochromic molecules. Synthesis and acidobasic behavior of substituted 3', 6'-bis(dimethylamino)-spiro[5H-imidazo[2,1-a]isoindolin-5,9'-xanthenes]. Helvetica Chimica Acta. 1979; 62(1):171-84. English abstract only.

Haugland, et al. Antibody Conjugates for Cell Biology. Current Protocols in Cell Biology. 2000;16.5.1-16.5.22.

Haugland, et al. Coupling of monoclonal antibodies with biotin. Charter 23. Meth. Mol. Biol. 1995; 45:223-233.

Haugland, R. P. Coupling of monoclonal antibodies with enzymes. Meth. Mol. Biol. 1995; 45:235-243.

Haugland, R. P. Coupling of monoclonal antibodies with fluorophores. Chapter 22. Meth. Mol. Biol. 1995; 45:205-221.

Holland, et al. Detection of Specific Polymerase Chain Reaction Product by Utilizing the 5' → 3' Exonuclease Activity of Thermus Aquaticus DNA Polymerase. Proc. Natl. Acad. Sci. USA, vol. 88, Aug. 1991, pp. 7276-7280.

International search report and written opinion dated Jan. 28, 2011 for PCT Application No. US10/44474.

International search report dated Mar. 29, 2010 for PCT Application No. US2010/23111.

Kulbersh, et al. Sensitivity and specificity of fluorescent immunoguided neoplasm detection in head and neck cancer xenografts. Arch Otolaryngol Head Neck Surg. May 2007;133(5):511-5.

Lee, et al. Allelic Discrimination by Nick-Translation PCR with Fluorogenic Probes. Nucleic Acids Research, vol. 21, No. 16, 1993, pp. 3761-3766.

Lefevre, et al. Texas Res-X and rhodamine Red-X, new derivatives of sulforhodamine 101 and lissamine rhodamine B with improved labeling and fluorescence properties. Bioconjug Chem. Jul.-Aug. 1996;7(4):482-9.

Liu, et al. Rational design and synthesis of a novel class of highly fluorescent rhodamine dyes that have strong absorption at long wavelengths. Tetrahedron Letters. Jun. 2, 2003;44(23):4355-4359.

Mann, et al. Optimizing the photocurrent efficiency of dye-sensitized solar cells through the controlled aggregation of chalcogenoxanthylium dyes on nanocrystalline titania films. The Journal of Physical Chemistry C 112.34 (2008): 13057-13061.

Matscheke, et al. 4H-Imidazoles as functional dyes: synthesis of bichromophores and extension of the merocyanine system. Tetrahedron. 2008;64:7815-7821.

Mehvar, R. Modulation of the pharmacokinetics and pharmacodynamics of proteins by polyethylene glycol conjugation. J. Pharm Pharm Sci. 2000;3(1):125-36.

Mendez, et al. Protein-primed DNA replication: a transition between two modes of priming by a unique DNA polymerase. EMBO Journal. 1997;16(9):2519-27.

Muhlegger, et al. Non-radioactive labeling and detection of nucleic acids. IV. Synthesis and properties of digoxigenin-modified 2'-deoxyuridine-5'-triphosphates and a photoactivatable analog of digoxigenin (photodigoxigenin). Biol. Chem. Hoppe Seyler, 1990;371(10):953-65.

Nimmakayalu, et al. Simple method for preparation of fluor/hapten-labeled dUTP. Biotechniques. 2000;28(3):518-22.

Yang, et al. Scalable synthesis of lissamine rhoadmine B sulfonyl chloride and incorporation of xanthene derivatives onto polymer supports. Synthesis. 2008; 6:957-961.

Zijderveld, et al. Helix-destabilizing properties of the adenovirus DNA-binding protein. J. Virology. 1994;68(2):1158-64.

Notice of Allowance dated Oct. 20, 2016 for U.S. Appl. No. 12/850,578.

Office action dated Apr. 24, 2014 for U.S. Appl. No. 13/859,627.
Office action dated Jun. 17, 2016 for U.S. Appl. No. 12/850,578.
Office action dated Aug. 9, 2012 for U.S. Appl. No. 12/699,778.
Office action dated Nov. 13, 2015 for U.S. Appl. No. 12/850,578.

Sambrook, et al. T. Molecular Cloning: a laboratory manual. 2nd ed. N. Y., Cold Spring Harbor Laboratory, Cold Spring Harbor Laboratory Press, 1989. (Table of Contents only).

Sauer, et al. New fluorescent dyes in the red region for biodiagnostics. Journal of Fluorescence. 1995;5(3):247-261.

Shandura, et al. New heterocyclic analogues of rhodamines. Dyes and Pigments. 2007;73:25-30.

Skaliter, et al. Rolling circle DNA replication in vitro by a complex of herpes simplex virus type 1-encoded enzymes. Proc. Natl, Acad. Sci. USA. 1994;91(22):10665-9.

(56) References Cited

OTHER PUBLICATIONS

Tombline, et al. Stimulation of P-glycoprotein ATPase by analogues of tetramethylrosamine: coupling of drug binding at the "R" site to the ATP hydrolysis transition state. Biochemistry 45.26 (2006): 8034-8047.
Tsurumi, et al. Functional interaction between Epstein-Barr virus DNA polymerase catalytic subunit and its accessory subunit in vitro. J. Virology.1993;67(12):7648-53.
Veiseh, et al. Tumor paint: a chlorotoxin:Cy5.5 bioconjugate for intraoperative visualization of cancer foci. Cancer Res. Jul. 15, 2007;67(14):6882-8.
von Sigmund Gunzenhauser et al. Helvetica Chimica Acta—vol. 62, Fasc. 1 (1979)—Nr. 25 (STN results).

* cited by examiner

AlexaFluor633  Compound No. 6

Mitochondrial Staining

Compound No. 16  Compound No. 74

HETEROCYCLE-SUBSTITUTED XANTHENE DYES

CROSS-REFERENCE

This application is a continuation application of U.S. application Ser. No. 12/850,578, filed Aug. 4, 2010, now U.S. Pat. No. 9,579,402, which application claims the benefit of U.S. Provisional Application No. 61/266,955, filed Dec. 4, 2009, which applications are incorporated herein by reference in their entirety and for all purposes.

BACKGROUND OF THE INVENTION

Fluorescent dyes are widely used in biological research and medical diagnostics. Fluorescent dyes are superior to conventional radioactive materials because fluorescent dyes are less expensive and less toxic, and can typically be detected with sufficient sensitivity. In particular, a diversity of fluorophores with a distinguishable color range has made it more practical to perform multiplexed assays capable of detecting multiple biological targets at the same time. The ability to visualize multiple targets in parallel is often required for delineating the spatial and temporal relationships amongst different biological targets in vitro and in vivo. In addition, the generation of a wide range of fluorescent dyes has opened a new avenue for conducting high-throughput and automated assays, thus dramatically reducing the unit cost per assay. Moreover, the low toxicity of fluorescent dyes provides ease of handling in vitro, and also renders it safer for imaging biological activities in vivo.

Among the different classes of fluorescent dyes developed as labels for lifescience applications, fluorescein and rhodamine dyes (collectively called xanthene dyes) have been used for labeling nucleic acids, antibodies and various other biomolecules. For example, fluorescein type dyes, such as FAM, JOE, HEX and NED are used for preparing real-time PCR probes, or so-called TaqMan probes (Holland et al., Proc. Natl. Acad. Sci. USA 88, 7276(1991); Lee et al., Nucleic Acids Res. 21, 3761(1993). Likewise, various rhodamine dyes have been used for preparing real-time PCR probes based on oligonucleotides homo-doubly labeled with two identical dyes (Mao, et al., US patent application No. 20050272053). Fluorescently labeled antibodies are important tools in fluorescence immunochemistry-based detections, and fluorescein and rhodamine dyes were among the first dyes used for preparing antibody conjugates. However, many of these xanthenes dyes suffer from problems of fluorescence quenching and poor water solubility.

Xanthene dyes which absorb and emit in a variety of colors are also useful for biological applications. Xanthene dyes with short wavelength absorption/emission include, for example, fluorescein and rhodamine 110 and sulfonated rhodamine 110. Xanthenes dyes with longer wavelength absorption/emission profile include the fluorescein derivative JOE, which has a methoxy substituent at the 4 and 5-positions, respectively, has absorption/emission maxima at 520/548 nm, compared to the parent dye fluorescein (or FAM), which has absorption/emission at 495/520 nm. The rhodamine dye ROX has absorption/emission at 575/602 nm, compared to the parent rhodamine dye carboxy-rhodamine 110, which absorbs and emits at 502/524 nm. Additional dyes are described by Sauer, et al. Journal of Fluorescence 5(3), 247 (1995), David, et al. Tetrahedron Letters 49(11), 1860 (2008) and Liu, et al. Tetrahedron Letters 44, 4355(2003).

SUMMARY OF THE INVENTION

Further improvement in the properties of the dyes is needed in order to meet the increasing demands of new instruments and new biological applications. Specifically, additional strategies are necessary to allow fine-tuning of the wavelengths of the dyes for maximal signal detection and for providing additional colors currently unattainable using known synthetic methods. Moreover, it is desirable to provide new xanthenes dyes that offer a combination of optimal wavelengths for instrument compatibility and improved brightness, photostability and water-solubility for labeling biomolecules. The present invention addresses this need and provides additional advantages.

In one aspect, the invention provides compounds of Formula 1a or 1b:

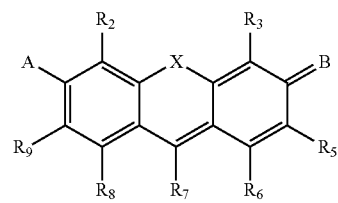

Formula 1a

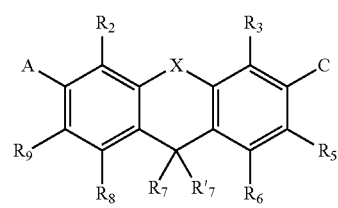

Formula 1b wherein:
X is O, S, or —C(CH$_3$)$_2$—;
A is —OR$_1$ or —NR$_1$R$_{1a}$;
B is =O or =N$^+$R$_4$R$_{4a}$;
C is —OR$_4$ or —NR$_4$R$_{4a}$;
R$_1$, R$_{1a}$, R$_4$, and R$_{4a}$ are each independently H or alkyl, unsubstituted or substituted with -L -SO$_3^-$, -L-PO$_3^{2-}$, a water-soluble polymer, or with -L-R$_x$; or one or more pair of R$_1$ and R$_{1a}$ or R$_4$ and R$_{4a}$ together with the nitrogen to which they are attached form a saturated or unsaturated ring optionally substituted by any of -L-SO$_3^-$, -L-PO$_3^{2-}$ and -L-R$_x$; or at least one of R$_1$, R$_{1a}$, R$_4$, or R$_{4a}$ is an enzyme substrate or a protecting group;
R$_7$ is:

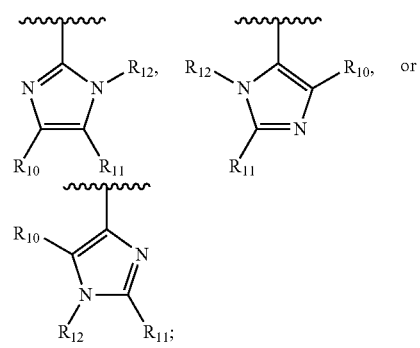

R'$_7$ is H, OH, CN, or C$_1$-C$_6$ alkoxy; or R'$_7$ in combination with R$_7$ forms a 5- or 6-membered spirolactone or spirosultone ring;

R$_2$, R$_3$, R$_5$, R$_6$, R$_8$, R$_9$, R$_{10}$, R$_{11}$, and R$_{12}$ are each independently H, halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, -L-R$_x$; and when R$_7$ is

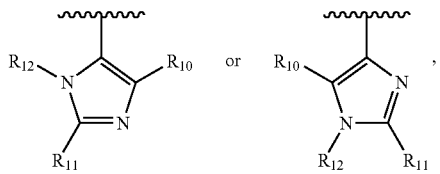

R$_{10}$ is optionally CO$_2^-$; or one or more pair of R$_2$ and R$_{1a}$, R$_3$ and R$_{4a}$, R$_4$ and R$_5$, R$_5$ and R$_6$, R$_8$ and R$_9$, R$_9$ and R$_1$, R$_{10}$ and R$_{11}$, or R$_{11}$ and R$_{12}$ together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$;

R$_x$ is a reactive group;

L is a bond or (Q)$_n$;

each Q is independently NR$_d$, S(O)$_t$, O, C(=X), (C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two NR$_d$ are adjacent and no two O are adjacent;

n is 1-20; and each R$_d$ is H, substituted or unsubstituted alkyl.

In some embodiments, X is O. In other embodiments, A is —NR$_1$R$_{1a}$ and B is =N$^+$R$_4$R$_{4a}$. For example, A is —NR$_1$R$_{1a}$, B is =N$^+$R$_4$R$_{4a}$, and at least one pair of R$_1$ and R$_9$, or R$_4$ and R$_5$ taken together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$.

For example, said at least one ring is substituted by -L-PO$_3^{2-}$ or -L-SO$_3^-$. Alternatively, said at least one ring is substituted by at least one alkyl. In another embodiment, at least one of R$_2$ and R$_3$ is -L-SO$^{3-}$.

In some embodiments, R$_7$ is

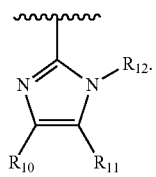

For example, R$_{10}$ and R$_{11}$ are H. Alternatively, R$_{10}$ and R$_{11}$ taken together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$. In another embodiment, R$_{12}$ is -L-R$_x$.

The invention also provides compounds of Formula 1a or 1b:

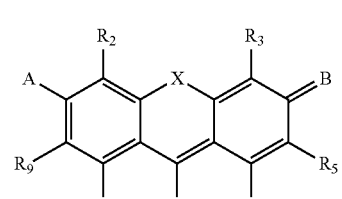

Formula 1a

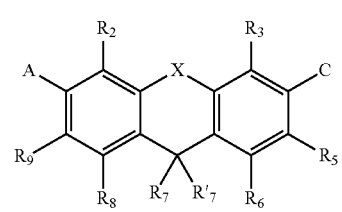

Formula 1b wherein:
X is O, S, or —C(CH$_3$)$_2$—;
A is —OR$_1$ or —NR$_1$R$_{1a}$;
B is =O or =N$^+$R$_4$R$_{4a}$;
C is —OR$_4$ or —NR$_4$R$_{4a}$;
R$_1$, R$_{1a}$, R$_4$, and R$_{4a}$ are each independently H or alkyl, unsubstituted or substituted with -L-SO$_3^-$, -L-PO$_3^{2-}$, a water-soluble polymer, or with -L-R$_x$; or one or more pair of R$_1$ and R$_{1a}$ or R$_4$ and R$_{4a}$ together with the nitrogen to which they are attached form a saturated or unsaturated ring optionally substituted by any of -L-SO$_3^-$, -L-PO$_3^{2-}$ and -L-R$_x$; or at least one of R$_1$, R$_{1a}$, R$_4$, or R$_{4a}$ is an enzyme substrate or a protecting group;
R$_7$ is:

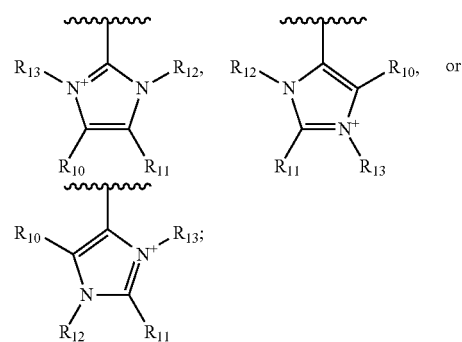

R'$_7$ is H, OH, CN, or C$_1$-C$_6$ alkoxy; or R'$_7$ in combination with R$_7$ forms a 5- or 6-membered spirolactone or spirosultone ring;

R$_2$, R$_3$, R$_5$, R$_6$, R$_8$, R$_9$, R$_{11}$, R$_{12}$ and R$_{13}$ are each independently H, halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$; and when R$_7$ is

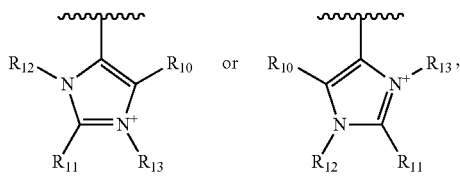

R$_{10}$ is optionally CO$_2^-$; or one or more pair of R$_2$ and R$_{1a}$, R$_3$ and R$_{4a}$, R$_4$ and R$_5$, R$_5$ and R$_6$, R$_8$ and R$_9$, R$_9$ and R$_1$, R$_{10}$ and R$_{11}$, R$_{11}$ and R$_{12}$, R$_{11}$ and R$_{13}$, R$_{10}$ and R$_{12}$, or R$_{10}$ and R$_{13}$ together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$;

R$_x$ is a reactive group;

L is a bond or (Q)$_n$;

each Q is independently NR$_d$, S(O)$_t$, O, C(=X), (C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two NR$_d$ are adjacent and no two O are adjacent;

n is 1-20; and each R$_d$ is H, substituted or unsubstituted alkyl.

In some embodiments, X is O. In other embodiments, A is —NR$_1$R$_{1a}$ and B is =N$^+$R$_4$R$_{4a}$. For example, A is —NR$_1$R$_{1a}$, B is =N$^+$R$_4$R$_{4a}$, and at least one pair of R$_1$ and R$_9$, or R$_4$ and R$_5$ taken together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$.

For example, said at least one ring is substituted by -L-PO$_3^{2-}$ or -L-SO$_3^-$. Alternatively, said at least one ring is substituted by at least one alkyl. In another embodiment, at least one of R$_2$ and R$_3$ is -L-SO$^{3-}$.

In some embodiments, R$_7$ is

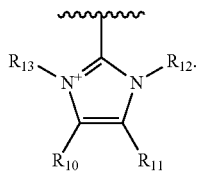

For example, R$_{10}$ and R$_{11}$ are H. Alternatively, R$_{10}$ and R$_{11}$ taken together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$. In another embodiment, at least one of R$_{12}$ and R$_{13}$ is -L-R$_x$. In yet another embodiment, at least one of R$_{12}$ and R$_{13}$ is -L-SO$_3^-$.

The invention further provides compounds of Formula 1a or 1b:

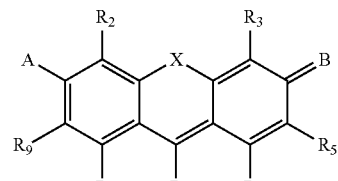

Formula 1a

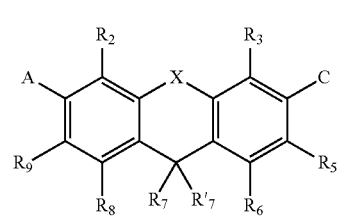

Formula 1b wherein:
X is O, S, or —C(CH$_3$)$_2$—;
A is —OR$_1$ or —NR$_1$R$_{1a}$;
B is =O or =N$^+$R$_4$R$_{4a}$;
C is —OR$_4$ or —NR$_4$R$_{4a}$;
R$_1$, R$_{1a}$, R$_4$, and R$_{4a}$ are each independently H or alkyl, unsubstituted or substituted with -L-SO$_3^-$, -L-PO$_3^{2-}$, a water-soluble polymer, or with -L-R$_x$; or one or more pair of R$_1$ and R$_{1a}$ or R$_4$ and R$_{4a}$ together with the nitrogen to which they are attached form a saturated or unsaturated ring optionally substituted by any of -L-SO$_3^-$, -L-PO$_3^{2-}$ and -L-R$_x$, or substituted with an enzyme substrate or a protecting group;
R$_7$ is:

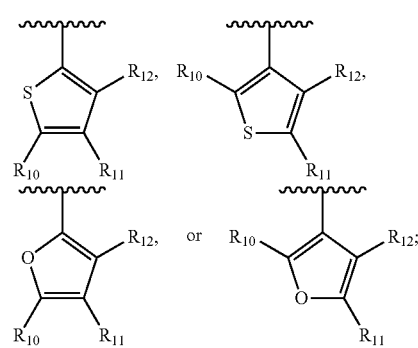

R'$_7$ is H, OH, CN, or C$_1$-C$_6$ alkoxy; or R'$_7$ in combination with R$_7$ forms a 5- or 6-membered spirolactone or spirosultone ring;
R$_2$, R$_3$, R$_5$, R$_6$, R$_8$, R$_9$, R$_{10}$, R$_{11}$, and R$_{12}$ are each independently H, halogen, CN, alkyl, alkenyl, alkoxy, aryl, heteroaryl, -L-PO$_3^{2-}$, -L-SO$_3^-$, or -L-R$_x$; or one or more pair of R$_2$ and R$_{1a}$, R$_3$ and R$_{4a}$, R$_4$ and R$_5$, R$_5$ and R$_6$, R$_8$ and R$_9$, R$_9$ and R$_1$, R$_{10}$ and R$_{11}$, or R$_{11}$ and R$_{12}$ together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-$PO_3^{2-}$, L-$SO_3^-$, or -L-$R_x$;

$R_x$ is a reactive group;

L is a bond or $(Q)_n$;

each Q is independently $NR_d$, $S(O)_t$, O, C(=X), (C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two $NR_d$ are adjacent and no two O are adjacent;

n is 1-20;

each $R_d$ is H, substituted or unsubstituted alkyl; and at least one or more pair of $R_2$ and $R_{1a}$, $R_3$ and $R_{4a}$, $R_4$ and $R_5$, $R_5$ and $R_6$, $R_8$ and $R_9$, $R_9$ and $R_1$, $R_{10}$ and $R_{11}$, or $R_{11}$ and $R_{12}$ together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-$PO_3^{2-}$, L-$SO_3^-$, or -L-$R_x$.

In some embodiments, at least one of $R_{10}$, $R_{11}$, and $R_{12}$ is -L-$SO_3^-$.

Also provided are compounds of Formula 1a or 1b:

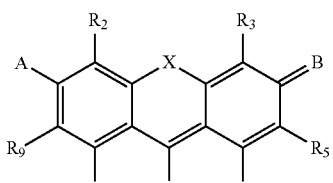

Formula 1a

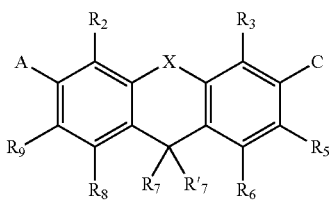

Formula 1b wherein:
X is O, S, or —C(CH$_3$)$_2$—;
A is —$OR_1$ or —$NR_1R_{1a}$;
B is =O or =$N^+R_4R_{4a}$;
C is —$OR_4$ or —$NR_4R_{4a}$;
$R_1$, $R_{1a}$, $R_4$, and $R_{4a}$ are each independently H or alkyl, unsubstituted or substituted with -L-$SO_3^-$, -L-$PO_3^{2-}$, a water-soluble polymer, or with -L-$R_x$; or one or more pair of $R_1$ and $R_{1a}$ or $R_4$ and $R_{4a}$ together with the nitrogen to which they are attached form a saturated or unsaturated ring optionally substituted by any of -L-$SO_3^-$, -L-$PO_3^{2-}$ and -L-$R_x$; or at least one of $R_1$, $R_{1a}$, $R_4$, or $R_{4a}$ is an enzyme substrate or a protecting group;
$R_7$ is:

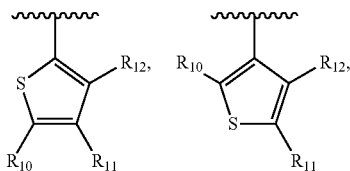

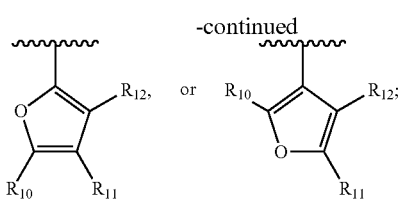

$R'_7$ is H, OH, CN, or $C_1$-$C_6$ alkoxy; or $R'_7$ in combination with $R_7$ forms a 5- or 6-membered spirolactone or spirosultone ring;

$R_2$, $R_3$, $R_5$, $R_6$, $R_8$, $R_9$, $R_{10}$, $R_{11}$, and $R_{12}$ are each independently H, halogen, CN, alkyl, alkenyl, alkoxy, aryl, heteroaryl, -L-$PO_3^{2-}$, -L-$SO_3^-$, or -L-$R_x$; or one or more pair of $R_2$ and $R_{1a}$, $R_3$ and $R_{4a}$, $R_4$ and $R_5$, $R_5$ and $R_6$, $R_8$ and $R_9$, $R_9$ and $R_1$, $R_{10}$ and $R_{11}$, or $R_{11}$ and $R_{12}$ together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-$PO_3^{2-}$, L-$SO_3^-$, or -L-$R_x$;

$R_x$ is a reactive group;

L is a bond or $(Q)_n$;

each Q is independently $NR_d$, $S(O)_t$, O, C(=X), (C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two $NR_d$ are adjacent and no two O are adjacent;

n is 1-20;

each $R_d$ is H, substituted or unsubstituted alkyl; and wherein at least one of $R_2$, $R_3$, $R_5$, $R_6$, $R_8$, $R_9$, $R_{10}$, $R_{11}$, and $R_{12}$ is -L-$SO_3^-$.

In another aspect, the invention provides compounds of Formula 1a or 1b:

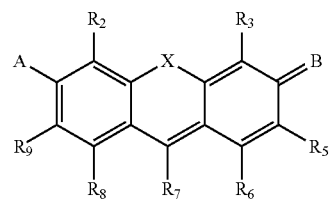

Formula 1a

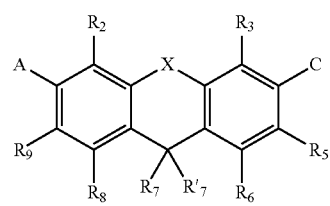

Formula 1b wherein:
X is O, S, or —C(CH$_3$)$_2$—;
A is —$OR_1$ or —$NR_1R_{1a}$;
B is =O or =$N^+R_4R_{4a}$;
C is —$OR_4$ or —$NR_4R_{4a}$;
$R_1$, $R_{1a}$, $R_4$, and $R_{4a}$ are each independently H or alkyl, unsubstituted or substituted with -L-$SO_3^-$, -L-$PO_3^{2-}$, a water-soluble polymer, or with -L-$R_x$; or one or more pair of $R_1$ and $R_{1a}$ or $R_4$ and $R_{4a}$ together with the nitrogen to which they are attached form a saturated or unsaturated ring optionally substituted by any of -L-$SO_3^-$, -L-$PO_3^{2-}$ and -L-$R_x$; or at least one of $R_1$, $R_{1a}$, $R_4$, or $R_{4a}$ is an enzyme substrate or a protecting group; $R_7$ is:

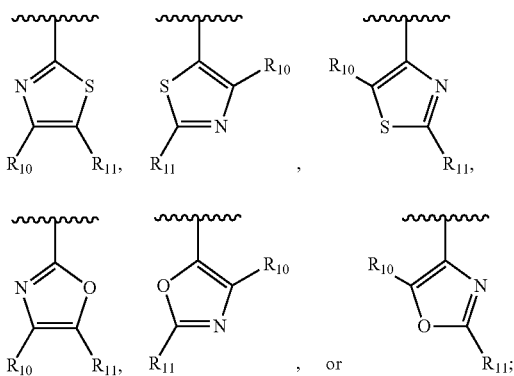

$R'_7$ is H, OH, CN, or $C_1$-$C_6$ alkoxy; or $R'_7$ in combination with $R_7$ forms a 5- or 6-membered spirolactone or spirosultone ring;

$R_2$, $R_3$, $R_5$, $R_6$, $R_8$, $R_9$, $R_{10}$, and $R_{11}$ are each independently H, halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-$PO_3^{2-}$, L-$SO_3^-$, -L-$R_x$; and when $R_7$ is

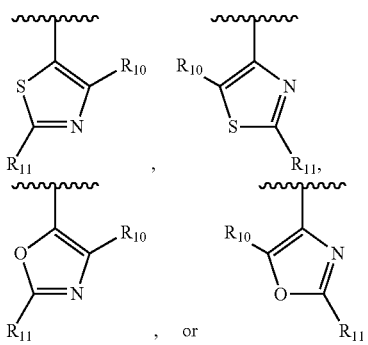

$R_{10}$ is optionally $CO_2^-$; or one or more pair of $R_2$ and $R_{1a}$, $R_3$ and $R_{4a}$, $R_4$ and $R_5$, $R_5$ and $R_6$, $R_8$ and $R_9$, $R_9$ and $R_1$, or $R_{10}$ and $R_{11}$ together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-$PO_3^{2-}$, L-$SO_3^-$, or -L-$R_x$;

$R_x$ is a reactive group;

L is a bond or $(Q)_n$;

each Q is independently $NR_d$, $S(O)_t$, O, C(=X), (C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two $NR_d$ are adjacent and no two O are adjacent;

n is 1-20; and each $R_d$ is H, substituted or unsubstituted alkyl.

In some embodiments, X is O. In other embodiments, A is —$NR_1R_{1a}$ and B is =$N^+R_4R_{4a}$. For example, A is —$NR_1R_{1a}$, B is =$N^+R_4R_{4a}$, and at least one pair of $R_1$ and $R_9$, or $R_4$ and $R_5$ taken together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-$PO_3^{2-}$, L-$SO_3^-$, or -L-$R_x$.

For example, said at least one ring is substituted by -L-$PO_3^{2-}$ or -L-$SO_3^-$. Alternatively, said at least one ring is substituted by at least one alkyl. In another embodiment, at least one of $R_2$ and $R_3$ is -L-$SO^{3-}$.

In some embodiments, $R_7$ is

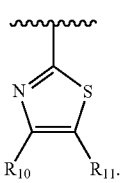

In other embodiments $R_7$ is

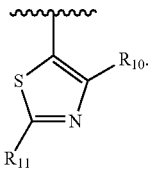

In still other embodiments, $R_7$ is

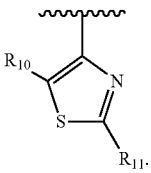

In some embodiments, $R_7$ is

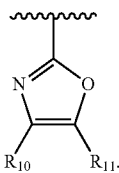

In other embodiments, $R_7$ is

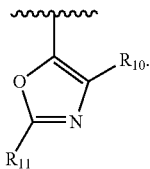

In yet other embodiments, $R_7$ is

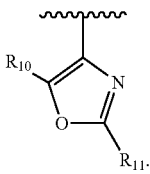

For example, $R_{10}$ and $R_{11}$ are H. Alternatively, $R_{10}$ and $R_{11}$ taken together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-$PO_3^{2-}$, L-$SO_3^-$, or -L-$R_x$. In another embodiment, $R_{12}$ is -L-$R_x$.

The invention also provides compounds of Formula 1a or 1b:

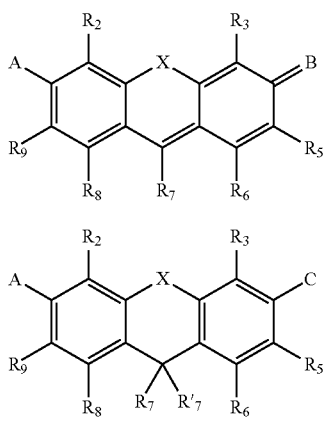

Formula 1a

Formula 1b wherein:
  X is O, S, or —C(CH$_3$)$_2$—;
  A is —OR$_1$ or —NR$_1$R$_{1a}$;
  B is =O or =N$^+$R$_4$R$_{4a}$;
  C is —OR$_4$ or —NR$_4$R$_{4a}$;
  $R_1$, $R_{1a}$, $R_4$, and $R_{4a}$ are each independently H or alkyl, unsubstituted or substituted with -L-$SO_3^-$, -L-$PO_3^{2-}$, a water-soluble polymer, or with -L-$R_x$; or one or more pair of $R_1$ and $R_{1a}$ or $R_4$ and $R_{4a}$ together with the nitrogen to which they are attached form a saturated or unsaturated ring optionally substituted by any of -L-$SO_3^-$, -L-$PO_3^{2-}$ and -L-$R_x$; or at least one of $R_1$, $R_{1a}$, $R_4$, or $R_{4a}$ is an enzyme substrate or a protecting group;

$R_7$ is:

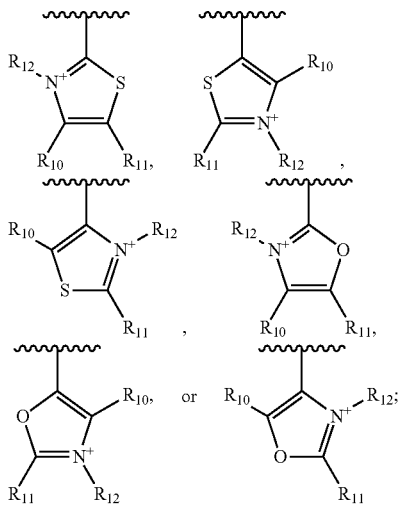

$R'_7$ is $R_{10}H$, OH, CN, or $C_1$-$C_6$ alkoxy; or $R'_7$ in combination with $R_7$ forms a 5- or 6-membered, spirolactone or spirosultone ring;

$R_2$, $R_3$, $R_5$, $R_6$, $R_8$, $R_9$, $R_{10}$, $R_{11}$, and $R_{12}$ are each independently H, halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-$PO_3^{2-}$, L-$SO_3^-$, -L-$R_x$; and when $R_7$ is

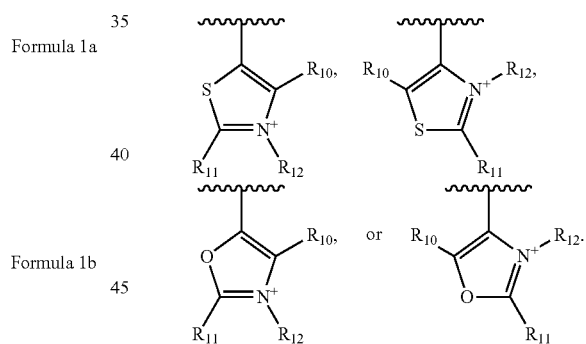

$R_{10}$ is optionally $CO_2^-$, or when $R_7$ is

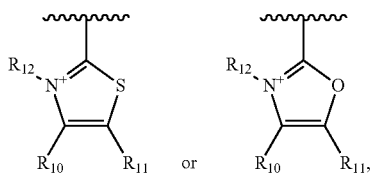

$R_{12}$ is $CO^{2-}$; or one or more pair of $R_2$ and $R_{1a}$, $R_3$ and $R_{4a}$, $R_4$ and $R_5$, $R_5$ and $R_6$, $R_8$ and $R_9$, $R_9$ and $R_1$, $R_{10}$ and $R_{11}$, $R_{10}$ and $R_{12}$, or $R_{11}$ and $R_{12}$ together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$;

R$_x$ is a reactive group;

L is a bond or (Q)$_n$;

each Q is independently NR$_d$, S(O)$_t$, O, C(=X), (C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two NR$_d$ are adjacent and no two O are adjacent;

n is 1-20; and each R$_d$ is H, substituted or unsubstituted alkyl.

In some embodiments, X is O. In other embodiments, A is —NR$_1$R$_{1a}$ and B is =N$^+$R$_4$R$_{4a}$. For example, A is —NR$_1$R$_{1a}$, B is =N$^+$R$_4$R$_{4a}$, and at least one pair of R$_1$ and R$_9$, or R$_4$ and R$_5$ taken together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$.

For example, said at least one ring is substituted by -L-PO$_3^{2-}$ or -L-SO$_3^-$. Alternatively, said at least one ring is substituted by at least one alkyl. In another embodiment, at least one of R$_2$ and R$_3$ is -L-SO$^{3-}$.

In some embodiments, R$_7$ is

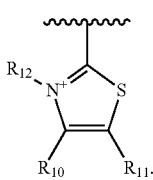

In other embodiments R$_7$ is

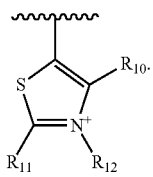

In still other embodiments, R$_7$ is

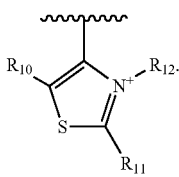

In some embodiments, R$_7$ is

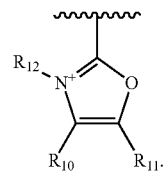

In other embodiments, R$_7$ is

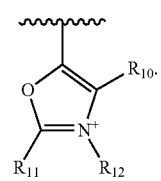

In yet other embodiments, R$_7$ is

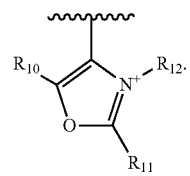

For example, R$_{10}$ and R$_{11}$ are H. Alternatively, R$_{10}$ and R$_{11}$ taken together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$. In another embodiment, R$_{12}$ is -L-R$_x$.

The invention further provides compounds of Formula 1a or 1b:

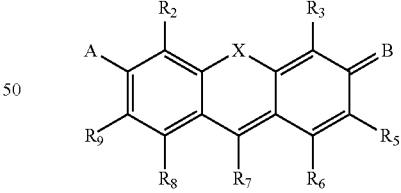

Formula 1a

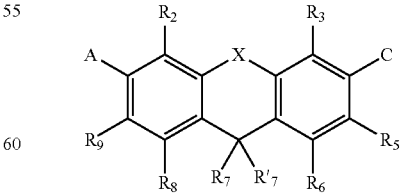

Formula 1b wherein:
X is O, S, or —C(CH$_3$)$_2$—;
A is —OR$_1$ or —NR$_1$R$_{1a}$;
B is =O or =N$^+$R$_4$R$_{4a}$;

C is —OR$_4$ or —NR$_4$R$_{4a}$;

R$_1$, R$_{1a}$, R$_4$, and R$_{4a}$ are each independently H or alkyl, unsubstituted or substituted with -L-SO$_3^-$, -L-PO$_3^{2-}$, a water-soluble polymer, or with -L-R$_x$; or one or more pair of R$_1$ and R$_{1a}$ or R$_4$ and R$_{4a}$ together with the nitrogen to which they are attached form a saturated or unsaturated ring optionally substituted by any of -L-SO$_3^-$, -L-PO$_3^{2-}$ and -L-R$_x$; or at least one of R$_1$, R$_{1a}$, R$_4$, or R$_{4a}$ is an enzyme substrate or a protecting group;

R$_7$ is:

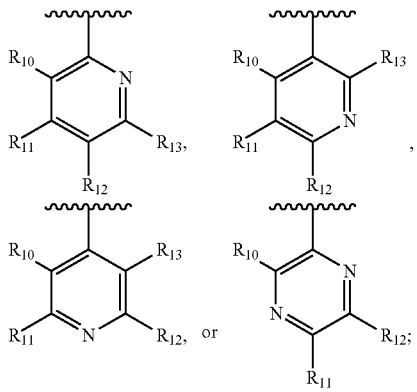

R'$_7$ is H, OH, CN, or C$_1$-C$_6$ alkoxy; or R'$_7$ in combination with R$_7$ forms a 5- or 6-membered spirolactone or spirosultone ring;

R$_2$, R$_3$, R$_5$, R$_6$, R$_8$, R$_9$, R$_{10}$, R$_{11}$, R$_{12}$ and R$_{13}$ are each independently H, halogen, CN, alkyl, alkenyl, alkoxy, aryl, heteroaryl, -L-PO$_3^{2-}$, -L-SO$_3^-$, or -L-R$_x$; and R$_{10}$ or R$_{13}$ are optionally CO$_2^-$; or one or more pair of R$_2$ and R$_{1a}$, R$_3$ and R$_{4a}$, R$_4$ and R$_5$, R$_5$ and R$_6$, R$_8$ and R$_8$, R$_9$ and R$_1$, R$_{10}$ and R$_{11}$, R$_{11}$ and R$_{12}$, or R$_{12}$ and R$_{13}$ together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$;

R$_x$ is a reactive group;

L is a bond or (Q)$_n$;

each Q is independently NR$_d$, S(O)$_t$, O, C(=X), (C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two NR$_d$ are adjacent and no two O are adjacent;

n is 1-20;

each R$_d$ is H, substituted or unsubstituted alkyl; and at least one of R$_2$, R$_3$, R$_5$, R$_6$, R$_8$, R$_9$, R$_{10}$, R$_{11}$, R$_{12}$ and R$_{13}$ is -L-PO$_3^{2-}$, -L-SO$_3^-$, or -L-R$_x$.

For example, at least one of R$_2$, R$_3$, R$_5$, R$_6$, R$_8$, R$_9$, R$_{10}$, R$_{11}$, R$_{12}$ and R$_{13}$ is -L-SO$_3^-$. In other embodiments, A is —NR$_1$R$_{1a}$ and B is =N$^+$R$_4$R$_{4a}$, and at least one pair of R$_1$ and R$_9$, or R$_4$ and R$_5$ taken together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$.

For example, at least one ring is substituted by -L-PO$_3^{2-}$ or -L-SO$_3^-$, or said at least one ring is substituted by at least one alkyl. In one embodiment, at least one of R$_2$ and R$_3$ is -L-SO$^{3-}$.

The invention also provides compounds of Formula 1a or 1b:

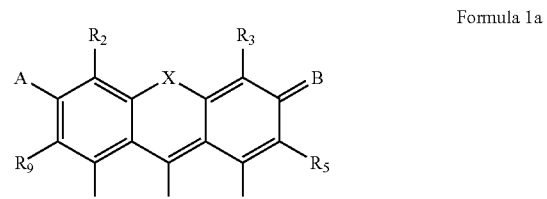

Formula 1a

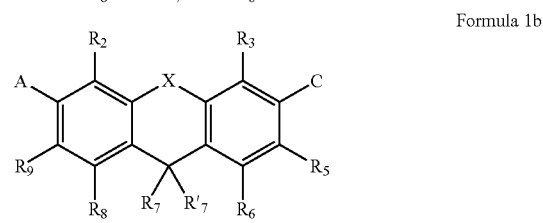

Formula 1b wherein:

X is O, S, or —C(CH$_3$)$_2$—;

A is —OR$_1$ or —NR$_1$R$_{1a}$;

B is =O or =N$^+$R$_4$R$_{4a}$;

C is —OR$_4$ or —NR$_4$R$_{4a}$;

R$_1$, R$_{1a}$, R$_4$, and R$_{4a}$ are each independently H or alkyl, unsubstituted or substituted with -L-SO$_3^-$, -L-PO$_3^{2-}$, a water-soluble polymer, or with -L-R$_x$; or one or more pair of R$_1$ and R$_{1a}$ or R$_4$ and R$_{4a}$ together with the nitrogen to which they are attached form a saturated or unsaturated ring optionally substituted by any of -L-SO$_3^-$, -L-PO$_3^{2-}$ and -L-R$_x$; or at least one of R$_1$, R$_{1a}$, R$_4$, or R$_{4a}$ is an enzyme substrate or a protecting group;

R$_7$ is a 5-10 membered monocyclic or bicyclic heterocycle, unsubstituted or substituted with halogen, CO$_2^-$, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$;

R'$_7$ is H, OH, CN, or C$_1$-C$_6$ alkoxy; or R'$_7$ in combination with R$_7$ forms a 5- or 6-membered spirolactone or spirosultone ring;

R$_2$, R$_3$, R$_5$, R$_6$, R$_8$, R$_9$, are each independently H, halogen, CN, alkyl, alkenyl, alkoxy, aryl, heteroaryl, -L-PO$_3^{2-}$, -L-SO$_3^-$, or -L-R$_x$; or one or more pair of R$_2$ and R$_{1a}$, R$_3$ and R$_{4a}$, R$_4$ and R$_5$, R$_5$ and R$_6$, R$_8$ and R$_9$, or R$_9$ and R$_1$, together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$;

R$_x$ is a reactive group;

L is a bond or (Q)$_n$;

each Q is independently NR$_d$, S(O)$_t$, O, C(=X), (C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two $NR_d$ are adjacent and no two O are adjacent; n is 1-20;

each $R_d$ is H, substituted or unsubstituted alkyl; and at least one of $R_2$, $R_3$, $R_5$, $R_6$, $R_8$, or $R_9$ is $-L-SO_3^-$.

In another aspect, the invention provides a reaction mixture comprising:

a) an aminophenol or resorcinol precursor of formula:

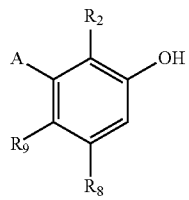 and/or 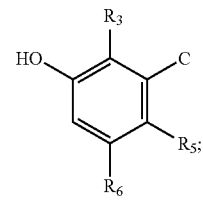

b) an aldehyde precursor of formula

or a diacetal derivative thereof; and c) an acid catalyst;

wherein A is $-OR_1$ or $-NR_1R_{1a}$;

C is $-OR_4$ or $-NR_4R_{4a}$;

$R_1$, $R_{1a}$, $R_4$, and $R_{4a}$ are each independently H or alkyl, unsubstituted or substituted with $-L-SO_3^-$, $-L-PO_3^{2-}$, a water-soluble polymer, or with $-L-R_x'$; or one or more pair of $R_1$ and $R_{1a}$ or $R_4$ and $R_{4a}$ together with the nitrogen to which they are attached form a saturated or unsaturated ring optionally substituted by any of $-L-SO_3^-$, $-L-PO_3^{2-}$ and $-L-R_x'$; or at least one of $R_1$, $R_{1a}$, $R_4$, or $R_{4a}$ is an enzyme substrate or a protecting group;

$R_2$, $R_3$, $R_5$, $R_6$, $R_8$ and $R_9$ are H or alkyl, unsubstituted or substituted with $-L-SO_3^-$, $-L-PO_3^{2-}$, a water-soluble polymer, or with $-L-R_x'$; or one or more pair of $R_1$ and $R_{1a}$ or $R_4$ and $R_{4a}$ together with the nitrogen to which they are attached form a saturated or unsaturated ring optionally substituted by any of $-L-SO_3^-$, $-L-PO_3^{2-}$ and $-L-R_x'$;

$R_7$ is a 5-10 membered monocyclic or bicyclic heterocycle, unsubstituted or substituted with halogen, $CO_2^-$, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, $-L-PO_3^{2-}$, $L-SO_3^-$, or $-L-R_x'$;

$R_x'$ is a protected $R_x$ moiety or a chemical precursor of a $R_x$ moiety;

L is a bond or $(Q)_n$;

each Q is independently $NR_d$, $S(O)_t$, O, $C(=X)$, $(C=X)$, substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two $NR_d$ are adjacent and no two O are adjacent; n is 1-20; and each $R_d$ is H, substituted or unsubstituted alkyl.

In one embodiment, the reaction mixture additionally comprises a solvent capable of at least partially dissolving said aldehyde and said aminophenol or resorcinol precursors.

In another embodiment, the reaction mixture additionally comprises a compound of formula:

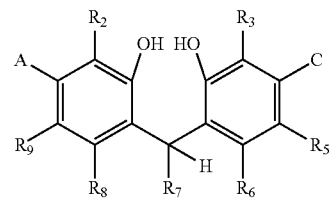

For example, $R_7$ is

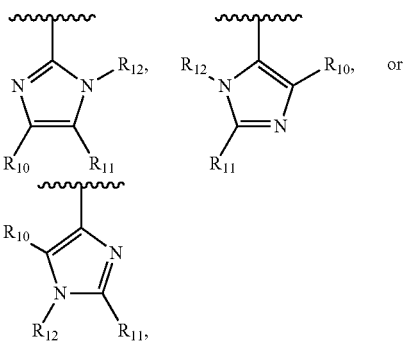

wherein $R_{10}$, $R_{11}$, and $R_{12}$ are each independently H, halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, $-L-PO_3^{2-}$, $L-SO_3^-$, or $-L-R_x'$.

Also provided is a method of preparing a fluorescent dye precursor comprising the steps of:

a) preparing a reaction mixture comprising an aminophenol or resorcinol precursor of formula:

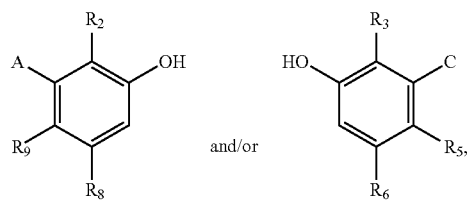

an aldehyde precursor of formula

or a diacetal derivative thereof, and an acid catalyst;

b) incubating said mixture between 0 and 100° C. for a time sufficient to result in a fluorescent dye precursor of the formula:

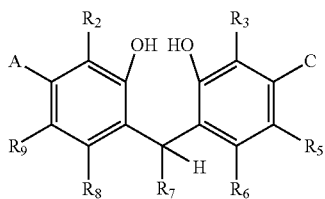

wherein A is —OR$_1$ or —NR$_1$R$_{1a}$;
C is —OR$_4$ or —NR$_4$R$_{4a}$;
R$_1$, R$_{1a}$, R$_4$, and R$_{4a}$ are each independently H or alkyl, unsubstituted or substituted with -L-SO$_3^-$, -L-PO$_3^{2-}$, a water-soluble polymer, or with -L-R$_x$'; or one or more pair of R$_1$ and R$_{1a}$ or R$_4$ and R$_{4a}$ together with the nitrogen to which they are attached form a saturated or unsaturated ring optionally substituted by any of -L-SO$_3^-$, -L-PO$_3^{2-}$ and -L-R$_x$'; or at least one of R$_1$, R$_{1a}$, R$_4$, or R$_{4a}$ is an enzyme substrate or a protecting group;
R$_2$, R$_3$, R$_5$, R$_6$, R$_8$, and R$_9$ are H or alkyl, unsubstituted or substituted with -L-SO$_3^-$, -L-PO$_3^{2-}$, a water-soluble polymer, or with -L-R$_x$'; or one or more pair of R$_1$ and R$_{1a}$ or R$_4$ and R$_{4a}$ together with the nitrogen to which they are attached form a saturated or unsaturated ring optionally substituted by any of -L-SO$_3^-$, -L-PO$_3^{2-}$ and -L-R$_x$';
R$_7$ is a 5-10 membered monocyclic or bicyclic heterocycle, unsubstituted or substituted with halogen, CO$_2^-$, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$';
R$_x$' is a protected R$_x$ moiety or a chemical precursor of a R$_x$ moiety;
L is a bond or (Q)$_n$;
each Q is independently NR$_d$, S(O)$_t$, O, C(=X), (C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two NR$_d$ are adjacent and no two O are adjacent;
n is 1-20; and
each R$_d$ is H, substituted or unsubstituted alkyl.
For example, R$_7$ is

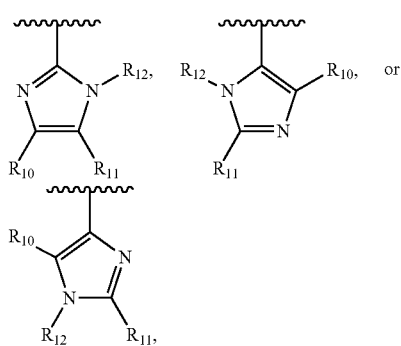

wherein R$_{10}$, R$_{11}$, and R$_{12}$ are each independently H, halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$'.

The invention further provides a method of preparing a fluorescent dye comprising the steps of:
a) providing a fluorescent dye precursor of formula:

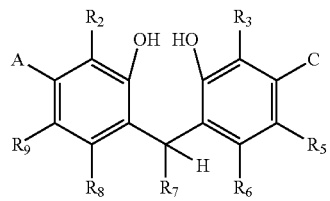

b) incubating said precursor with an oxidizer for a time sufficient to result in the formation of a compound of formula:

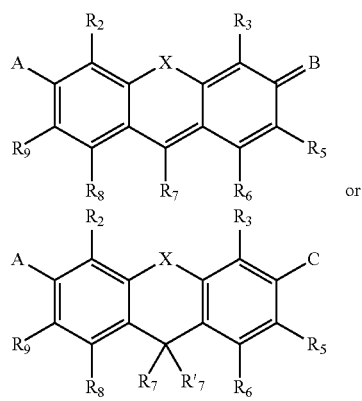

wherein A is —OR$_1$ or —NR$_1$R$_{1a}$;
B is =O or =N$^+$R$_4$R$_{4a}$;
C is —OR$_4$ or —NR$_4$R$_{4a}$;
R$_1$, R$_{1a}$, R$_4$, and R$_{4a}$ are each independently H or alkyl, unsubstituted or substituted with -L-SO$_3^-$, -L-PO$_3^{2-}$, a water-soluble polymer, or with -L-R$_x$'; or one or more pair of R$_1$ and R$_{1a}$ or R$_4$ and R$_{4a}$ together with the nitrogen to which they are attached form a saturated or unsaturated ring optionally substituted by any of -L-SO$_3^-$, -L-PO$_3^{2-}$ and -L-R$_x$'; or at least one of R$_1$, R$_{1a}$, R$_4$, or R$_{4a}$ is an enzyme substrate or a protecting group;
R$_2$, R$_3$, R$_5$, R$_6$, R$_8$, and R$_9$ are H or alkyl, unsubstituted or substituted with -L-SO$_3^-$, -L-PO$_3^{2-}$, a water-soluble polymer, or with -L-R$_x$'; or one or more pair of R$_1$ and R$_{1a}$ or R$_4$ and R$_{4a}$ together with the nitrogen to which they are attached form a saturated or unsaturated ring optionally substituted by any of -L-SO$_3^-$, -L-PO$_3^{2-}$ and -L-R$_x$';
R$_7$ is a 5-10 membered monocyclic or bicyclic heterocycle, unsubstituted or substituted with halogen, CO$_2^-$, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$';
R$_x$' is a protected R$_x$ moiety or a chemical precursor of a R$_x$ moiety;
L is a bond or (Q)$_n$;
each Q is independently NR$_d$, S(O)$_t$, O, C(=X), (C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two $NR_d$ are adjacent and no two O are adjacent; n is 1-20; and each $R_d$ is H, substituted or unsubstituted alkyl.

The oxidizer is, for example, 2,3,5,6-tetrachloro-p-Benzoquinone (p-chloroanil) or 2,3-dichloro-5,6-dicyanobenzoquinone (DDQ).

Also provided herein is a kit comprising: i) a compound of the invention and ii) instructions instructing the use of the compound. Optionally, the kit comprises iii) a buffer; and/or iv) materials or devices for purifying conjugation products.

Provided herein is a biomolecule comprising a label having a structure of a compound of the invention comprising at least one reactive moiety, wherein the at least one reactive moiety of the compounds has undergone a reaction which attaches the label to the biomolecule. In some embodiments, the biomolecule comprises a polynucleotide. In some embodiments, the biomolecule comprises a polypeptide. In some embodiments, the polypeptide further comprises an antigen binding site. In some embodiments, the polypeptide is a whole immunoglobulin. In some embodiments, the polypeptide is a Fab fragment.

The invention further provides an immunoglobin comprising a label having a structure of a compound of the invention, wherein at least one reactive moiety of the compound of the invention has undergone a reaction which attaches the label to the immunoglobin, wherein the immunoglobin is an antibody that binds specifically to an antigen, including but not limited to an antigen on a cancer cell. In some embodiments, the immunoglobin is an antibody that binds to erb2.

In some embodiments, the method of labeling a biomolecule comprises reacting a compound of the invention comprising a reactive moiety with a substrate biomolecule under conditions sufficient to effect crosslinking between the compound and the substrate biomolecule. In some embodiments, the substrate biomolecule is a protein, polypeptide, a polynucleotide, a carbohydrate, a lipid, a metal chelator or a combination thereof. In some embodiments, the substrate biomolecule is a polynucleotide.

Provided herein a method for labeling a cell within a population of cells whereby the cell is differentially labeled relative to neighboring cells within the population, the method comprising contacting the cell with a labeled biomolecule, wherein the biomolecule comprises a targeting moiety that binds to a binding partner that is indicative of the cell, and thereby differentially labeling the cell relative to neighboring cells within the population.

In some embodiments, the method further comprises the step of imaging the cell, the imaging step comprising:
i) directing exciting wavelength to the cell; and
ii) detecting emitted fluorescence from the cell.

In some embodiments, the labeling takes place in vitro. In some embodiments, the labeling takes place in vivo.

Provided herein is also an immunoglobulin labeled with a fluorescent compound of the invention comprising a fluorophore that has an absorption maximal wavelength of about 488, 514, 532, 543, 568, 594, 633, 640 or 647 nm.

In some embodiments, the immunoglobulin retains binding specificity to a target upon conjugation to the fluorescent compound. In some embodiments, the immunoglobin is an antibody that binds specifically to an antigen including but not limited to an antigen on a cancer cell. In some embodiments, the antibody binds to erb2. In some embodiments, the immunoglobulin comprises a fluorescent compound of the invention.

Provided herein is a method of labeling a polypeptide comprising: forming a complex that comprises the polypeptide and a binding agent, wherein the binding agent comprises a fluorescent label having a structure of the invention comprising at least one reactive moiety, wherein the at least one reactive moiety has undergone a reaction which attaches the label to the binding agent.

In some embodiments the binding agent is an antibody.

In some embodiments of the method the complex comprises (a) a primary antibody that binds to the polypeptide, and (b) the binding agent which functions as a secondary antibody exhibiting binding capability to the primary antibody.

In some embodiments, the labeling occurs on a solid substrate.

In some embodiments, the complex yields a signal to noise ratio greater than about 100, wherein the signal to noise ratio is calculated by the formula:

(fluorescent signal from a complex comprising the polypeptide bound by a primary antibody which in turn is bound to the binding agent)/(fluorescent signal from a mixture of the polypeptide, an isotype control primary antibody and the binding agent).

In some embodiments, the complex yields a signal to noise ratio greater than about 250, wherein the signal to noise ratio is calculated by the formula:

(fluorescent signal from a complex comprising the polypeptide bound by a primary antibody which in turn is bound to the binding agent)/(fluorescent signal from a mixture of the polypeptide, an isotype control primary antibody and the binding agent).

In some embodiments, the complex yields a signal to noise ratio greater than about 270, wherein the signal to noise ratio is calculated by the formula:

(fluorescent signal from a complex comprising the polypeptide bound by a primary antibody which in turn is bound to the binding agent)/(fluorescent signal from a mixture of the polypeptide, an isotype control primary antibody and the binding agent).

In some embodiments, each complex is present at identical protein concentrations.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
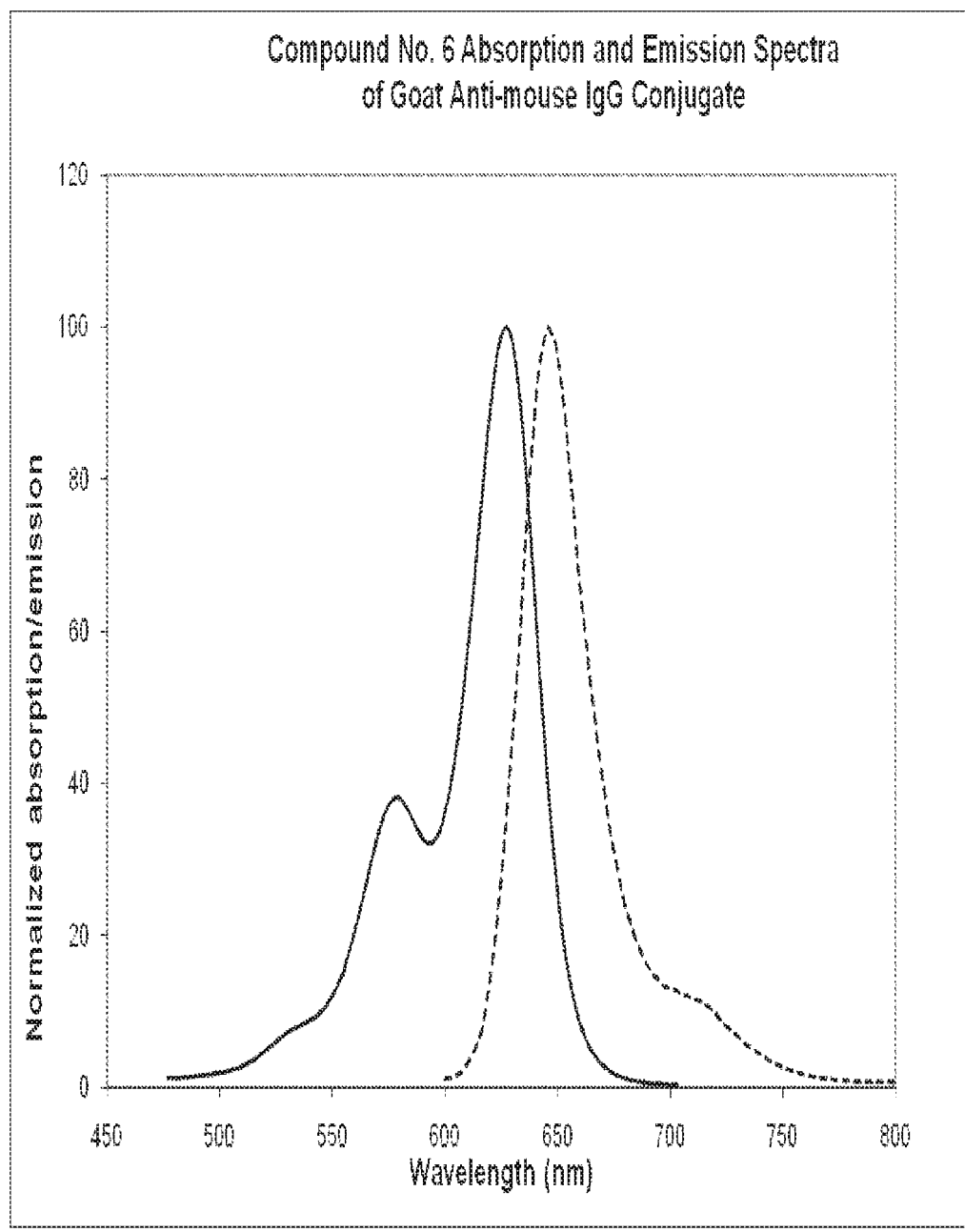
FIG. 1 is a graphical representation of the absorption and emission spectra of compound No. 6 conjugated to goat anti-mouse IgG in PBS.

The present invention discloses novel xanthene dyes substituted by heterocyclic groups. The dyes may be used for any application, including the labeling of molecules and biomolecules such as polypeptides, polynucleotides and/or metal chelators and are also suitable for use in a wide range of other applications, including diagnostic and imaging systems. In some aspect of the invention, the dyes are used for labeling proteins, such as primary or secondary antibodies, with reduced dye aggregation and consequently brighter fluorescence signals in biological detection schemes such as flow cytometry or microscopy.

Definitions:

The compounds of the present invention may have asymmetric centers, chiral axes, and chiral planes (as described in: E. L. Eliel and S. H. Wilen, Stereo-chemistry of Carbon Compounds, John Wiley & Sons, New York, 1994, pages 1119 1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted.

When any variable (e.g. $R_x$, L, Q) occurs more than one time in any constituent, its definition on each occurrence is independent at every other occurrence. Combinations of substituents and variables are permissible when such combinations result in stable compounds. Lines drawn into the ring systems from substituents indicate that the indicated bond may be attached to any of the substitutable ring carbon or nitrogen atoms or a ring nitrogen that can be quaternized. If the ring system is polycyclic, it is intended that the bond be attached to any of the suitable carbon or nitrogen atoms on the proximal ring only. Substitution of a ring by a substitutent generally allows the substituent to be a cyclic structure fused to the ring.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, "alkyl" is intended to include both branched, straight-chain, and cyclic saturated aliphatic hydrocarbon groups. Alkyl groups specifically include methyl, ethyl, propyl, butyl, pentyl, hexyl, heptyl, octyl, nonyl, decyl, and so on, as well as cycloalkyls such as cyclopropyl, cyclobutyl, cyclopentyl, cyclohexyl, tetrahydronaphthalene, methylenecylohexyl, and so on. For example, an alkyl chain designated as $C_1$-$C_{20}$ may have from 1 to 20 carbon atoms. "Alkoxy" represents an alkyl group attached through an oxygen bridge.

The term "alkenyl" refers to a non-aromatic hydrocarbon group, straight, branched or cyclic, containing at least one carbon to carbon double bond. Alkenyl groups include, but are not limited to, ethenyl, propenyl, butenyl and cyclohexenyl. For example, an alkenyl chain designated as $C_2$-$C_{20}$ may have from 1 to 20 carbon atoms The straight, branched or cyclic portion of the alkenyl group may contain double bonds and may be substituted if a substituted alkenyl group is indicated.

The term "alkynyl" refers to a hydrocarbon group, straight, branched or cyclic, containing at least one carbon to carbon triple bond. Alkynyl groups include, but are not limited to, ethynyl, propynyl and butynyl. For example, an alkenyl chain designated as $C_2$-$C_{20}$ may have from 2 to 20 carbon atoms. The straight, branched or cyclic portion of the alkynyl group may contain triple bonds and may be substituted if a substituted alkynyl group is indicated.

As used herein, "aryl" is intended to mean any stable monocyclic or polycyclic carbon ring of up to 7 atoms in each ring, wherein at least one ring is aromatic. Examples of such aryl elements include phenyl, naphthyl, tetrahydronaphthyl, indanyl, biphenyl, phenanthryl, anthryl or acenaphthyl. For example, an aryl group may be a 6-carbon monocyclic or 10-carbon bicyclic aromatic ring system wherein 0, 1, 2, 3, or 4 atoms of each ring may be substituted by a substituent. In cases where the aryl substituent is bicyclic and one ring is non-aromatic, it is understood that attachment is via the aromatic ring.

The term "heteroaryl", as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to imidazolyl, benzimidazolyl, acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, pyrazinyl, pyridazinyl, pyridinyl, pyrimidinyl, pyrrolyl, tetrahydroquinoline, xanthenyl, and coumarinyl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" as used herein is intended to mean a 5- to 10-membered aromatic or nonaromatic heterocycle containing at least one heteroatom which is O, N or S. This definition includes bicyclic groups. "Heterocyclyl" therefore includes the above mentioned heteroaryls, as well as dihydro and tetrahydro analogs thereof. Further examples of "heterocyclyl" include, but are not limited to the following: benzimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

The alkyl, alkenyl, alkynyl, cycloalkyl, aryl, heteroaryl and heterocyclyl substituents may be unsubstituted or unsubstituted, unless specifically defined otherwise. For example, an alkyl group may be substituted with one or more substituents selected from OH, oxo, halo, alkoxy, dialkylamino, $-PO_3^{2-}$, $-SO_3^{2-}$, $-CO_2^-$, a reactive group, or heterocyclyl, such as morpholinyl or piperidinyl.

The terms "halo" and "halogen" are intended to include chloro, fluoro, bromo and iodo groups.

The term "aromatic" is used in its usual sense, including unsaturation that is essentially delocalized across multiple bonds, such as around a ring.

The term "substituent" refers to an atom, radical or chemical group which replaces a hydrogen in a substituted chemical group, radical, molecule, moiety or compound. In some cases, "substituent" may refer to an atom, radical or chemical group which replaces a lone-pair electron on a nitrogen. In such cases, the substituent may alternatively be referred to as a quarternizing group or quarternizing substituent.

Unless otherwise stated, the term "radical", as applied to any molecule or compound, is used to refer to a part, fragment or group of the molecule or compound rather than to a "free radical". A radical may be linked to another moiety through a covalent bond.

The term "reactive group" refers to a chemical moiety capable of reacting with a reaction partner on a substrate or substrate molecule to form a covalent bond. A compound of the invention can be used to label a wide variety of molecules or substrates that contain a suitable reaction partner or are derivatized to contain a suitable reaction partner. "Reactive group" and "reaction partner" may refer to groups on a compound of the present invention, or to groups on a molecule to be labeled. Here, by way of convenience, but not limitation, a bond-forming group on a compound will generally be referred to as a reactive group and a bond-forming group on the substrate molecule will generally be referred to as a reaction partner. "Reaction substrate", "substrate" and "reaction partner" are used interchangeably throughout this document.

The terms "polynucleotides", "nucleic acids", "nucleotides", "probes" and "oligonucleotides" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. "Polynucleotide" may also be used to refer to peptide nucleic acids (PNA), locked nucleic acids (LNA), threofuranosyl nucleic acids (TNA) and other unnatural nucleic acids or nucleic acid mimics. Other base and backbone modifications known in the art are encompassed in this definition. See, e.g. De Mesmaeker et al (1997) Pure & Appl. Chem., 69, 3, pp 437-440.

The terms "polypeptide", "peptide" and "protein" are used interchangeably herein to refer to polymers of amino acids of any length. The polymer may be linear, cyclic, or branched, it may comprise modified amino acids, and it may be interrupted by non-amino acids. The terms also encompass amino acid polymers that have been modified, for example, via sulfonation, glycosylation, lipidation, acetylation, phosphorylation, iodination, methylation, oxidation, proteolytic processing, phosphorylation, prenylation, racemization, selenoylation, transfer-RNA mediated addition of amino acids to proteins such as arginylation, ubiquitination, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

The term "antibody" as used herein refers to immunoglobulin molecules and immunologically active portions of immunoglobulin molecules, i.e., molecules that contain an antigen-binding site which specifically binds ("immunoreacts with") an antigen. Structurally, the simplest naturally occurring antibody (e.g., IgG) comprises four polypeptide chains, two heavy (H) chains and two light (L) chains inter-connected by disulfide bonds. The immunoglobulins represent a large family of molecules that include several types of molecules, such as IgD, IgG, IgA, IgM and IgE. The term "immunoglobulin molecule" includes, for example, hybrid antibodies, or altered antibodies, and fragments thereof. It has been shown that the antigen binding function of an antibody can be performed by fragments of a naturally-occurring antibody. These fragments are collectively termed "antigen-binding units".

Antigen binding units can be broadly divided into "single-chain" ("Sc") and "non-single-chain" ("Nsc") types based on their molecular structures.

Also encompassed within the terms "antibodies" are immunoglobulin molecules of a variety of species origins including invertebrates and vertebrates. The term "human" as applies to an antibody or an antigen binding unit refers to an immunoglobulin molecule expressed by a human gene or fragment thereof. The term "humanized" as applies to a non-human (e.g. rodent or primate) antibodies are hybrid immunoglobulins, immunoglobulin chains or fragments thereof which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, rabbit or primate having the desired specificity, affinity and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance and minimize immunogenicity when introduced into a human body. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody may also comprise at least a portion of an immunoglobulin constant region (Fc), typically that of a human immunoglobulin.

The term "stable" refers to compositions and compounds which have sufficient chemical stability to survive isolation from a reaction mixture to a useful degree of purity for use in a desired application.

The terms "fluorescent group", "fluorophore", "dye" or "fluorescent group" refer interchangeably to molecules, groups or radicals which are fluorescent. The term "fluorescent" as applied to a molecule of compound is used to refer to the property of the compound of absorbing energy (such as UV, visible or IR radiation) and re-emitting at least a fraction of that energy as light over time. Fluorescent groups, compounds or fluorophores include, but are not limited to discrete compounds, molecules, proteins and macromolecular complexes. Fluorophores also include compounds that exhibit long-lived fluorescence decay such as lanthanide ions and lanthanide complexes with organic ligand sensitizers.

A "subject" as used herein refers to a biological entity containing expressed genetic materials. The biological entity is in various embodiments, a vertebrate. In some embodiment, the biological entity is a mammal. In other embodiments, the subject is a biological entity which comprises a human.

A "control" is an alternative subject or sample used in an experiment for comparison purposes. A control can be "positive" or "negative". For example, where the purpose of the experiment is to detect a differentially expressed transcript or polypeptide in cell or tissue affected by a disease of concern, it is generally preferable to use a positive control (a subject or a sample from a subject, exhibiting such differential expression and syndromes characteristic of that disease), and a negative control (a subject or a sample from a subject lacking the differential expression and clinical syndrome of that disease).

The term "FRET" refers to fluorescence resonance energy transfer. In the present invention, FRET refers to energy transfer processes occurring between at least two fluorescent compounds, between a fluorescent compound and a non-fluorescent component or between a fluorescent component and a non-fluorescent component.

A "binding agent" is a molecule that exhibits binding selectivity towards a binding partner or a target molecule to which it binds. A binding agent may be a biomolecule such as a polypeptide such as an antibody or protein, polypeptide-based toxin, amino acid, nucleotide, polynucleotides including DNA and RNA, lipids, and carbohydrates, or a combination thereof. A binding agent may also be a hapten, drug, ion-complexing agent such as metal chelators, microparticles, synthetic or natural polymers, cells, viruses, or other fluorescent molecules including the dye molecule according to the invention.

A "targeting moiety" is the portion of the binding agent that binds to a binding partner. A targeting moiety may be, without limitation, a nucleotide sequence within a polynucleotide that selectively binds to another polynucleotide or polypeptide. Another nonlimiting example of a targeting moiety may be a polypeptide sequence within a larger polypeptide sequence which binds specifically to a polynucleotide sequence or a second polypeptide sequence. A targeting moiety may be a small molecule or structural motif which will bind to a protein receptor, another small molecule motif, or complexing agent, without limitation. The selective binding may be a specific binding event.

A "binding partner" is a molecule or particle which is bound by the targeting moiety. It can be a cell, virus, fragment of a cell, antibody, fragment of an antibody, peptide, protein, polynucleotide, antigen, small molecule, or a combination thereof. It may be bound selectively or specifically by the binding agent.

The term "signal to noise ratio" of fluorescence as referred to herein in the context of a polypeptide-antibody complex, is the ratio of (fluorescent signal from a complex comprising a polypeptide bound by a primary antibody which in turn is bound to a binding agent labeled with a compound of the invention)/(fluorescent signal from a mixture of the polypeptide, an isotype control primary antibody, and the labeled binding agent).

"Degree of labeling" or "DOL" as used herein refers to the number of dye molecules which are attached per target molecule (including but not limited to polypeptide and polynucleotide). For example, a single dye molecule per a polypeptide such as an antibody represents a 1.0 degree of labeling (DOL). If more than one dye molecule, on average, reacts with and is crosslinked to a polypeptide such as an antibody, the degree of labeling is greater than 1 and may further be a number other than a whole integer. The higher the number of DOL, the greater extent of labeling.

"Intracellular" as used herein refers to the presence of a given molecule in a cell. An intracellular molecule can be present within the cytoplasm, attached to the cell membrane, on the surface of an organelle, or within an organelle of a cell.

"Substrate" or "solid substrate" when used in the context of a reaction surface refers to the material that certain interaction is assayed. For example, a substrate in this context can be a surface of an array or a surface of microwell. It may also be a solid such as a polymer which does not form a specific shape but has attachment points on its surface. In some cases, "substrate" may refer to an enzyme substrate, which is a molecule or biomolecule capable of being chemically transformed by an enzyme.

The terms "wavelength of maximum excitation" and "maximal fluorescence excitation wavelength" are used herein interchangeably. These terms refer to the wavelength at which a fluorescent compound is excited to emit maximal fluorescence. The term "absorption maximal wavelength" as applied to a dye refers the wavelength at which a fluorescent dye or nonfluorescent dye has maximal absorption. A fluorescent dye has a "maximal fluorescence emission wavelength" which is the wavelength at which the dye most intensely fluoresces. When a single wavelength is referred to for any dye, it refers to the maximal wavelength of excitation, absorption, or emission, according to the context of the term, for example, an absorption wavelength refers to the wavelength at which the compound has maximal absorption, and an emission wavelength refers to the wavelength at which the dye most intensely fluoresces.

Compounds of the Invention:

The invention provides compounds of Formula Ia or Ib:

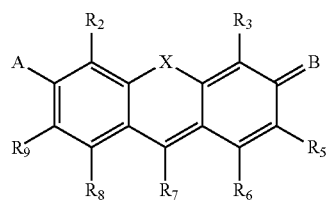

Formula Ia

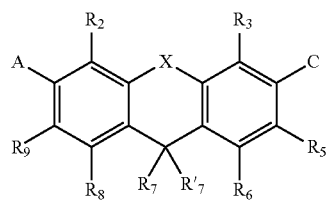

Formula Ib wherein:

X is O, S, or —C(CH$_3$)$_2$—;

A is —OR$_1$ or —NR$_1$R$_{1a}$;

B is =O or =N$^+$R$_4$R$_{4a}$;

C is —OR$_4$ or —NR$_4$R$_{4a}$;

R$_1$, R$_{1a}$, R$_4$, and R$_{4a}$ are each independently H or alkyl, unsubstituted or substituted with -L-SO$_3^-$, -L-PO$_3^{2-}$, a water-soluble polymer, or with -L-R$_x$; or one or more pair of R$_1$ and R$_{1a}$ or R$_4$ and R$_{4a}$ together with the nitrogen to which they are attached form a saturated or unsaturated ring optionally substituted by any of -L-SO$_3^-$, -L-PO$_3^{2-}$ and -L-R$_x$; or at least one of R$_1$, R$_{1a}$, R$_4$, or R$_{4a}$ is an enzyme substrate or a protecting group;

R$_7$ is:

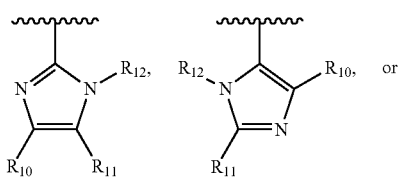

-continued

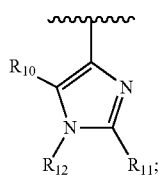

R'$_7$ is H, OH, CN, or C$_1$-C$_6$ alkoxy; or R'$_7$ in combination with R$_7$ forms a 5- or 6-membered spirolactone or spirosultone ring;

R$_2$, R$_3$, R$_5$, R$_6$, R$_8$, R$_9$, R$_{10}$, R$_{11}$, and R$_{12}$ are each independently H, halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, -L-R$_x$; and when R$_7$ is

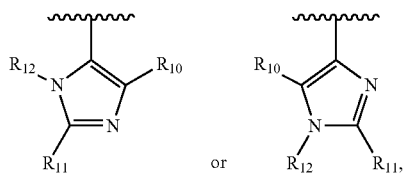

R$_{10}$ is optionally CO$_2^-$; or one or more pair of R$_2$ and R$_{1a}$, R$_3$ and R$_{4a}$, R$_4$ and R$_5$, R$_5$ and R$_6$, R$_8$ and R$_9$, R$_9$ and R$_1$, R$_{10}$ and R$_{11}$, or R$_{11}$ and R$_{12}$ together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$;

R$_x$ is a reactive group;

L is a bond or (Q)$_n$;

each Q is independently NR$_d$, S(O)$_t$, O, C(=X), (C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two NR$_d$ are adjacent and no two O are adjacent;

n is 1-20; and each R$_d$ is H, substituted or unsubstituted alkyl.

In another aspect, the invention provides a compound of formula:

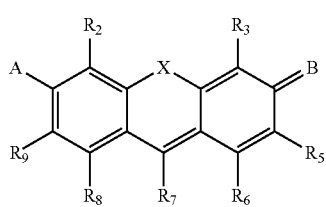

Formula Ia

-continued

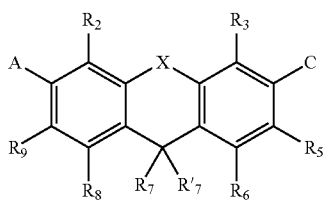

Formula Ib wherein:
X is O, S, or —C(CH$_3$)$_2$—;
A is —OR$_1$ or —NR$_1$R$_{1a}$;
B is =O or =N$^+$R$_4$R$_{4a}$;
C is —OR$_4$ or —NR$_4$R$_{4a}$;
R$_1$, R$_{1a}$, R$_4$, and R$_{4a}$ are each independently H or alkyl, unsubstituted or substituted with -L-SO$_3^-$, -L-PO$_3^{2-}$, a water-soluble polymer, or with -L-R$_x$; or one or more pair of R$_1$ and R$_{1a}$ or R$_4$ and R$_{4a}$ together with the nitrogen to which they are attached form a saturated or unsaturated ring optionally substituted by any of -L-SO$_3^-$, -L-PO$_3^{2-}$ and -L-R$_x$; or at least one of R$_1$, R$_{1a}$, R$_4$, or R$_{4a}$ is an enzyme substrate or a protecting group;
R$_7$ is:

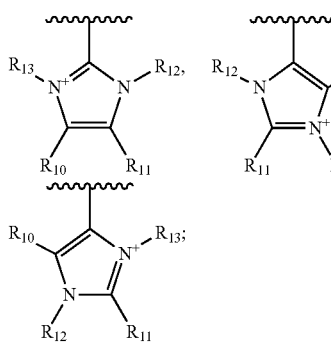

R'$_7$ is H, OH, CN, or C$_1$-C$_6$ alkoxy; or R'$_7$ in combination with R$_7$ forms a 5- or 6-membered spirolactone or spirosultone ring;
R$_2$, R$_3$, R$_5$, R$_6$, R$_8$, R$_9$, R$_{10}$, R$_{11}$, R$_{12}$ and R$_{13}$ are each independently H, halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$; and when R$_7$ is

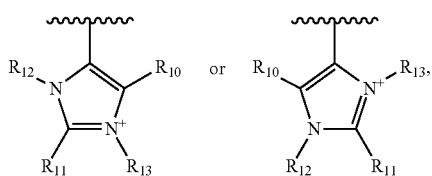

R$_{10}$ is optionally CO$_2^-$; or one or more pair of R$_2$ and R$_{1a}$, R$_3$ and R$_{4a}$, R$_4$ and R$_5$, R$_5$ and R$_6$, R$_8$ and R$_9$, R$_9$ and R$_1$, R$_{10}$ and R$_{11}$, R$_{11}$ and R$_{12}$, R$_{11}$ and R$_{13}$, R$_{10}$ and R$_{12}$, or R$_{10}$ and R$_{13}$ together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$;
R$_x$ is a reactive group;
L is a bond or (Q)$_n$;
each Q is independently NR$_d$, S(O)$_t$, O, C(=X), (C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two NR$_d$ are adjacent and no two O are adjacent;
n is 1-20; and
each R$_d$ is H, substituted or unsubstituted alkyl.
In yet another aspect, the invention provides a compound of formula:

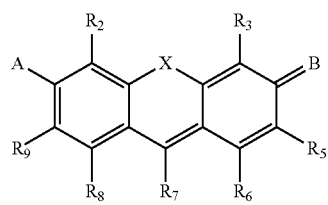

Formula Ia

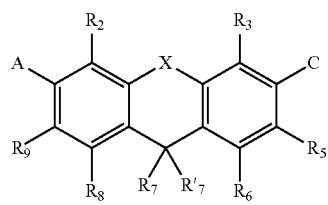

Formula Ib wherein:
X is O, S, or —C(CH$_3$)$_2$—;
A is —OR$_1$ or —NR$_1$R$_{1a}$;
B is =O or =N$^+$R$_4$R$_{4a}$;
C is —OR$_4$ or —NR$_4$R$_{4a}$;
R$_1$, R$_{1a}$, R$_4$, and R$_{4a}$ are each independently H or alkyl, unsubstituted or substituted with -L-SO$_3^-$, -L-PO$_3^{2-}$, a water-soluble polymer, or with -L-R$_x$; and one or more pair of R$_1$ and R$_{1a}$ or R$_4$ and R$_{4a}$ together with the nitrogen to which they are attached form a saturated or unsaturated ring optionally substituted by any of -L-SO$_3^-$, -L-PO$_3^{2-}$ and -L-R$_x$; or at least one of R$_1$, R$_{1a}$, R$_4$, or R$_{4a}$ is an enzyme substrate or a protecting group;
R$_7$ is:

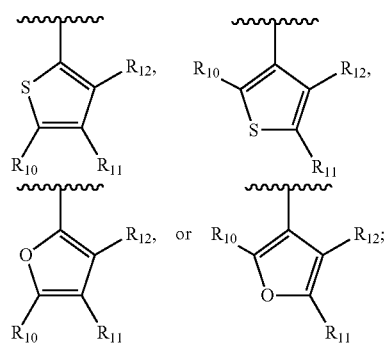

R'$_7$ is H, OH, CN, or C$_1$-C$_6$ alkoxy; or R'$_7$ in combination with R$_7$ forms a 5- or 6-membered spirolactone or spirosultone ring;

R$_2$, R$_3$, R$_5$, R$_6$, R$_8$, R$_9$, R$_{10}$, R$_{11}$, and R$_{12}$ are each independently H, halogen, CN, alkyl, alkenyl, alkoxy, aryl, heteroaryl, -L-PO$_3{}^{2-}$, -L-SO$_3{}^-$, or -L-R$_x$; or one or more pair of R$_2$ and R$_{1a}$, R$_3$ and R$_{4a}$, R$_4$ and R$_5$, R$_5$ and R$_6$, R$_8$ and R$_9$, R$_9$ and R$_1$, R$_{10}$ and R$_{11}$, or R$_{11}$ and R$_{12}$ together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3{}^{2-}$, L-SO$_3{}^-$, or -L-R$_x$;

R$_x$ is a reactive group;

L is a bond or (Q)$_n$;

each Q is independently NR$_d$, S(O)$_t$, O, C(=X), (C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two NR$_d$ are adjacent and no two O are adjacent;

n is 1-20; and each R$_d$ is H, substituted or unsubstituted alkyl.

The invention further provides compounds of formula:

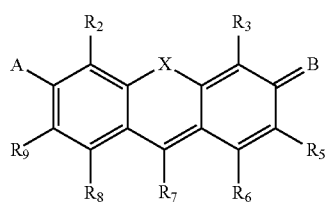

Formula Ia

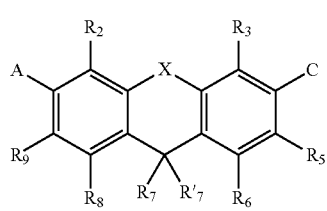

Formula Ib wherein:

X is O, S, or —C(CH$_3$)$_2$—;

A is —OR$_1$ or —NR$_1$R$_{1a}$;

B is =O or =N$^+$R$_4$R$_{4a}$;

C is —OR$_4$ or —NR$_4$R$_{4a}$;

R$_1$, R$_{1a}$, R$_4$, and R$_{4a}$ are each independently H or alkyl, unsubstituted or substituted with -L-SO$_3{}^-$, -L-PO$_3{}^{2-}$, a water-soluble polymer, or with -L-R$_x$; or one or more pair of R$_1$ and R$_{1a}$ or R$_4$ and R$_{4a}$ together with the nitrogen to which they are attached form a saturated or unsaturated ring optionally substituted by any of -L-SO$_3{}^-$, -L-PO$_3{}^{2-}$ and -L-R$_x$; or at least one of R$_1$, R$_{1a}$, R$_4$, or R$_{4a}$ is an enzyme substrate or a protecting group;

R$_7$ is:

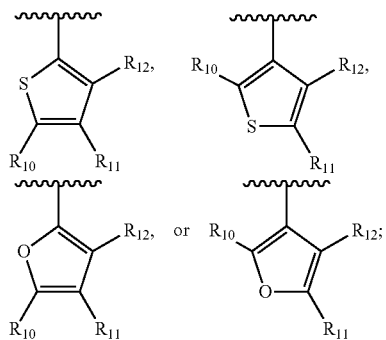

R'$_7$ is H, OH, CN, or C$_1$-C$_6$ alkoxy; or R'$_7$ in combination with R$_7$ forms a 5- or 6-membered spirolactone or spirosultone ring;

R$_2$, R$_3$, R$_5$, R$_6$, R$_8$, R$_9$, R$_{10}$, R$_{11}$, and R$_{12}$ are each independently H, halogen, CN, alkyl, alkenyl, alkoxy, aryl, heteroaryl, -L-PO$_3{}^{2-}$, -L-SO$_3{}^-$, or -L-R$_x$; or one or more pair of R$_2$ and R$_{1a}$, R$_3$ and R$_{4a}$, R$_4$ and R$_5$, R$_5$ and R$_6$, R$_8$ and R$_9$, R$_9$ and R$_1$, R$_{10}$ and R$_{11}$, or R$_{11}$ and R$_{12}$ together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3{}^{2-}$, L-SO$_3{}^-$, or -L-R$_x$;

R$_x$ is a reactive group;

L is a bond or (Q)$_n$;

each Q is independently NR$_d$, S(O)$_t$, O, C(=X), (C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two NR$_d$ are adjacent and no two O are adjacent;

n is 1-20; and each R$_d$ is H, substituted or unsubstituted alkyl; and wherein at least one of R$_2$, R$_3$, R$_5$, R$_6$, R$_8$, R$_9$, R$_{10}$, R$_{11}$, and R$_{12}$ is -L-SO$_3{}^-$.

In still another aspect, the invention provides compounds of formula:

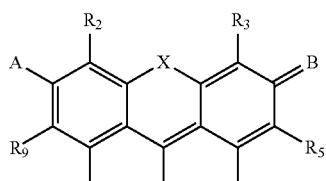

Formula Ia

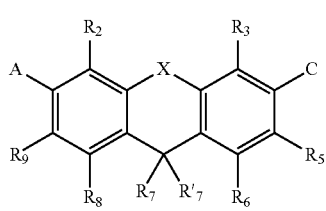

Formula Ib wherein:

X is O, S, or —C(CH$_3$)$_2$—;

A is —OR$_1$ or —NR$_1$R$_{1a}$;

B is =O or =N$^+$R$_4$R$_{4a}$;

C is —OR$_4$ or —NR$_4$R$_{4a}$;

R$_1$, R$_{1a}$, R$_4$, and R$_{4a}$ are each independently H or alkyl, unsubstituted or substituted with -L-SO$_3^-$, -L-PO$_3^{2-}$, a water-soluble polymer, or with -L-R$_x$; or one or more pair of R$_1$ and R$_{1a}$ or R$_4$ and R$_{4a}$ together with the nitrogen to which they are attached form a saturated or unsaturated ring optionally substituted by any of -L-SO$_3^-$, -L-PO$_3^{2-}$ and -L-R$_x$; or at least one of R$_1$, R$_{1a}$, R$_4$, or R$_{4a}$ is an enzyme substrate or a protecting group;

R$_7$ is:

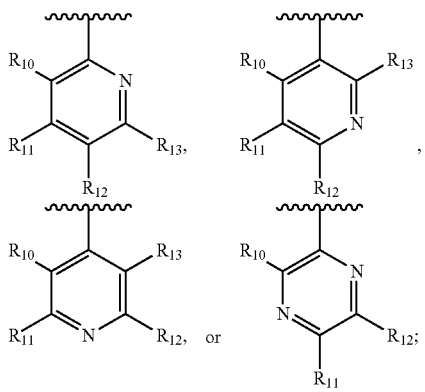

R'$_7$ is H, OH, CN, or C$_1$-C$_6$ alkoxy; or R'$_7$ in combination with R$_7$ forms a 5- or 6-membered spirolactone or spirosultone ring;

R$_2$, R$_3$, R$_5$, R$_6$, R$_8$, R$_9$, R$_{10}$, R$_{11}$, R$_{12}$ and R$_{13}$ are each independently H, halogen, CN, alkyl, alkenyl, alkoxy, aryl, heteroaryl, -L-PO$_3^{2-}$, -L-SO$_3^-$, or -L-R$_x$; and R$_{10}$ or R$_{13}$ are optionally CO$_2^-$; or one or more pair of R$_2$ and R$_{1a}$, R$_3$ and R$_{4a}$, R$_4$ and R$_5$, R$_5$ and R$_6$, R$_8$ and R$_9$, R$_9$ and R$_1$, R$_{10}$ and R$_{11}$, R$_{11}$ and R$_{12}$, or R$_{12}$ and R$_{13}$ together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$;

R$_x$ is a reactive group;

L is a bond or (Q)$_n$;

each Q is independently NR$_d$, S(O)$_t$, O, C(=X), (C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two NR$_d$ are adjacent and no two O are adjacent;

n is 1-20; and each R$_d$ is H, substituted or unsubstituted alkyl; and at least one of R$_2$, R$_3$, R$_5$, R$_6$, R$_8$, R$_9$, R$_{10}$, R$_{11}$, R$_{12}$ and R$_{13}$ is -L-PO$_3^{2-}$, -L-SO$_3^-$, or -L-R$_x$.

The invention also provides compounds of formula:

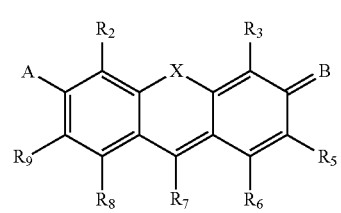

Formula 1a

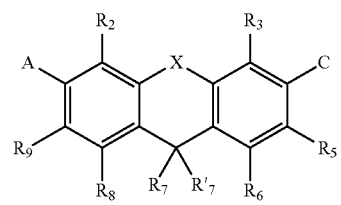

Formula 1b wherein:

X is O, S, or —C(CH$_3$)$_2$—;

A is —OR$_1$ or —NR$_1$R$_{1a}$;

B is =O or =N$^+$R$_4$R$_{4a}$;

C is —OR$_4$ or —NR$_4$R$_{4a}$;

R$_1$, R$_{1a}$, R$_4$, and R$_{4a}$ are each independently H or alkyl, unsubstituted or substituted with -L-SO$_3^-$, -L-PO$_3^{2-}$, a water-soluble polymer, or with -L-R$_x$; or one or more pair of R$_1$ and R$_{1a}$ or R$_4$ and R$_{4a}$ together with the nitrogen to which they are attached form a saturated or unsaturated ring optionally substituted by any of -L-SO$_3^-$, -L-PO$_3^{2-}$ and -L-R$_x$; or at least one of R$_1$, R$_{1a}$, R$_4$, or R$_{4a}$ is an enzyme substrate or a protecting group;

R$_7$ is a 5-10 membered monocyclic or bicyclic heterocycle, unsubstituted or substituted with halogen, CO$_2^-$, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$;

R'$_7$ is H, OH, CN, or C$_1$-C$_6$ alkoxy; or R'$_7$ in combination with R$_7$ forms a 5- or 6-membered spirolactone or spirosultone ring;

R$_2$, R$_3$, R$_5$, R$_6$, R$_8$, R$_9$, are each independently H, halogen, CN, alkyl, alkenyl, alkoxy, aryl, heteroaryl, -L-PO$_3^{2-}$, -L-SO$_3^-$, or -L-R$_x$; or one or more pair of R$_2$ and R$_{1a}$, R$_3$ and R$_{4a}$, R$_4$ and R$_5$, R$_5$ and R$_6$, R$_8$ and R$_9$, or R$_9$ and R$_1$, together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$;

R$_x$ is a reactive group;

L is a bond or (Q)$_n$;

each Q is independently NR$_d$, S(O)$_t$, O, C(=X), (C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two NR$_d$ are adjacent and no two O are adjacent;

n is 1-20;

each R$_d$ is H, substituted or unsubstituted alkyl; and at least one of R$_2$, R$_3$, R$_5$, R$_6$, R$_8$, or R$_9$ is -L-SO$_3^-$.

The invention also provides compounds of formula:

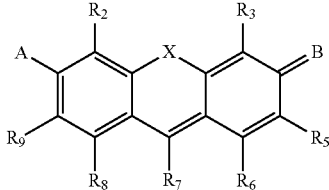

Formula 1a

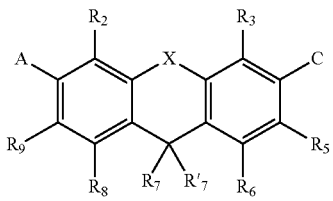

Formula 1b wherein:
X is O, S, or —C(CH$_3$)$_2$—;
A is —OR$_1$ or —NR$_1$R$_{1a}$;
B is =O or =N$^+$R$_4$R$_{4a}$;
C is —OR$_4$ or —NR$_4$R$_{4a}$;
R$_1$, R$_{1a}$, R$_4$, and R$_{4a}$ are each independently H or alkyl, unsubstituted or substituted with -L-SO$_3$$^-$, -L-PO$_3$$^{2-}$, a water-soluble polymer, or with -L-R$_x$; or one or more pair of R$_1$ and R$_{1a}$ or R$_4$ and R$_{4a}$ together with the nitrogen to which they are attached form a saturated or unsaturated ring optionally substituted by any of -L-SO$_3$$^-$, -L-PO$_3$$^{2-}$ and -L-R$_x$; or at least one of R$_1$, R$_{1a}$, R$_4$, or R$_{4a}$ is an enzyme substrate or a protecting group;
R$_7$ is a 5-membered monocyclic heteroaryl group, substituted with -L-R$_x$, and optionally further substituted with halogen, CO$_2$$^-$, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3$$^{2-}$, L-SO$_3$$^-$, or -L-R$_x$;
R'$_7$ is H, OH, CN, or C$_1$-C$_6$ alkoxy; or R'$_7$ in combination with R$_7$ forms a 5- or 6-membered spirolactone or spirosultone ring;
R$_2$, R$_3$, R$_5$, R$_6$, R$_8$, R$_9$, are each independently H, halogen, CN, alkyl, alkenyl, alkoxy, aryl, heteroaryl, -L-PO$_3$$^{2-}$, -L-SO$_3$$^-$, or -L-R$_x$; or one or more pair of R$_2$ and R$_{1a}$, R$_3$ and R$_{4a}$, R$_4$ and R$_5$, R$_5$ and R$_6$, R$_8$ and R$_9$, or R$_9$ and R$_1$, together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3$$^{2-}$, L-SO$_3$$^-$, or -L-R$_x$;
R$_x$ is a reactive group;
L is a bond or (Q)$_n$;
each Q is independently NR$_d$, S(O)$_t$, O, C(=X), (C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two NR$_d$ are adjacent and no two O are adjacent;
n is 1-20;
each R$_d$ is H, substituted or unsubstituted alkyl; and at least one or more pair of R$_2$ and R$_{1a}$, R$_3$ and R$_{4a}$, R$_4$ and R$_5$, R$_5$ and R$_6$, R$_8$ and R$_9$, or R$_9$ and R$_1$, together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3$$^{2-}$, L-SO$_3$$^-$, or -L-R$_x$.

The invention also provides compounds of formula:

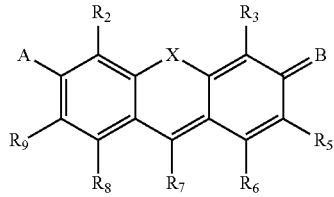

Formula 1a

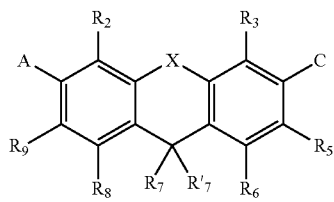

Formula 1b wherein:
X is O, S, or —C(CH$_3$)$_2$—;
A is —OR$_1$ or —NR$_1$R$_{1a}$;
B is =O or =N$^+$R$_4$R$_{4a}$;
C is —OR$_4$ or —NR$_4$R$_{4a}$;
R$_1$, R$_{1a}$, R$_4$, and R$_{4a}$ are each independently H or alkyl, unsubstituted or substituted with -L-SO$_3$$^-$, -L-PO$_3$$^{2-}$, a water-soluble polymer, or with -L-R$_x$; or one or more pair of R$_1$ and R$_{1a}$ or R$_4$ and R$_{4a}$ together with the nitrogen to which they are attached form a saturated or unsaturated ring optionally substituted by any of -L-SO$_3$$^-$, -L-PO$_3$$^{2-}$ and -L-R$_x$; or at least one of R$_1$, R$_{1a}$, R$_4$, or R$_{4a}$ is an enzyme substrate or a protecting group;
R$_7$ is a 5-10 membered monocyclic or bicyclic heterocycle comprising at least one quaternary nitrogen atom, unsubstituted or substituted with halogen, CO$_2$$^-$, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3$$^{2-}$, L-SO$_3$$^-$, or -L-R$_x$;
R'$_7$ is H, OH, CN, or C$_1$-C$_6$ alkoxy; or R'$_7$ in combination with R$_7$ forms a 5- or 6-membered spirolactone or spirosultone ring;
R$_2$, R$_3$, R$_5$, R$_6$, R$_8$, R$_9$, are each independently H, halogen, CN, alkyl, alkenyl, alkoxy, aryl, heteroaryl, -L-PO$_3$$^{2-}$, -L-SO$_3$$^-$, or -L-R$_x$; or one or more pair of R$_2$ and R$_{1a}$, R$_3$ and R$_{4a}$, R$_4$ and R$_5$, R$_5$ and R$_6$, R$_8$ and R$_9$, or R$_9$ and R$_1$, together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3$$^{2-}$, L-SO$_3$$^-$, or -L-R$_x$;
R$_x$ is a reactive group;
L is a bond or (Q)$_n$;

each Q is independently NR$_d$, S(O)$_t$, O, C(=X), (C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two NR$_d$ are adjacent and no two O are adjacent; n is 1-20; and each R$_d$ is H, substituted or unsubstituted alkyl.

In another aspect, the invention provides compounds of Formula 1a or 1b:

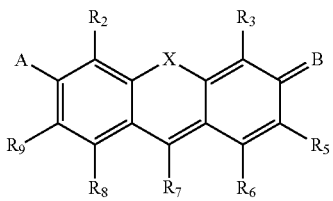

Formula 1a

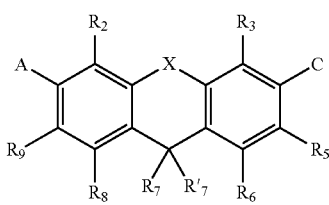

Formula 1b wherein:
X is O, S, or —C(CH$_3$)$_2$—;
A is —OR$_1$ or —NR$_1$R$_{1a}$;
B is =O or =N$^+$R$_4$R$_{4a}$;
C is —OR$_4$ or —NR$_4$R$_{4a}$;
R$_1$, R$_{1a}$, R$_4$, and R$_{4a}$ are each independently H or alkyl, unsubstituted or substituted with -L-SO$_3^-$, -L-PO$_3^{2-}$, a water-soluble polymer, or with -L-R$_x$; or one or more pair of R$_1$ and R$_{1a}$ or R$_4$ and R$_{4a}$ together with the nitrogen to which they are attached form a saturated or unsaturated ring optionally substituted by any of -L-SO$_3^-$, -L-PO$_3^{2-}$ and -L-R$_x$; or at least one of R$_1$, R$_{1a}$, R$_4$, or R$_{4a}$ is an enzyme substrate or a protecting group;
R$_7$ is:

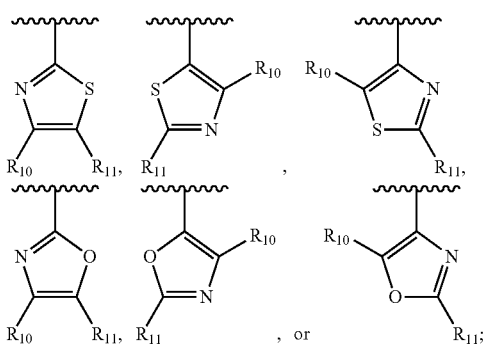

R'$_7$ is H, OH, CN, or C$_1$-C$_6$ alkoxy; or R'$_7$ in combination with R$_7$ forms a 5- or 6-membered spirolactone or spirosultone ring;
R$_2$, R$_3$, R$_5$, R$_6$, R$_8$, R$_9$, R$_{10}$, and R$_{11}$ are each independently H, halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl aminosulfonyl, aryl heteroaryl, -L-PO$_3^{2-}$, L-SO$_3^-$, -L-R$_x$; and when R$_7$ is

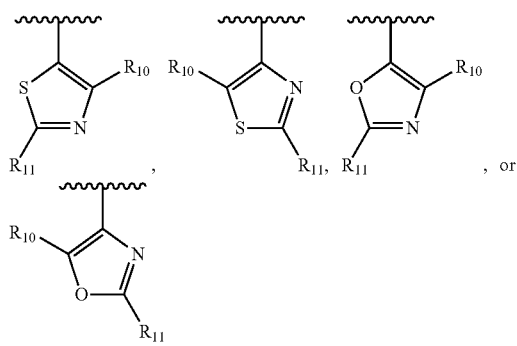

R$_{10}$ is optionally CO$_2^-$; or one or more pair of R$_2$ and R$_{1a}$, R$_3$ and R$_{4a}$, R$_4$ and R$_5$, R$_5$ and R$_6$, R$_8$ and R$_9$, R$_9$ and R$_1$, or R$_{10}$ and R$_{11}$ together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$;
R$_x$ is a reactive group;
L is a bond or (Q)$_n$;
each Q is independently NR$_d$, S(O)$_t$, O, C(=X), (C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two NR$_d$ are adjacent and no two O are adjacent;
n is 1-20; and
each R$_d$ is H, substituted or unsubstituted alkyl.

The invention also provides compounds of Formula 1a or 1b:

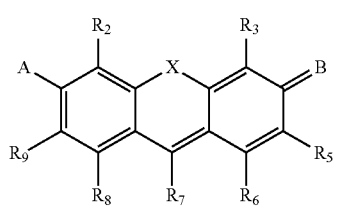

Formula 1a

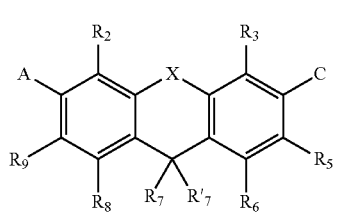

Formula 1b wherein:
X is O, S, or —C(CH$_3$)$_2$—;
A is —OR$_1$ or —NR$_1$R$_{1a}$;
B is =O or =N$^+$R$_4$R$_{4a}$;
C is —OR$_4$ or —NR$_4$R$_{4a}$;

$R_1$, $R_{1a}$, $R_4$, and $R_{4a}$ are each independently H or alkyl, unsubstituted or substituted with -L-SO$_3^-$, -L-PO$_3^{2-}$, a water-soluble polymer, or with -L-R$_x$; or one or more pair of $R_1$ and $R_{1a}$ or $R_4$ and $R_{4a}$ together with the nitrogen to which they are attached form a saturated or unsaturated ring optionally substituted by any of -L-SO$_3^-$, -L-PO$_3^{2-}$ and -L-R$_x$; or at least one of $R_1$, $R_{1a}$, $R_4$, or $R_{4a}$ is an enzyme substrate or a protecting group;

$R_7$ is:

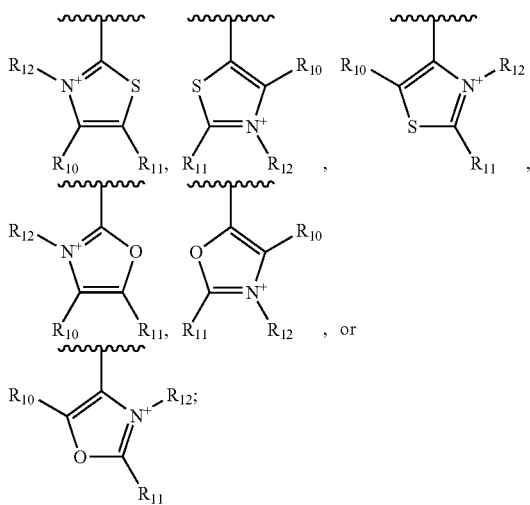

$R'_7$ is H, OH, CN, or $C_1$-$C_6$ alkoxy; or $R'_7$ in combination with $R_7$ forms a 5- or 6-membered spirolactone or spirosultone ring;

$R_2$, $R_3$, $R_5$, $R_6$, $R_8$, $R_9$, $R_{10}$, $R_{11}$, and $R_{12}$ are each independently H, halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, -L-R$_x$; and when $R_7$ is

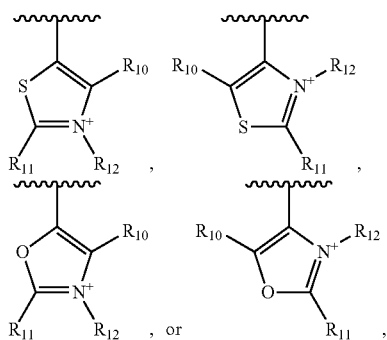

$R_{10}$ is optionally CO$_2^-$, or when $R_7$ is

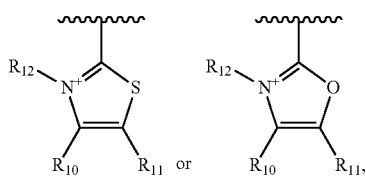

$R_{12}$ is CO$^{2-}$; or one or more pair of $R_2$ and $R_{1a}$, $R_3$ and $R_{4a}$, $R_4$ and $R_5$, $R_5$ and $R_6$, $R_8$ and $R_9$, $R_9$ and $R_1$, $R_{10}$ and $R_{11}$, $R_{10}$ and $R_{12}$ or $R_{11}$ and $R_{12}$ together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$;

R$_x$ is a reactive group;

L is a bond or (Q)$_n$;

each Q is independently NR$_d$, S(O)$_t$, O, C(=X), (C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two NR$_d$ are adjacent and no two O are adjacent;

n is 1-20; and each R$_d$ is H, substituted or unsubstituted alkyl.

In some embodiments of the compounds of the invention, X is O. In other embodiments, X is S. In still other embodiments, X is —C(CH$_3$)$_2$—.

In some embodiments of the compounds of the invention, A is —OR$_1$. In other embodiments, A is —NR$_1$R$_{1a}$.

$R_1$ and $R_{1a}$ include, for example, H and -L-alkyl, unsubstituted or substituted with -L-SO$_3^-$, -L-PO$_3^{2-}$, a water-soluble polymer, or with -L-R$_x$. In one embodiment, A is —OH. In another embodiment, A is —OR$_1$ and $R_1$ is (C=O)C$_1$-C$_{10}$ alkyl.

In another embodiment, $R_1$ and $R_{1a}$ together with the nitrogen to which they are attached form a saturated or unsaturated ring optionally substituted by any of -L-SO$_3^-$, -L-PO$_3^{2-}$ and -L-R$_x$.

In one embodiment, at least one of $R_1$ and $R_{1a}$ is an enzyme substrate or a protecting group. For example, $R_1$ or $R_{1a}$ is a peptide which is an enzyme substrate. Alternatively, $R_1$ or $R_{1a}$ is a carbohydrate which is an enzyme substrate. In another embodiment, $R_1$ or $R_{1a}$ is a compound comprising an ester linkage which is an enzyme substrate.

In some embodiments of the compounds of the invention, B is =O. In other embodiments, B is =N$^+$R$_4$R$_{4a}$.

$R_4$ and $R_{4a}$ include, for example, H and -L-alkyl, unsubstituted or substituted with -L-SO$_3^-$, -L-PO$_3^{2-}$, a water-soluble polymer, or with -L-R$_x$. In one embodiment, B is =NH$_2^+$. In another embodiment, $R_4$ and $R_{4a}$ together with the nitrogen to which they are attached form a saturated or unsaturated ring optionally substituted by any of -L-SO$_3^-$, -L-PO$_3^{2-}$ and -L-R$_x$. For example, $R_4$ and $R_{4a}$ together with the nitrogen to which they are attached form a saturated 6-membered ring.

In some embodiments, $R_2$, $R_3$, $R_5$, $R_6$, $R_8$ and $R_9$ are each independently H, halogen, CN, alkyl, alkenyl, alkoxy, aryl, heteroaryl, -L-PO$_3^{2-}$, -L-SO$_3^-$, or -L-R$_x$; or one or more pair of $R_2$ and $R_{1a}$, $R_3$ and $R_{4a}$, $R_4$ and $R_5$, $R_5$ and $R_6$, $R_8$ and $R_9$, or $R_9$ and $R_1$ together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$.

In some embodiments, $R_1$ and $R_9$ taken together with the atoms to which they are attached form one or more fused rings. For example, $R_1$ and $R_9$ taken together form one of the rings shown below:

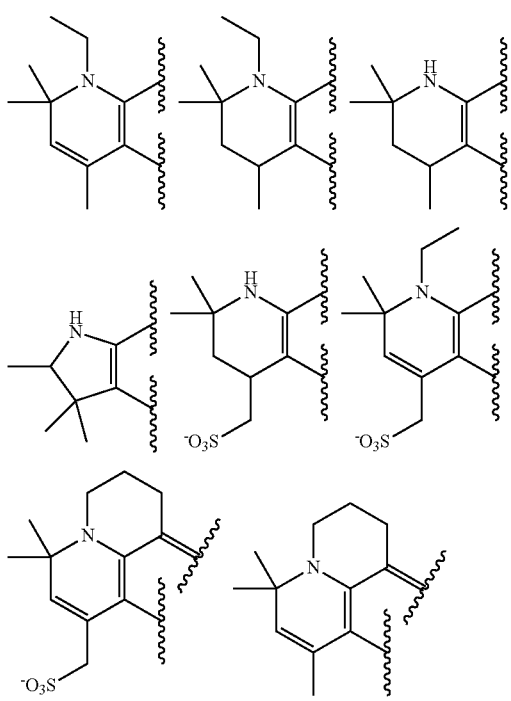

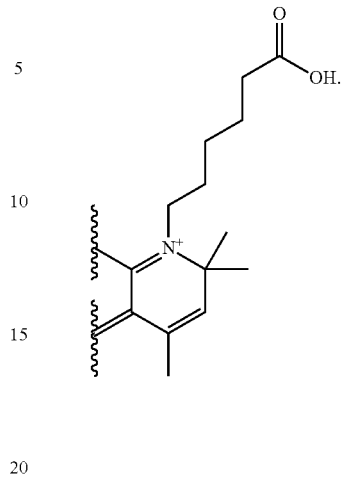

When the compound of the invention is of formula 1b, R'$_7$ is H or a substituent of the group R$_7$, wherein R'$_7$ together with R$_7$ and the carbon atom they are attached to in the xanthenes ring form a 5- or 6-membered spirolactone or spirosultone ring. Two examples are shown below (additional substituents are not shown for simplicity):

In some embodiments, R$_4$ and R$_5$ taken together with the atoms to which they are attached form one or more fused rings. For example, R$_4$ and R$_5$ taken together form one of the rings shown below:

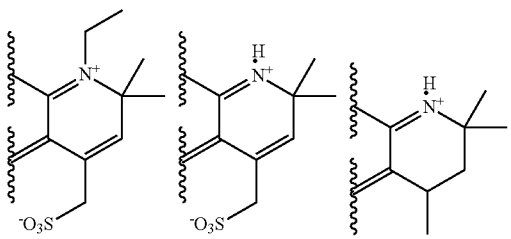

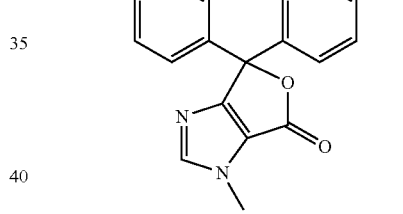

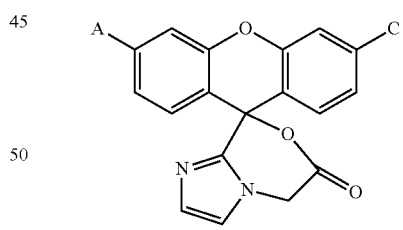

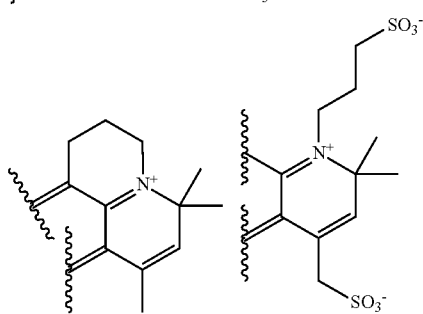

In general, when R'$_7$ is H, the dye is a dihydroxanthene dye, which is a reduced form of a xanthene dye. In some embodiments of compounds of the invention, where R$_7$ comprises a carboxylate group (—CO$_2$$^-$) or sulfonate group (—SO$_3$$^-$) ortho to the bond connecting R$_7$ and the xanthene ring, the compound may exist as a stable spirolactone form or a stable spirosultone form as shown above, or exist as a mixture in equilibrium of the spirolactone form or spirosultone form and a xanthene form where the lactone or sultone ring is open as shown by the example below:

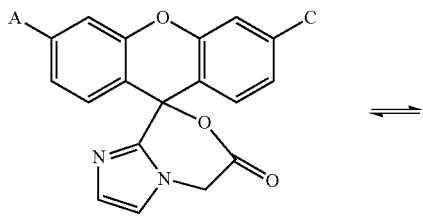
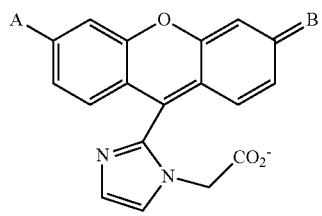

Such an equilibrium between the two forms of xanthenes dyes is common for a number of existing fluorescein and rhodamine dyes. The spirolactone or spirosultone may be the preferred form in hydrophobic environments.

In the compounds of the invention, $R_7$ is a 5-10 membered monocyclic or bicyclic heterocyclic substitutent. In some embodiments, $R_7$ is unsubstituted. In other embodiments, $R_7$ is substituted with halogen, $CO_2^-$, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-$PO_3^{2-}$, L-$SO_3^-$, or -L-$R_x$. In some embodiments, $R_7$ is substituted with at least one alkyl. In other embodiments, $R_7$ is substituted with at least one -L-$R_x$ group. In still other embodiments, $R_7$ is substituted with at least one L-$SO_3^-$ group.

In some embodiments, of the invention, $R_7$ is one of the heteroaryl moieties shown below:

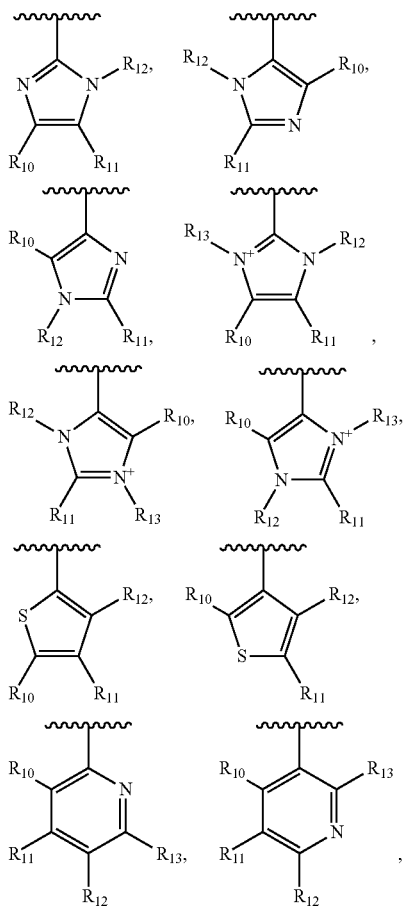

-continued

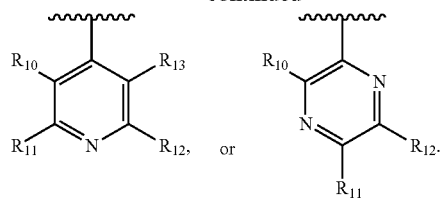

$R_{10}$, $R_{11}$, $R_{12}$ and $R_{13}$ are H, halogen, $CO_2^-$, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-$PO_3^{2-}$, L-$SO_3^-$, or -L-$R_x$. In some embodiments, at least one of $R_{10}$, $R_{11}$, $R_{12}$ and $R_{13}$ is alkyl. In other embodiments, at least one of $R_{10}$, $R_{11}$, $R_{12}$ and $R_{13}$ is -L-$SO_3^-$. In still other embodiments, at least one of $R_{10}$, $R_{11}$, $R_{12}$ and $R_{13}$ is -L-$R_x$. In other embodiments, two substitutents chosen from $R_{10}$, $R_{11}$, $R_{12}$ and $R_{13}$ taken together form a fused aromatic or heteroaromatic ring, which is unsubstituted or further substituted by one or more halogen, $CO_2^-$, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-$PO_3^{2-}$, L-$SO_3^-$, or -L-$R_x$.

In some embodiments, $R_7$ is one of the moieties shown below:

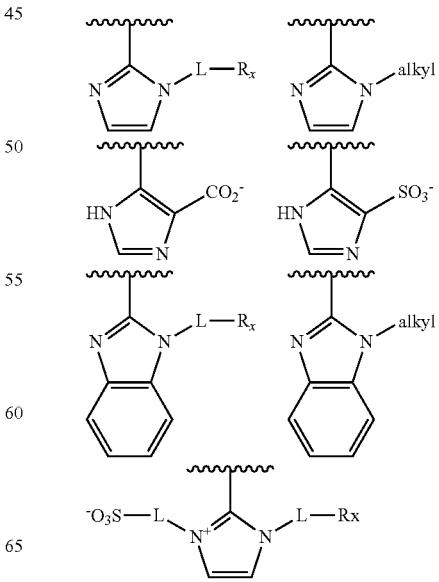

-continued

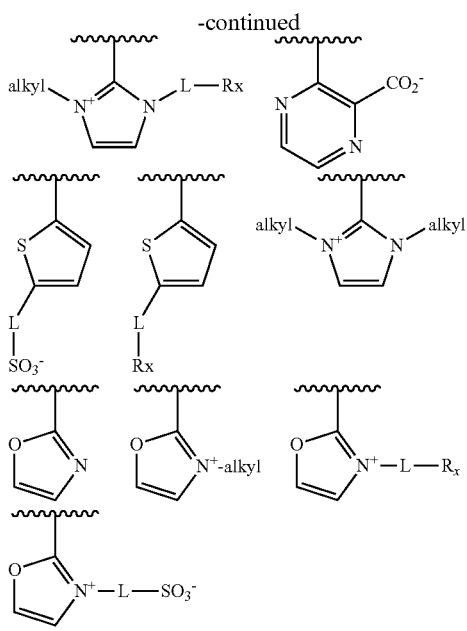

In some embodiments, the compounds of the invention are substituted with at least one substituent which is an enzyme substrate or a protecting group. Such groups can be attached to either the hydroxyl (—OH) or a primary or secondary amine. In some embodiments, when A or C or both A and C are —OH or —NH$_2$, A and C may be protected by a protecting group. Various schemes for amino or hydroxyl group protection are known. In some instances, the protection is carried out such that the amino or hydroxyl group is chemically compatible with another chemical moiety present on the same molecule, such as a reactive group. This protection allows the reactive group to react with its reaction partner without chemically changing the protected hydroxyl or amine. For example, if the dye molecule comprises a phosphoramidite reactive group, the two hydroxyl groups of the dye can be protected as pivaloyl esters. When the phosphoramidite reactive group reacts with a reaction partner on an oligonucleotide, resulting in a fluorescently labeled oligonucleotide, protection of the hydroxyl groups is necessary because the phosphoramidite group is not compatible with free hydroxyl groups on the same dye molecule. Once the phosphoramidite group has with the oligonucleotide to form a covalent linkage, the protecting groups can then be easily removed under acidic conditions.

In other embodiments, at least one of $R_1$, $R_{1a}$, $R_4$ and $R_{4a}$ is an enzyme substrate which is susceptible to cleavage by an enzyme which recognizes the substrate moiety. The cleavable bond is, for example, between O and $R_1$ in an —O$R_1$ moiety or between —NH and $R_1$ in the case of —NH$R_1$, resulting in the release of the hydroxyl or amino group(s). In general, when A or C or both A and C comprise an enzyme substrate moiety, the dye is only weakly fluorescent or, more frequently, nonfluorescent. Enzymatic cleavage of the substrate moiety or moieties regenerates the hydroxyl or amino group of the dye, leading to a fluorescence signal increase. In some cases, the site of enzyme action may not be between —O and the enzyme substrate, or between —NH and the enzyme substrate, but rather within the substrate moiety. For example, an enzyme may reduce, oxidize or hydrolyze a bond within the enzyme substrate, which then leads to cleavage of the bond between —O (or —NH) and the enzyme substrate. The invention therefore provides a method of detecting the activity of an enzyme by measuring increased fluorescence resulting from the activity of the enzyme. Methods for constructing various fluorogenic or chromogenic enzyme substrates from a hydroxyl- or amine-containing dye are known. For example, dyes comprising a hydroxyl group (as A, B, or C groups) can be used for preparing a substrate for phosphotase, beta-galactosidase, esterase, lipase, de-alkylase, merely by way of example. Likewise, dyes comprising an amine (as A, B or C groups) can be used for preparing substrates for various peptidases. Peptidase substrates based on rhodamine 110 are widely commercially available, and methods used for preparing fluorescein- or rhodamine 110-based enzyme substrates are fully applicable to the present invention.

In general, linking moieties (e.g. L, Q) may be any group connecting two moieties, such as fluorophores, sulfonamide groups and/or reactive groups to each other or to any other group included in the compound of the invention. Synthetic accessibility and convenience may generally dictate the nature of each linking moiety. In some embodiments, a linking moiety is a group containing about 1-100 atoms and formed of one or more chemical bonds selected such that the group is a stable moiety. In other embodiments, a linking moiety is formed of one or more carbon-hydrogen, carbon-nitrogen, carbon-oxygen, carbon-sulfur, carbon-phosphorus, nitrogen-hydrogen, sulfur-hydrogen, phosphorus-hydrogen, sulfur-oxygen, sulfur-nitrogen, sulfur-phosphorus, phosphorus-oxygen, phosphorus-nitrogen and oxygen-nitrogen bonds, wherein such bonds may be single, double, triple, aromatic and heteroaromatic bonds selected such that the linking moiety is stable. A linking moiety can be, for example, a divalent alkyl radical. Alternatively, a linking moiety may be an alkyl group comprising additional ether, amine, amide, ester, sulfonyl, thioether, carboxamide, sulfonamide, hydrazide or morpholino, aryl and heteroaryl groups.

Linking moieties are generally formed of about 1-100 atoms. In some embodiments, linking moieties are formed of 1-50 non-hydrogen atoms as well as additional hydrogen atoms. Such atoms may be, for example, C, N, O, P or S. In other embodiments, a linker moiety connecting two groups comprises 1 to 50 consecutive bonds between the groups. Some linker moieties may have 1 to 40, 1 to 30, 1 to 20, 1 to 10, 1 to 5, 5 to 25, or 5 to 20 such consecutive bonds.

Non-limiting exemplary linking moieties are illustrated below:

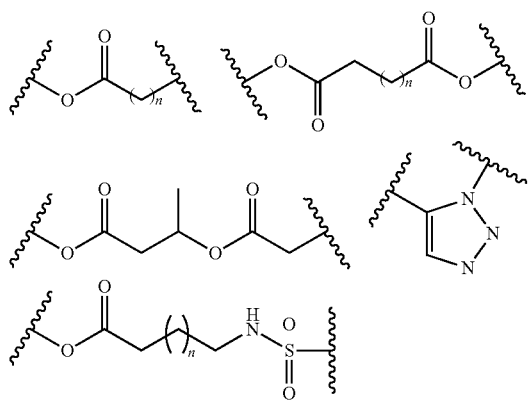

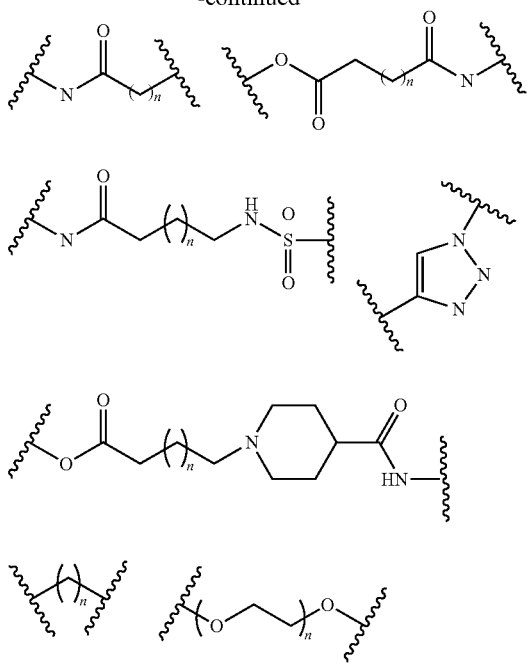

In the above image, n represents a number of repeating methylene units which can be varied such as to provide a desired length of the linker. Typically, n ranges from 1 to about 50. Some linkers will have an n of 1 to 40, 1 to 30, 1 to 20, 1 to 10, 1 to 5, 5 to 30, 5 to 20, or 5 to 15.

In some embodiments, L is a bond or has the formula $(Q)_n$, where each Q is independently $NR_d$, $S(O)_t$, O, C(=X), (C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two $NR_d$ are adjacent and no two O are adjacent. In such embodiments, n is 1-20, and each $R_d$ is H or substituted or unsubstituted alkyl.

In some cases, the L of an -L-$R_x$ group is a polymethylene —$(CH_2)$—, where n is from 1 to about 6. In other cases, the L of an -L-$R_x$ group may comprise a water-soluble moiety, such as a polyethylene glycol (or PEG) unit, where the number of ethylene glycol unit may be from 1 to about 30, for example. More typically, the number of ethylene glycol unit is from 1 to about 24. In some cases, the L of -L-$R_x$ comprises a PEG moiety of 8 ethylene glycol units. In other cases, the PEG moiety comprises 12 ethylene units. The PEG moiety may be useful for increasing the water solubility of the dye and in some cases increases the fluorescence brightness of the dye when conjugated to a polymer, such as a protein or polynucleic acid.

Some but not all of compounds of the invention may comprise at least one reactive group $R_x$. A reactive group is a chemical moiety capable of reacting with a reaction partner on a substrate or substrate molecule to form a covalent bond. A compound of the invention can be used to label a wide variety of molecules or substrates that contain a suitable reaction partner or are derivatized to contain a suitable reaction partner. "Reactive group" and "reaction partner" may refer to groups on a compound of the present invention, or to groups on a molecule to be labeled. Here, by way of convenience, but not limitation, a bond-forming group on a compound will generally be referred to as a reactive group and a bond-forming group on the substrate molecule will generally be referred to as a reaction partner.

In any of the structural formulas shown herein, "$R_x$" may be any reactive group that confers a desirable functional property to the compound of the invention. The reactive group and its reaction partner may be an electrophile and a nucleophile, respectively, that can form a covalent bond with or without a coupling agent or catalyst. According to one embodiment, the reactive group is a photoactivatable group capable of reacting with a hydrocarbon molecule upon ultraviolet photoactivation or photolysis. According to another embodiment, the reactive group is a dienophile capable of reacting with a conjugated diene via a Diels-Alder reaction. According to yet another embodiment, the reactive group is a 1,3-diene capable of reacting with a dienophile. According to still another embodiment, the reactive group is an alkyne capable of reacting with an azido functional group to form a 1,2,3-triazole linkage. According to still another embodiment, the reactive group is a 2-(diphenylphosphino)benzoic acid methyl ester capable of reacting with an azido functional group to form an amide linkage via so-called Staudinger reaction. Merely by way of example, examples of useful reactive groups, functional groups, and corresponding linkages according to the present invention are listed below in Table 1.

TABLE 1

Examples of Reactive Groups, Functional Groups, and Covalent Linkages

| Reactive Group | Reaction Partner/Substrate | Resulting Covalent Linkage |
| --- | --- | --- |
| activated esters* | amines/anilines | Carboxamides |
| acrylamides | Thiols | Thioethers |
| acyl azides** | amines/anilines | Carboxamides |
| acyl halides | amines/anilines | Carboxamides |
| acyl halides | Alcohols/phenols | Esters |
| acyl nitriles | Alcohols/phenols | Esters |
| acyl nitriles | amines/anilines | Carboxamides |
| aldehydes | amines/anilines | Imines |
| aldehydes or ketones | Hydrazines | Hydrazones |
| aldehydes or ketones | Hydroxylamines | Oximes |
| alkyl halides | amines/anilines | alkyl amines |
| alkyl halides | Thiols | Thioethers |
| alkyl halides | alcohols/phenols | Esters |
| alkyl sulfonates | Thiols | Thioethers |
| alkyl sulfonates | carboxylic acids | Esters |
| alkyl sulfonates | alcohols/phenols | Esters |
| anhydrides | alcohols/phenols | Esters |
| anhydrides | amines/anilines | Carboxamides |
| aryl halides | Thiols | Thiophenols |
| aryl halides | Amines | aryl amines |
| aziridines | Thiols | Thioethers |
| boronates | Glycols | boronate esters |
| epoxides | Thiols | Thioethers |
| haloacetamides | Thiols | Thioethers |
| halotriazines | amines/anilines | Aminotrizaines |
| halotriazines | alcohols/phenols | triazinyl ethers |
| imido esters | amines/anilines | Amidines |
| isocyanates | amines/anilines | Ureas |
| isocyanates | alcohols/phenols | Urethanes |
| isothiocyanates | amines/anilines | Thioureas |
| maleimides | Thiols | Thioethers |
| phosphoramidites | Alcohols | phosphite esters |
| silyl halides | Alcohols | silyl ethers |
| sulfonate esters | amines/anilines | alkyl amines |
| sulfonate esters | Thiols | Thioethers |
| sulfonate esters | Alcohols | Ethers |
| sulfonyl halides | amines/anilines | Sulfonamides |

TABLE 1-continued

Examples of Reactive Groups, Functional Groups, and Covalent Linkages

| Reactive Group | Reaction Partner/Substrate | Resulting Covalent Linkage |
| --- | --- | --- |
| sulfonyl halides | phenols/alcohols | sulfonate esters |
| azide | alkyne | 1,2,3-triazole |
| Cis-platinum | guanosine | Platinum-guanosine complex |

*Activated esters, as understood in the art, generally have the formula —COΩ, where Ω is a good leaving group, such as succinimidyloxy (—OC$_4$H$_4$O$_2$), sulfosuccinimidyloxy (—OC$_4$H$_3$O$_2$—SO$_3$H), or -1-oxybenzotriazolyl (—OC$_6$H$_4$N$_3$), for example; or an aryloxy group or aryloxy substituted one or more times by electron-withdrawing substituent(s), such as nitro, fluoro, chloro, cyano, trifluoromethyl, or combinations thereof, for example, used to form activated aryl esters; or a carboxylic acid activated by a carbodiimide to form an anhydride or mixed anhydride —OCOR$^a$ or —OCNR$^a$NHR$^b$, where R$^a$ and R$^b$, which may be the same or different, are independently C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl.
**Acyl azides can also rearrange to isocyanates.

The reactive group may be one that will react with an amine, a thiol, a hydroxyl or an aldehyde. The reactive group may be an amine-reactive group, such as a succinimidyl ester (SE), for example, or a thiol-reactive group, such as a maleimide, a haloacetamide, or a methanethiosulfonate (MTS), for example, or an aldehyde-reactive group, such as an amine, an aminooxy, or a hydrazide, for example.

Choice of the reactive group used to attach the fluorophore to the substance to be conjugated typically depends on the functional group on the substance to be conjugated and the type or length of covalent linkage desired. The types of functional groups typically present on the organic or inorganic substances include, but are not limited to, amines, thiols, alcohols, phenols, aldehydes, ketones, phosphates, imidazoles, hydrazines, hydroxylamines, disubstituted amines, halides, epoxides, sulfonate esters, purines, pyrimidines, carboxylic acids, or a combination of these groups. A single type of reactive site may be available on the substance (typical for polysaccharides), or a variety of sites may occur (e.g. amines, thiols, alcohols, phenols), as is typical for proteins. A conjugated substance may be conjugated to more than one fluorophore, which may be the same or different, or to a substance that is additionally modified by a hapten, such as biotin. Although some selectivity can be obtained by careful control of the reaction conditions, selectivity of labeling is best obtained by selection of an appropriate reactive dye.

In some embodiments, $R_x$ will react with an amine, a thiol, an alcohol, an aldehyde or a ketone. In one embodiment, $R_x$ is an acrylamide, an activated ester of a carboxylic acid, an acyl azide, an acyl nitrile, an aldehyde, an alkyl halide, an amine, an anhydride, an aniline, an aryl halide, an azide, an aziridine, a boronate, a carboxylic acid, a diazoalkane, a haloacetamide, a halotriazine, a hydrazine (including hydrazides), an imido ester, an isocyanate, an isothiocyanate, a maleimide, a phosphoramidite, a sulfonyl halide, or a thiol group. In other embodiments, $R_x$ is a carboxylic acid, a succinimidyl ester, an azidoperfluorobenzamido group, a pyrrole-2,5-dione, a tetrafluorophenol ester, an imido ester, an azidonitrophenyl, an alkyne, a 3-(2-pyridyl dithio)-propionamide, a glyoxal or an aldehyde. Where the reactive group is a photoactivatable group, such as an azide, diazirinyl or azidoaryl derivative, the dye becomes chemically reactive only after illumination with light of an appropriate wavelength. Where $R_x$ is a succinimidyl ester of a carboxylic acid, the reactive dye is particularly useful for preparing dye-conjugates of proteins or oligonucleotides. Where $R_x$ is a maleimide, the reactive dye is particularly useful for conjugation to thiol-containing substances. Where $R_x$ is a hydrazide, the reactive dye is particularly useful for conjugation to periodate-oxidized carbohydrates and glycoproteins, and in addition is an aldehyde-fixable polar tracer for cell microinjection.

Exemplary compounds of the invention along with their known fluorescence properties are shown in Table 2:

TABLE 2

Exemplary compounds of the invention are shown. For simplicity, counter ions are not shown in some cases. Absorption/Emission spectra were measured in PBS unless otherwise indicated.

| Compound No. | Structure | Absorption/Emission Wavelengths (nm) |
| --- | --- | --- |
| 1 | 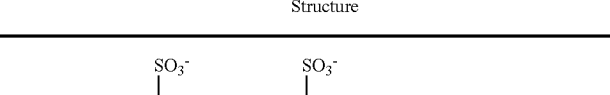 | 548/571 |

TABLE 2-continued
Exemplary compounds of the invention are shown. For simplicity, counter ions are not shown in some cases. Absorption/Emission spectra were measured in PBS unless otherwise indicated.
| Compound No. | Structure | Absorption/Emission Wavelengths (nm) |
|---|---|---|
| 2 | 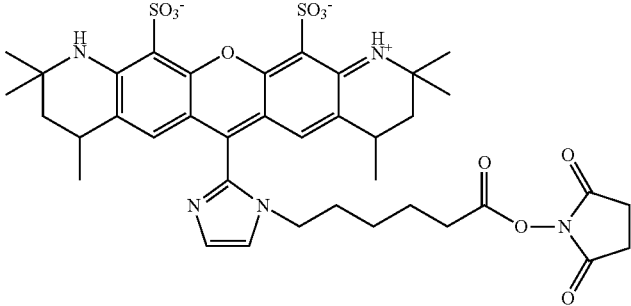 | 559/579 |
| 3 | 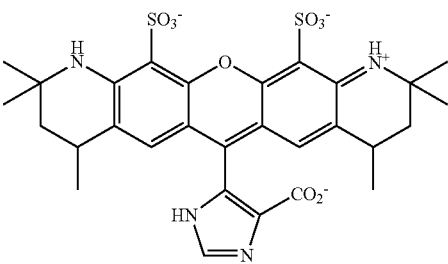 | 529/548 |
| 4 | 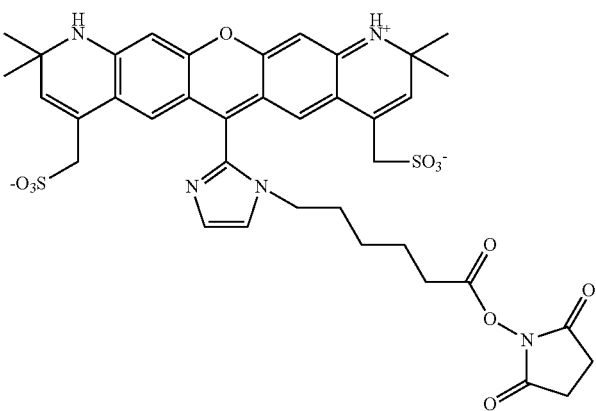 | 603/626 |
| 5 | 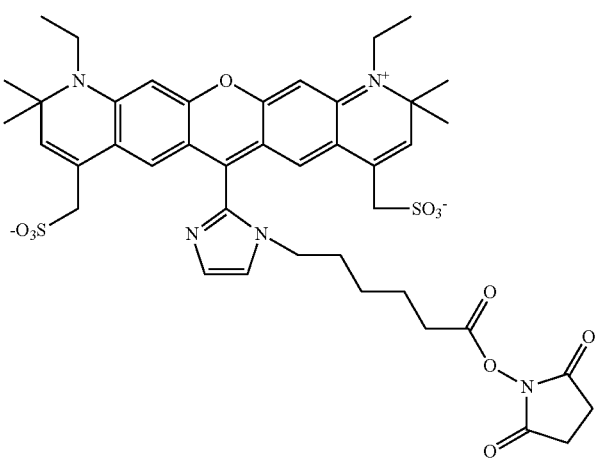 | 622/649 |

TABLE 2-continued
Exemplary compounds of the invention are shown. For simplicity, counter ions are not shown in some cases. Absorption/Emission spectra were measured in PBS unless otherwise indicated.
| Compound No. | Structure | Absorption/Emission Wavelengths (nm) |
|---|---|---|
| 6 | 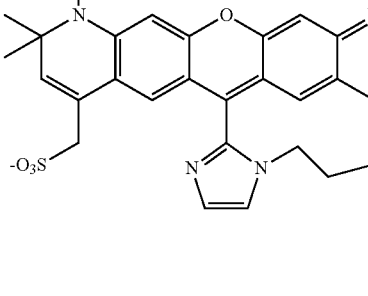 | 622/649 |
| 7 | 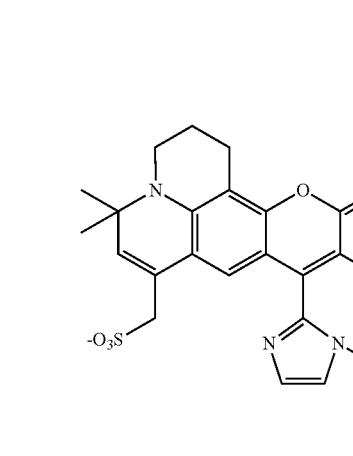 | 638/660 |
| 8 | 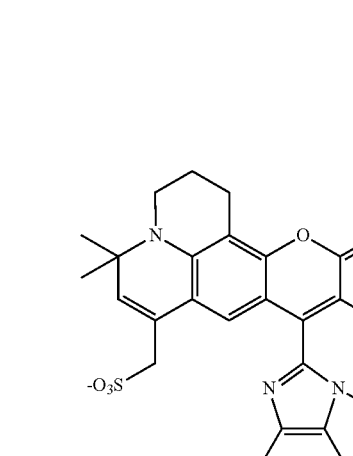 | |

TABLE 2-continued
Exemplary compounds of the invention are shown. For simplicity, counter ions are not shown in some cases. Absorption/Emission spectra were measured in PBS unless otherwise indicated.
| Compound No. | Structure | Absorption/Emission Wavelengths (nm) |
|---|---|---|
| 9 | 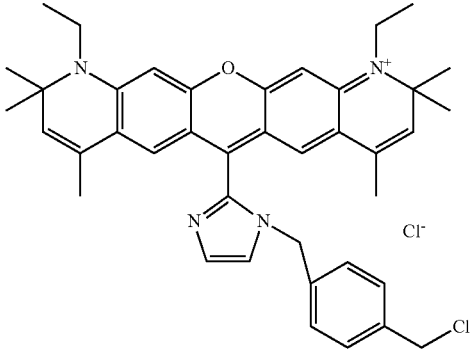 [SMILES: CCN1c2cc3c(cc2C(C)=CC1(C)C)C(c1nccn1Cc1ccc(CCl)cc1)=c1cc2c(cc1O3)=[N+](CC)C(C)(C)C=C2C ; [Cl-]] | 622/648 |
| 10 | 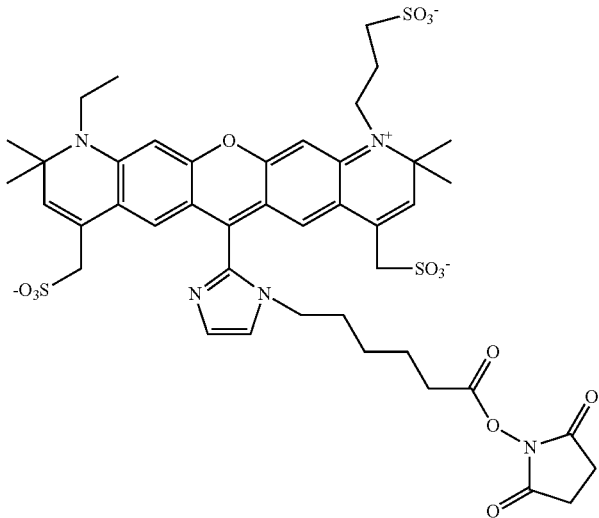 | 622/649 |
| 11 | 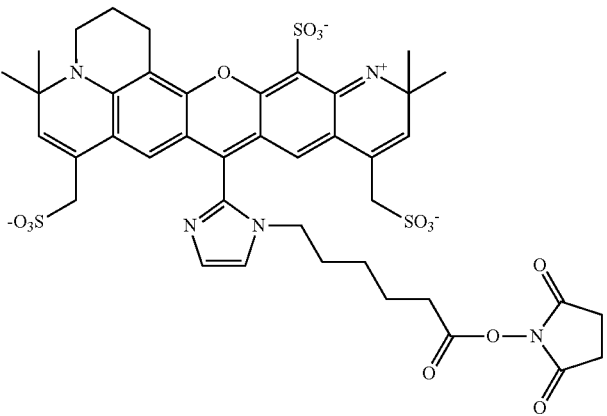 | |

TABLE 2-continued
Exemplary compounds of the invention are shown. For simplicity, counter ions are not shown in some cases. Absorption/Emission spectra were measured in PBS unless otherwise indicated.
| Compound No. | Structure | Absorption/Emission Wavelengths (nm) |
|---|---|---|
| 12 | 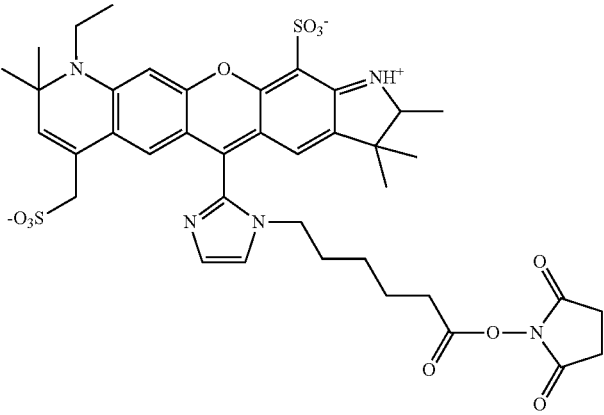 | |
| 13 | 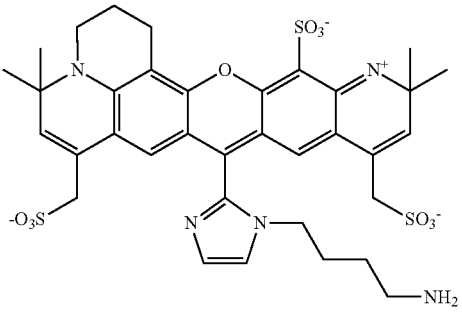 | |
| 14 | 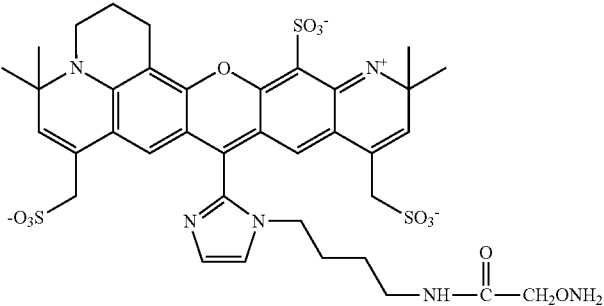 | |
| 15 | 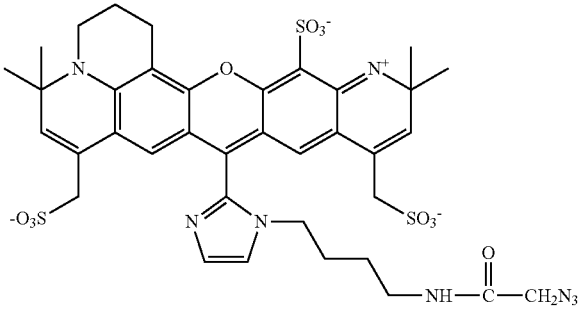 | |

TABLE 2-continued
Exemplary compounds of the invention are shown. For simplicity, counter ions are not shown in some cases. Absorption/Emission spectra were measured in PBS unless otherwise indicated.
| Compound No. | Structure | Absorption/Emission Wavelengths (nm) |
|---|---|---|
| 16 | 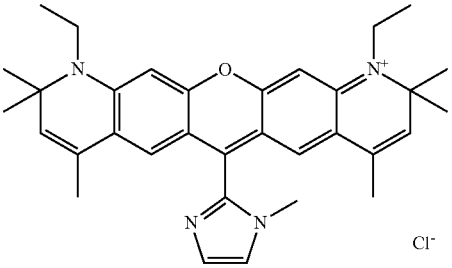 | 622/648 (in MeOH) |
| 17 | 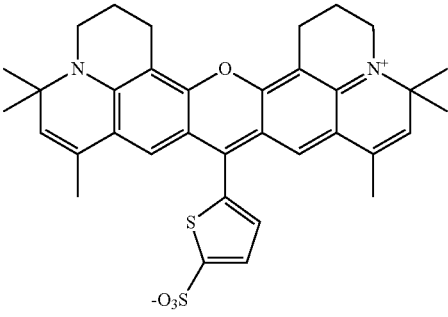 | |
| 18 | 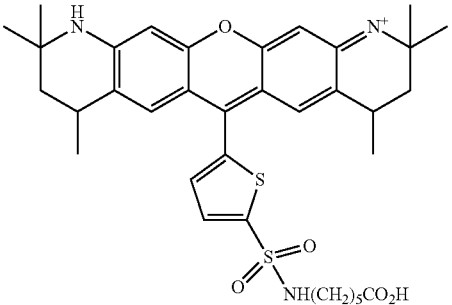 | |
| 19 | 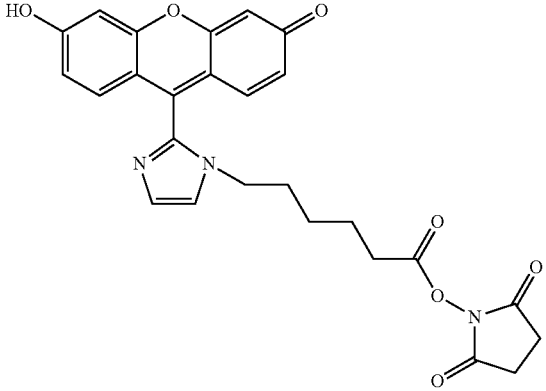 [SMILES: O=C(CCCCCn1ccnc1-c1c2ccc(=O)cc-2oc2cc(O)ccc12)ON1C(=O)CCC1=O] | |

TABLE 2-continued
Exemplary compounds of the invention are shown. For simplicity, counter ions are not shown in some cases. Absorption/Emission spectra were measured in PBS unless otherwise indicated.
| Compound No. | Structure | Absorption/Emission Wavelengths (nm) |
|---|---|---|
| 20 | 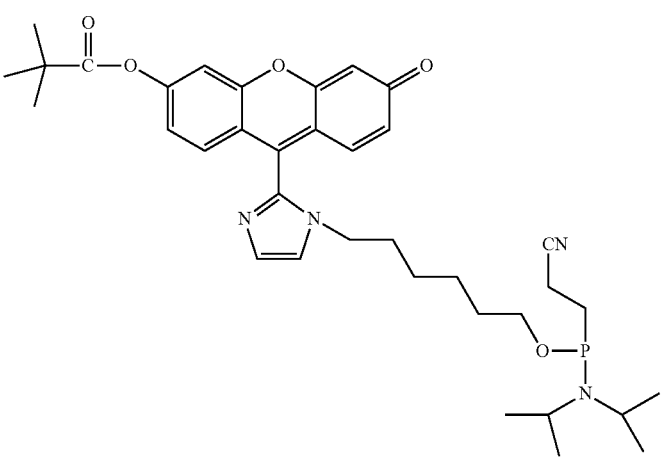 [SMILES: CC(C)N(C(C)C)P(CCC#N)OCCCCCCn1ccnc1-c1c2ccc(=O)cc-2oc2cc(OC(=O)C(C)(C)C)ccc12] | |
| 21 | 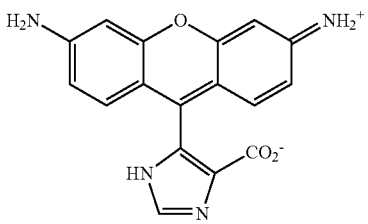 | 485/508 |
| 22 | 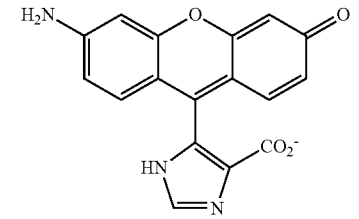 | |
| 23 | 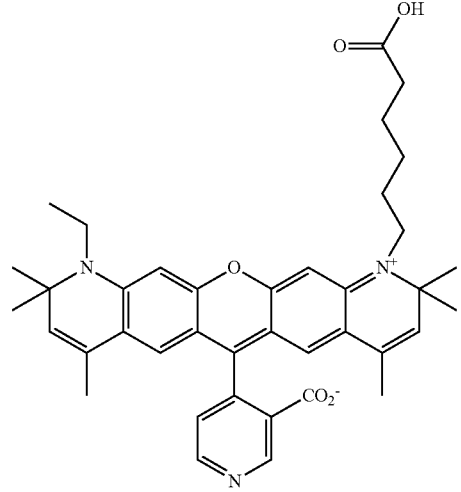 | 599/~620 |

TABLE 2-continued
Exemplary compounds of the invention are shown. For simplicity, counter ions are not shown in some cases. Absorption/Emission spectra were measured in PBS unless otherwise indicated.
| Compound No. | Structure | Absorption/Emission Wavelengths (nm) |
|---|---|---|
| 24 | 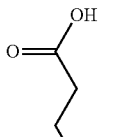 | |
| 25 | 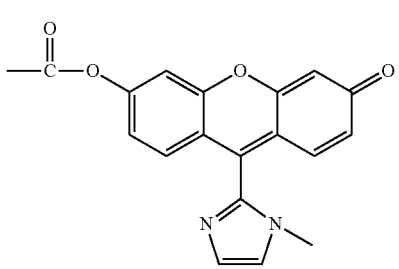<br>esterase substrate | |
| 26 | 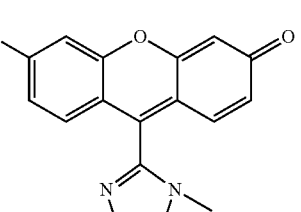<br>Caspase-3 substrate | |
| 27 | 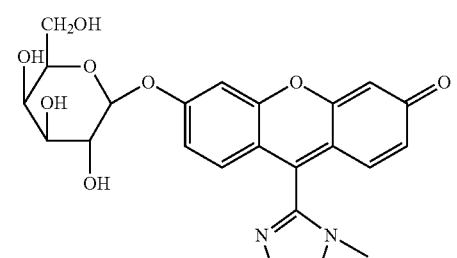<br>β-galactosidase substrate | |

TABLE 2-continued
Exemplary compounds of the invention are shown. For simplicity, counter ions are not shown in some cases. Absorption/Emission spectra were measured in PBS unless otherwise indicated.
| Compound No. | Structure | Absorption/Emission Wavelengths (nm) |
|---|---|---|
| 28 | 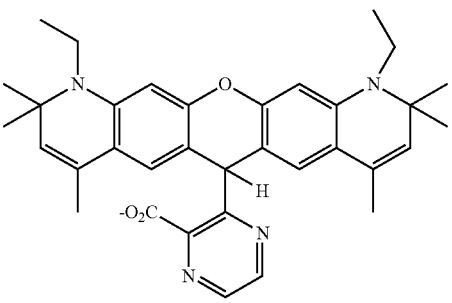<br>Peroxidase substrate | |
| 29 | 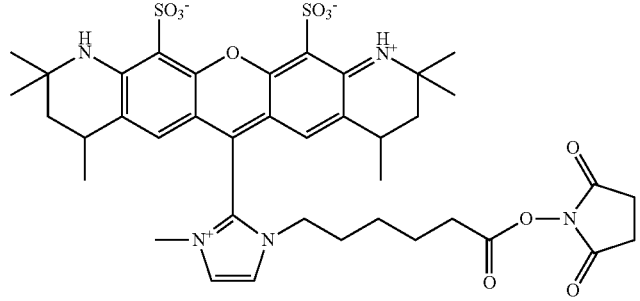 | 592/615 |
| 30 | 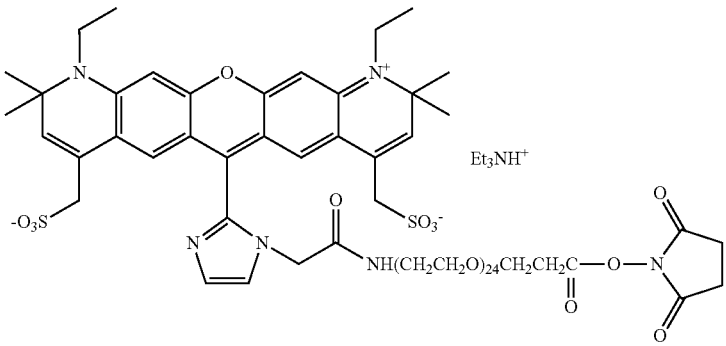 | 627/650 |
| 70 | 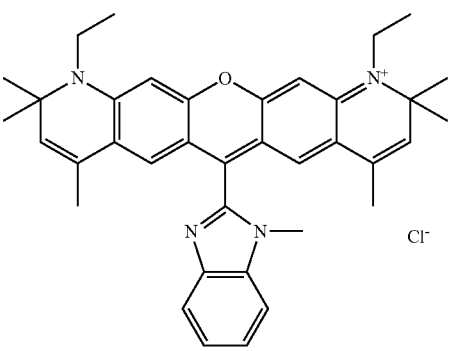 | 628/656 (in MeOH) |

TABLE 2-continued

Exemplary compounds of the invention are shown. For simplicity, counter ions are not shown in some cases. Absorption/Emission spectra were measured in PBS unless otherwise indicated.

| Compound No. | Structure | Absorption/Emission Wavelengths (nm) |
|---|---|---|
| 71 | 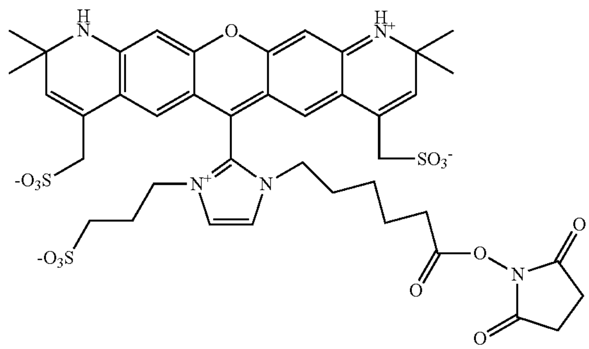 | 642/662 |
| 72 | 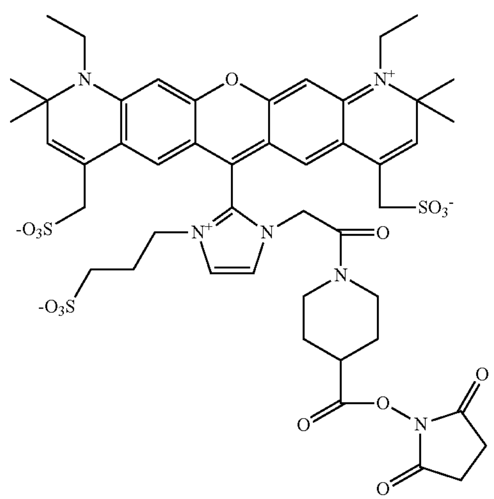 | 660/681 |
| 73 | 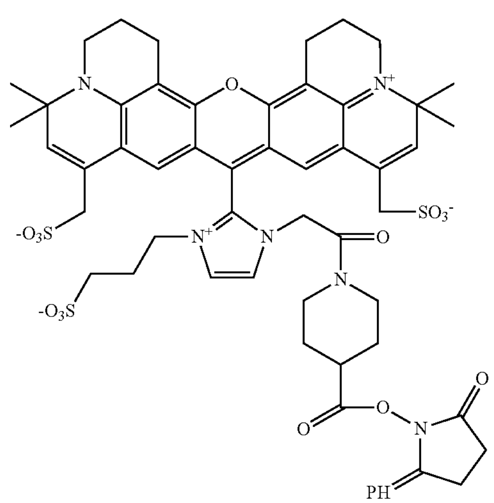 | 683/700 |

TABLE 2-continued

*Exemplary compounds of the invention are shown. For simplicity, counter ions are not shown in some cases. Absorption/Emission spectra were measured in PBS unless otherwise indicated.*

| Compound No. | Structure | Absorption/Emission Wavelengths (nm) |
|---|---|---|
| 74 | 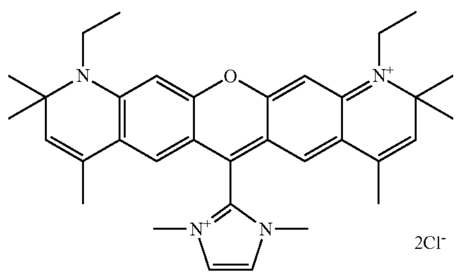 | 660/688 (in MeOH) |
| 75 | 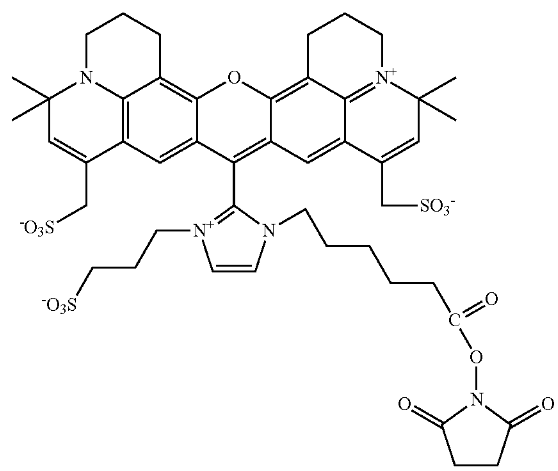 | 680/701 |
| 76 | 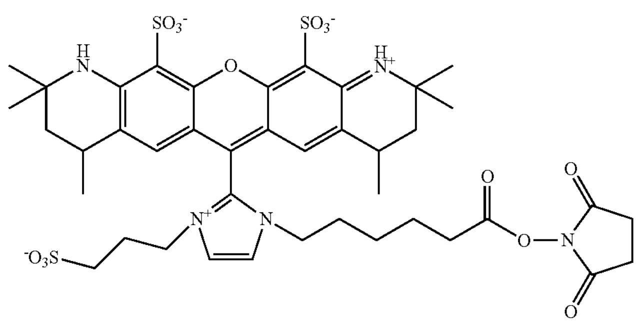 | 593/614 |
| 77 | 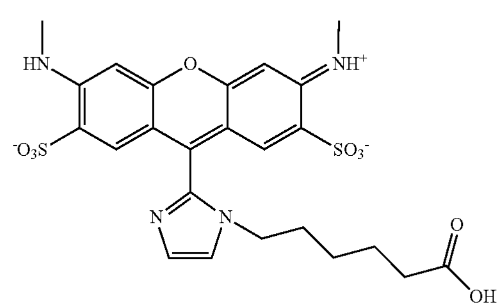 | 578/ |

TABLE 2-continued
Exemplary compounds of the invention are shown. For simplicity, counter ions are not shown in some cases. Absorption/Emission spectra were measured in PBS unless otherwise indicated.
| Compound No. | Structure | Absorption/Emission Wavelengths (nm) |
|---|---|---|
| 78 | 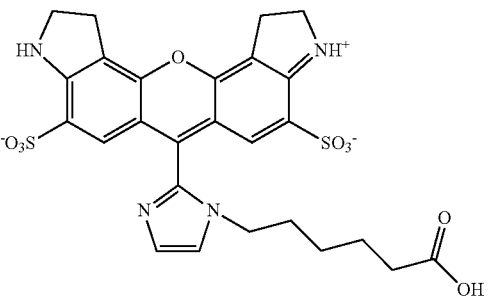 | |
| 79 | 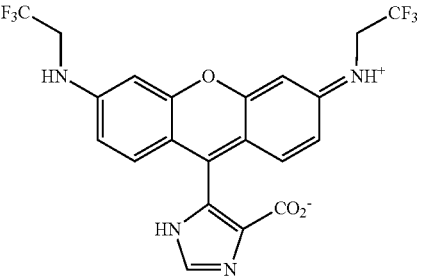 | |
| 80 | 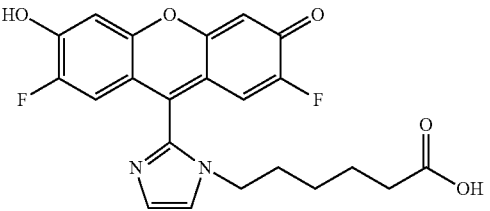 [SMILES: O=C(O)CCCCCn1ccnc1-c1c2cc(F)c(=O)cc-2oc2cc(O)c(F)cc12] | |
| 81 | 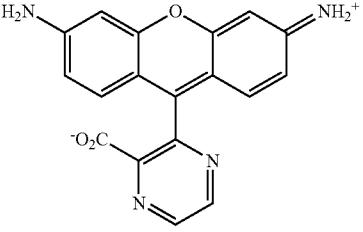 | |
| 82 | 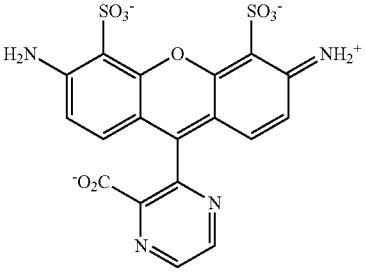 | |

TABLE 2-continued
Exemplary compounds of the invention are shown. For simplicity, counter ions are not shown in some cases. Absorption/Emission spectra were measured in PBS unless otherwise indicated.
| Compound No. | Structure | Absorption/Emission Wavelengths (nm) |
|---|---|---|
| 83 | 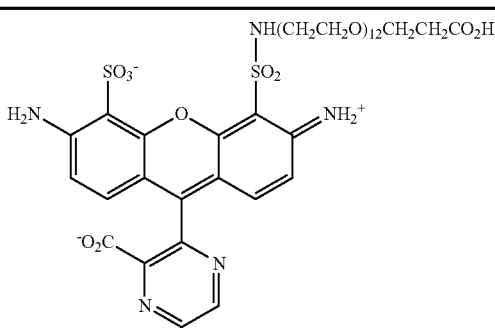 | |
| 84 | 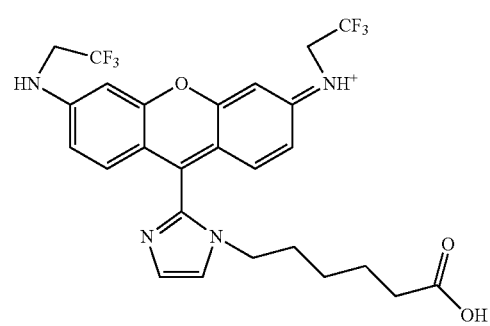 [SMILES: O=C(O)CCCCCn1ccnc1-c1c2cc/c(=[NH+]/CC(F)(F)F)cc-2oc2cc(NCC(F)(F)F)ccc12] | 533/550 |
| 85 | 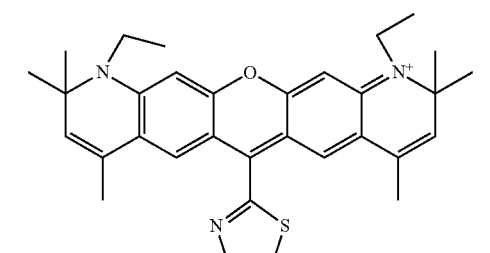 | 627/698 |
| 86 | 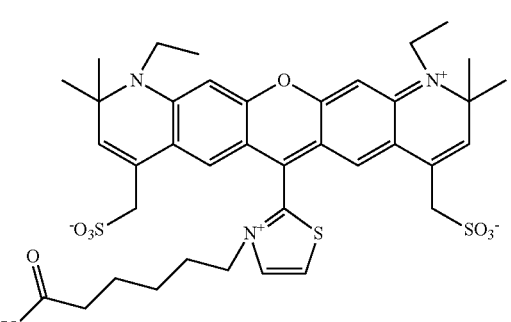 | |
| 87 | 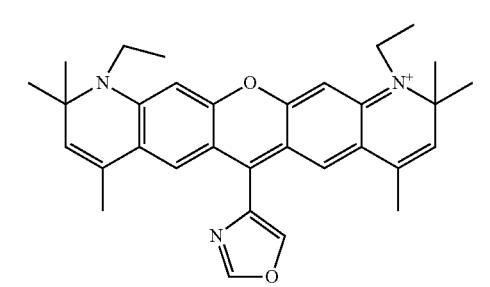 | 647/676 |

TABLE 2-continued

Exemplary compounds of the invention are shown. For simplicity, counter ions are not shown in some cases. Absorption/Emission spectra were measured in PBS unless otherwise indicated.

| Compound No. | Structure | Absorption/Emission Wavelengths (nm) |
|---|---|---|
| 88 | 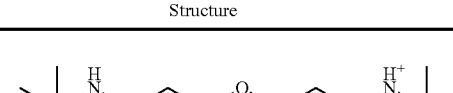 | 642/662 |

Synthesis of the Compounds of the Invention

In another aspect, the invention provides methods of synthesizing xanthene dyes of the invention substituted with heterocycle substituents.

Various preparations of xanthene dyes have been described. In general, the procedures involve high temperatures, such as well above 100° C., typically 130° C. and sometimes even above 200° C. Additionally, an acid is usually used either as a catalyst and/or a solvent. For xanthene dyes with rhodamine structures, one or two m-aminophenol precursor(s) are usually condensed with an arene-o-dicarboxylic anhydride to form the dye in refluxing n-propionic acid and using concentrated sulfuric acid or p-toluenesulfonic acid as a catalyst. Alternatively, a mixture of the m-aminophenol(s) and anhydride and zinc chloride is heated at 180° C. or above 200° C. to form the dye. For xanthene dyes with rosamine structures, one or two m-aminophenol precursor(s) and an arene-carboxaldehyde are usually condensed in sulfuric acid at 100-140° C. to form a dihydroxanthene dye intermediate, which is then oxidized to form the dye. For xanthene dyes with fluorescein structures, a resorcinol precursor is reacted with an arene-o-dicarboxylic anhydride in an acetic solvent such as methanesulfonic acid at 80-90° C. Typical procedures for preparing rhodamine dyes, rhodol dyes, rosamine dyes and fluorescein dyes are described in U.S. Pat. Nos. 5,750,409; 5,792,389; and 6,130,101. Xanthene dyes comprising a heteroaryl have been synthesized from a xanthene intermediate and a organometalic heteroaryl compound (Ahn, et al. J. Am. Chem. Soc. 129(5), 4510 (2007)). Procedures described in these prior art publications and in references cited therein may be used to prepare the compounds of the invention provided that sufficiently stable heteroaryl compounds are used. However, it may not always be possible to apply the known procedures due to incompatibility with the chemical properties of the heteroaryl compound, such as 5-membered heteroaryl compounds which may be labile or may comprise labile substituents.

Therefore, the present invention provides a process for preparing dyes of the invention which may allow the use of lower temperatures and smaller amounts of acid. In one aspect, the invention provides a method of preparing a fluorescent dye precursor comprising:

a) preparing a reaction mixture comprising an aminophenol or resorcinol precursor of formula:

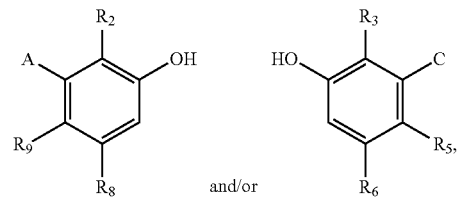

an aldehyde precursor of formula

or a diacetal derivative thereof, and an acid catalyst;

b) incubating said mixture between 0 and 100° C. for a time sufficient to result in a fluorescent dye precursor of the formula:

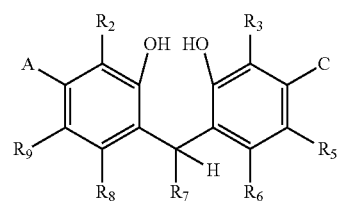

wherein A is $-OR_1$ or $-NR_1R_{1a}$;

C is $-OR_4$ or $-NR_4R_{4a}$;

$R_1$, $R_{1a}$, $R_4$, and $R_{4a}$ are each independently H or alkyl, unsubstituted or substituted with $-L-SO_3^-$, $-L-PO_3^{2-}$, a water-soluble polymer, or with $-L-R_x'$; or one or more pair of $R_1$ and $R_{1a}$ or $R_4$ and $R_{4a}$ together with the nitrogen to which they are attached form a saturated or unsaturated ring optionally substituted by any of $-L-SO_3^-$, $-L-PO_3^{2-}$ and $-L-R_x'$; or at least one of $R_1$, $R_{1a}$, $R_4$, or $R_{4a}$ is an enzyme substrate or a protecting group;

$R_2$, $R_3$, $R_5$, $R_6$, $R_8$, and $R_9$ are H or alkyl, unsubstituted or substituted with $-L-SO_3^-$, $-L-PO_3^{2-}$, a water-soluble polymer, or with $-L-R_x'$; or one or more pair of $R_1$ and $R_{1a}$ or $R_4$ and $R_{4a}$ together with the nitrogen to which they are attached form a saturated or unsaturated ring optionally substituted by any of -L-SO$_3^-$, -L-PO$_3^{2-}$ and -L-R$_x$';

$R_7$ is a 5-10 membered monocyclic or bicyclic heterocycle, unsubstituted or substituted with halogen, CO$_2^-$, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$';

R$_x$' is a protected R$_x$ moiety or a chemical precursor of a R$_x$ moiety;

L is a bond or (Q)$_n$;

each Q is independently NR$_d$, S(O)$_t$, O, C(=X), (C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two NR$_d$ are adjacent and no two O are adjacent;

n is 1-20; and each R$_d$ is H, substituted or unsubstituted alkyl.

In some embodiments, R$_7$ is

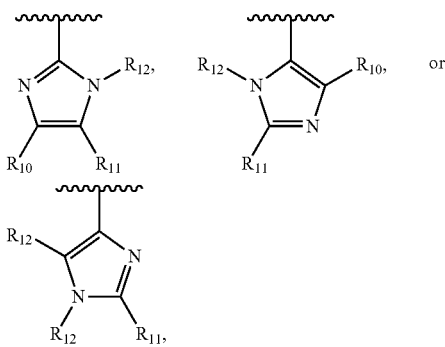

wherein R$_{10}$, R$_{11}$, and R$_{12}$ are each independently H, halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, or -L-R$_x$'.

The invention also provides a method of preparing a fluorescent dye comprising:

a) providing a fluorescent dye precursor of formula:

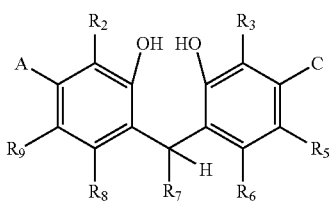

b) and incubating said precursor with an oxidizer for a time sufficient to result in the formation of a compound of formula:

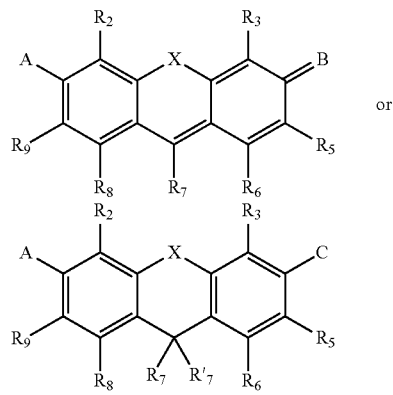

The oxidizer can be, for example, 2,3,5,6-tetrachloro-p-Benzoquinone (p-chloroanil) or 2,3-dichloro-5,6-dicyanobenzoquinone (DDQ). In the above processes, any of the starting materials for the synthesis may comprise a -L-R'$_x$, where L is as defined previously herein and R'$_x$ is a protected R$_x$ moiety or a chemical precursor of a R$_x$ moiety; such groups are chosen such as to be not reactive while the above reactions are taking place but can be readily converted to a reactive group by commonly used chemical transformation, such as hydrolysis, reduction, or activation, merely by way of example. For example, R'$_x$ may be an ester, such as a methyl or ethyl ester or t-butyl ester, or an aliphatic amine protected by a t-Boc or N-phthalimide group. These protecting groups are compatible with the synthesis methods described and can be readily converted to a reactive group R$_x$ in a subsequent step. In one embodiment, the heteroaryl R$_7$ comprises a -L-R'$_x$ group. In another embodiment, the R'$_x$ group is a carboxylic methyl or ethyl ester.

(1) Uses of the Subject Compounds.

The subject compounds find use in a variety of different applications. One application of interest is the use of the subject compounds comprising a reactive group as labeling agents which are capable of imparting a fluorescent property to a particular composition of matter. The compounds of the present invention comprising a reactive group R$_x$ can be used to react with any of a broad range of molecules, including but not limited to, biomolecules such as polypeptides, polypeptide-based toxins, amino acids, nucleotides, polynucleotides including DNA and RNA, lipids, and carbohydrates, or a combination thereof. Additionally, the compounds of the invention comprising a reactive group R$_x$ can be used to react with haptens, drugs, ion-complexing agents such as metal chelators, microparticles, synthetic or natural polymers, cells, viruses, other fluorescent molecules including the dye molecule according to the invention, or surfaces. The substrate molecules (i.e., the molecules to be covalently labeled) typically comprise one or more functional groups, which react with the reactive group of the subject compounds to form covalent or linkage. In one aspect, the reactive group of a compound of the invention is an activated ester (such as a succinimidyl ester, or SE), a maleimide, a hydrazide or an aminooxy group. Accordingly, in some aspects, functional group from a substrate molecule is an amine, a thiol, an aldehyde or ketone. The resulting fluorescently labeled substrate molecules may be referred to as conjugates or labeled substrate molecules. Any methods practiced in the art (e.g., Brinkley, Bioconjugate Chem. 3, 2(1992), incorporated herein by reference) for preparing fluorescent group-substrate conjugates are applicable for practicing the subject invention.

Conjugates of biomolecules and compounds of the invention usually have high fluorescence yield while typically retaining the critical parameters of unlabeled biomolecules, such as solubility, selective binding to a receptor or nucleic acid, activation or inhibition of a particular enzyme or the ability to incorporate into a biological membrane. Nevertheless, conjugates with the highest degree of labeling may still precipitate or bind nonspecifically. As necessary, a less-than-maximal degree of labeling may be acceptable in order to preserve function or binding specificity. Preparing the conjugates of the invention may involve experimentation to optimize properties. Following conjugation, unconjugated labeling reagent may be removed by techniques known in the art such as by gel filtration, dialysis, conjugate precipitation and resolubilization, HPLC or a combination of these techniques. The presence of free dye, particularly if it remains chemically reactive, may complicate subsequent experiments with the bioconjugate.

Compounds of the inventions can also be used to stain biological targets via physical interactions, such as hydrophobic interaction or electrostatic interaction or both, or via physical entrapment. In such cases, compounds of the invention are not required comprise a reactive group $R_x$.

Compounds of the invention comprising an enzyme substrate ($E_s$) moiety are useful for detecting enzyme activities. The enzyme detection may be in a cell-free system, such as cell lysates, or in live cells. Thus, enzyme substrates of the invention may be useful for detecting cellular activities associated with certain enzyme activities and useful for screening drug candidates that target certain enzymes. The substrates may also be useful for studying the cytotoxicity of agents, such as drugs or drug candidates.

Use of the Compounds for Labeling Nucleic Acids

In another embodiment, the subject compounds can be used to conjugate with a nucleoside, a nucleotide, or a polynucleotide, wherein any of such molecules may be natural or synthetic, modified or unmodified. The compound of the invention used for labeling may comprise a reactive group which is a phosphoramidite, an activated ester (such as a succinimidyl ester), an alkylating group or a reactive platinum complex. Such molecules may contain or are derivatized to contain one or more reaction partners for the reactive groups on the compounds of the invention. A reactive group of a compound of the invention may react with a suitable reaction partner on said molecule to form a covalent linkage. For example, a phosphoramidite group may react with a hydroxyl group to form a phosphate linkage after deprotection; a succinimidyl ester or the like may react with an amine group to form an amide linkage; and a reactive platinum complex may react with a guanosine base to form a platinum complex linkage. In one embodiment, a reactive compound of the invention comprising an activated ester is reacted with a nucleotide triphosphate comprising a base comprising an aminoalkynyl group, an aminoallyl group or an aminoalkyl group to form a fluorescently labeled nucleotide triphosphate. Such a labeled nucleotide triphosphate is often used to prepare a fluorescently labeled nucleic acid polymer via enzymatic incorporation.

In some embodiments, the fluorescent compound of the invention is reacted with a group or linker attached to the C-5 position of a uridine or cytidine residue. This position is not involved in Watson-Crick base-pairing and interferes little with hybridization to complementary sequences. An aminoalkynyl or aminoallyl linker may be introduced between a fluorescent moiety and the nucleotide in order to reduce fluorophore interaction with enzymes or target binding sites. In addition to this four-atom bridge, seven- to 10-atom spacers may be introduced that further separate the fluorophore from the base. The use of longer spacers may result in brighter conjugates and increased hapten accessibility for secondary detection reagents.

Alternatively, deoxycytidine triphosphates may be prepared which are modified at the N-4 position of cytosine using a 2-aminoethoxyethyl (OBEA) linker. Possible steric interference caused by the presence of the fluorescent fluorophore may be reduced by the use of additional spacers.

Fluorescently labeled DNA may be prepared from a fluorescently labeled nucleotide triphosphate by PCR reaction, terminal transferase-catalyzed addition or nick translation. Various polymerases may be used in such reactions. Such polymerases include Taq polymerase (useful e.g. in polymerase chain reaction (PCR) assays), DNA polymerase I (useful e.g. in nick-translation and primer-extension assays), Klenow polymerase (useful e.g. in random-primer labeling), Terminal deoxynucleotidyl transferase (TdT) (useful e.g. for 3'-end labeling), Reverse transcriptase (e.g. for synthesizing DNA from RNA templates) or other polymerases such as SP6 RNA polymerase, T3 RNA polymerase and T7 RNA polymerase for in vitro transcription.

Alternatively, a fluorescently labeled nucleic acid polymer may be prepared by first enzymatically incorporating an amine-labeled nucleotide into a nucleic acid polymer to result in an amine-labeled nucleic acid polymer, followed by the labeling of said amine-labeled polymer with a compound of the invention. More information on the preparation and use of fluorescently labeled nucleotide triphosphates can be found in U.S. Pat. Nos. 4,711,955 and 5,047,519. Still alternatively, a nucleic acid polymer, such as a DNA, may be directly labeled with a compound of the invention comprising a reactive platinum complex as the reactive group, wherein the platinum complex form a coordinative bond with a nitrogen atom of a guanosine base such as described in U.S. Pat. No. 5,714,327.

Use of the Compounds for Labeling Aminoacids and Polypeptides

In another embodiment, the subject compounds can be used to conjugate with an aminoacid, aminoacid analog or a polypeptide. Labeled aminoacids, aminoacid analogs and polypeptides may be labeled by reacting the compounds of the invention with aminoacids, aminoacid analogs and polypeptides comprising reaction partners for the reactive groups on said compounds. Such reaction partners may be natural or unnatural groups present in said polypeptides. By way of example, reaction partners may be the natural residues such as amino groups, which are part of natural lysine residues, or thiol groups, which are part of natural cysteine groups.

Figure 2:
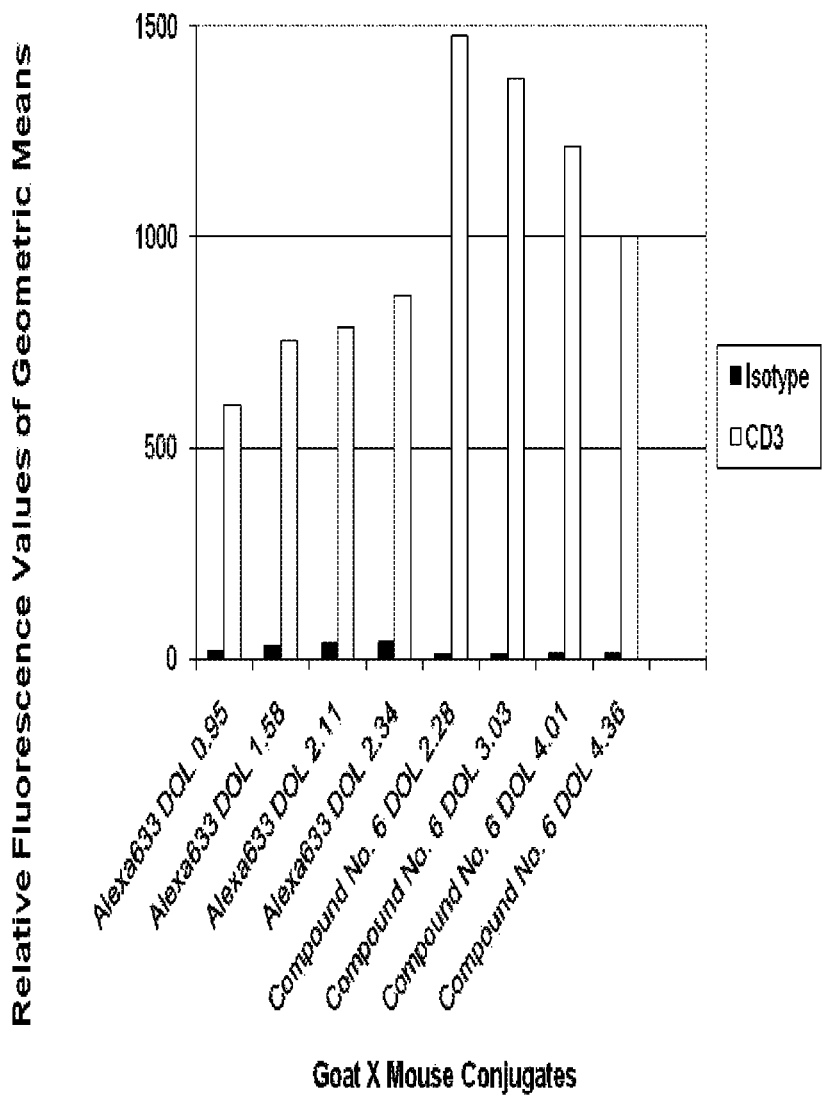
FIG. 2 shows the relative fluorescence levels of Jurkat cells stained first with mouse anti-human CD3 antibody and then with goat anti-mouse IgG labeled with either Compound No. 6 or Alexa Fluor 633 at an indicated DOL.
Figure 3:
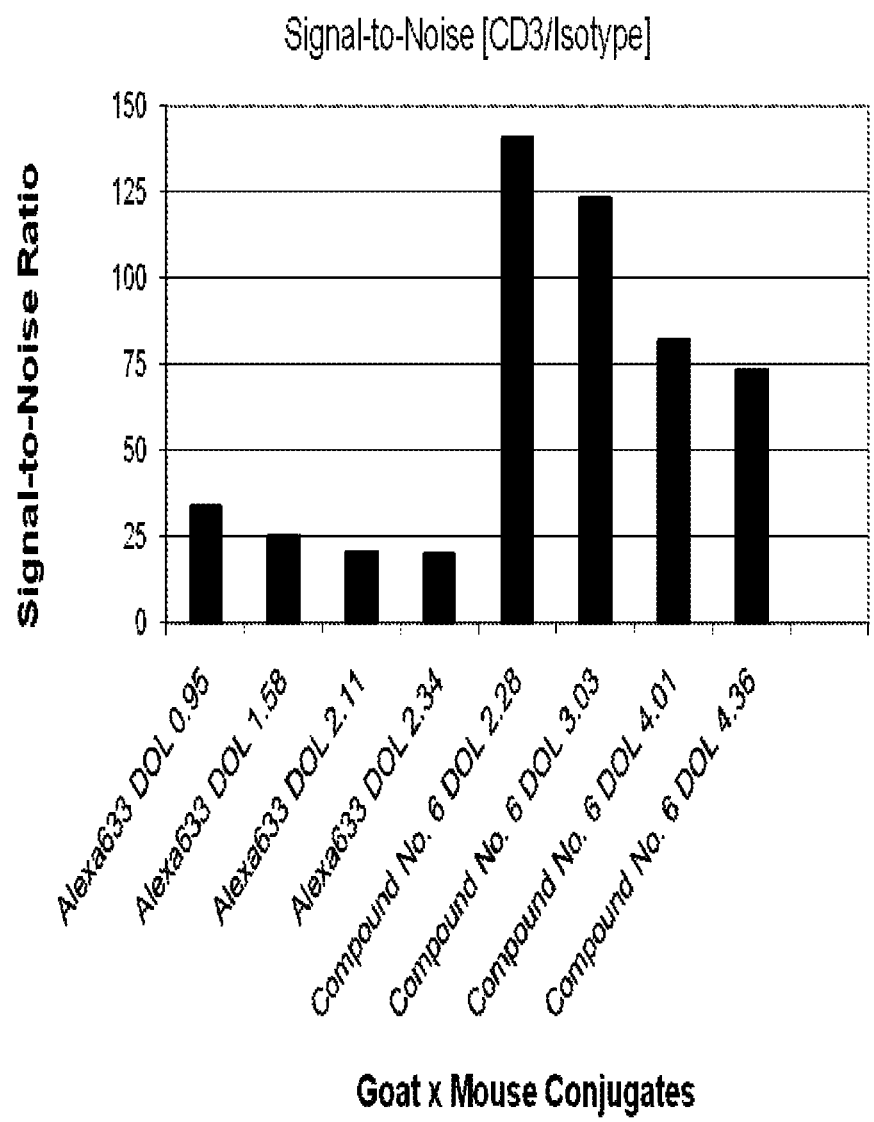
FIG. 3 is a plot of the signal-to-noise ratio (S/N) for the staining results in FIG. 2.
Figure 4:
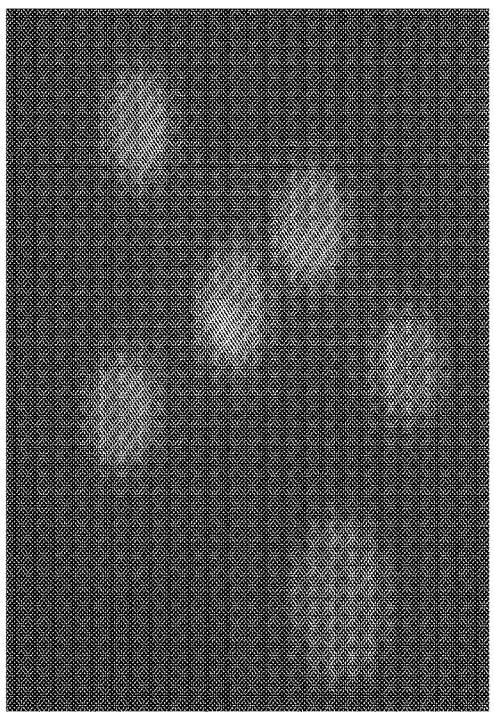
FIG. 4 shows microscopic images of Jurkat cells fixed and stained with intracellular mouse anti-human CD3 primary antibody followed by goat-anti-mouse conjugated to AlexaFluor633 or compound No. 6.
Figure 4:
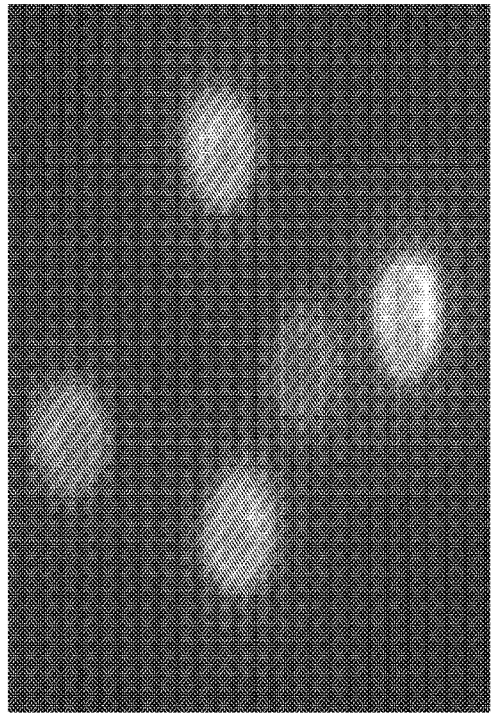
Figure 5:
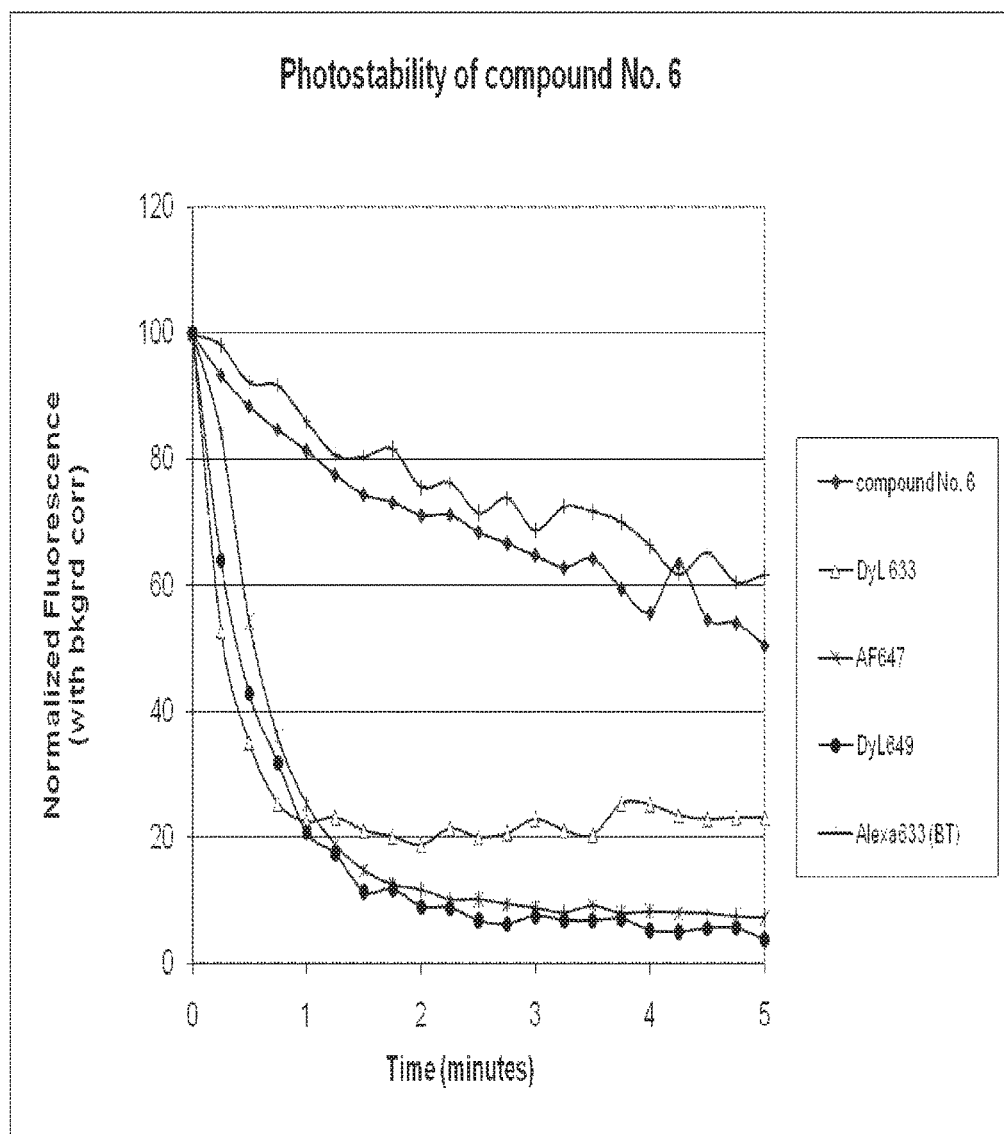
FIG. 5 shows a comparison of the photostability of compound No. 6 and several commercial dyes of similar wavelengths.
Figure 6:
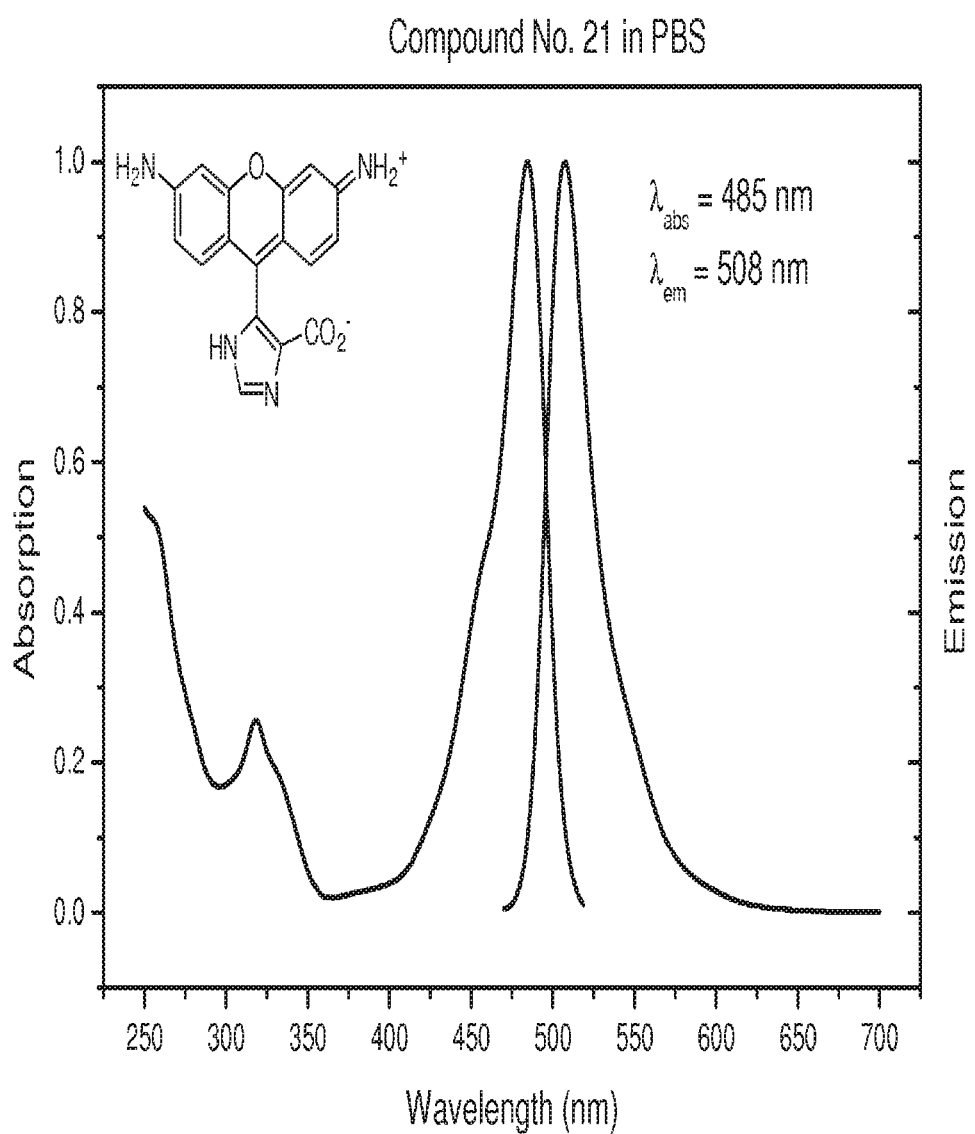
FIG. 6 is a graphical representation showing the absorption and emission spectra of compound No. 21 in PBS.
Figure 7:
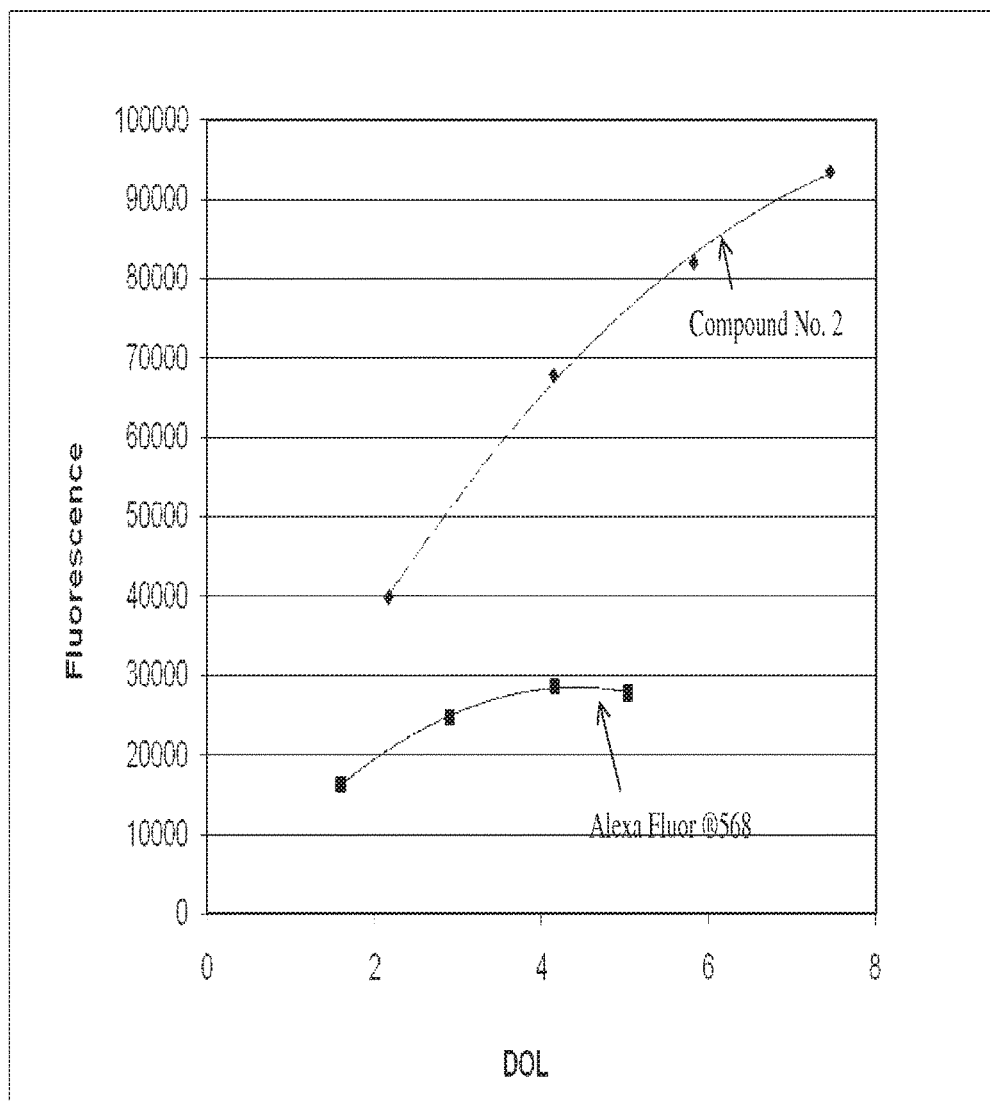
FIG. 7 is a plot of total fluorescence vs. degree of labeling (DOL) for goat anti-mouse IgG conjugates of Compound No. 2 and Alexa Fluor® 568.
Figure 8:
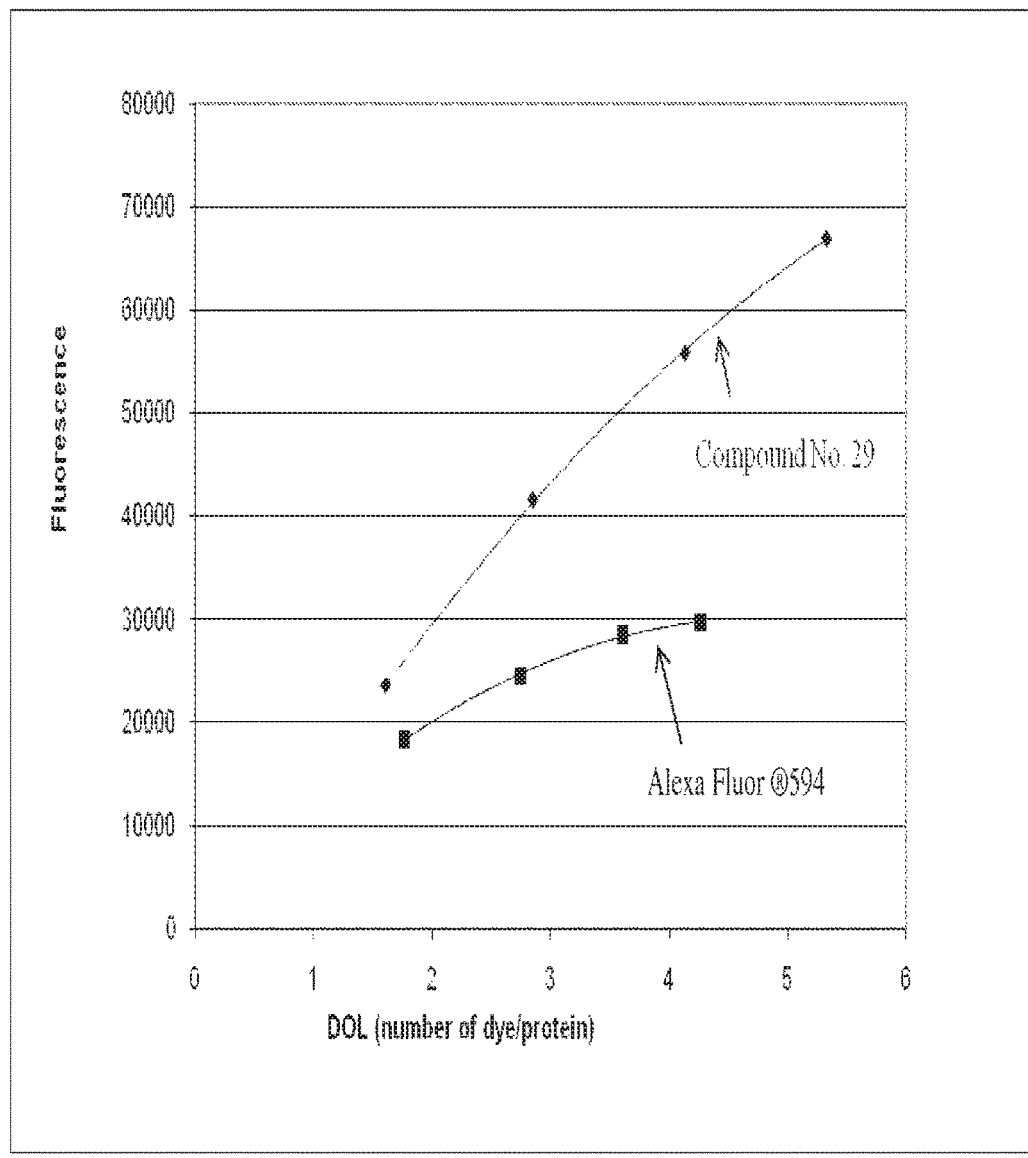
FIG. 8 is a plot of total fluorescence vs. degree of labeling (DOL) for goat anti-mouse IgG conjugates of Compound No. 29 and Alexa Fluor® 594.
Figure 9:
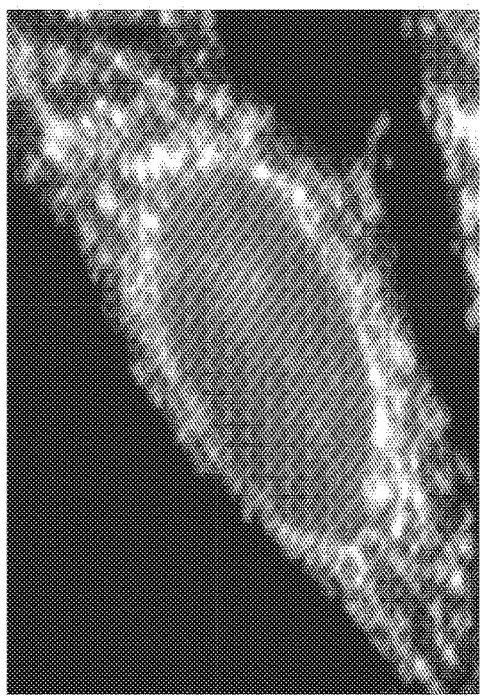
FIG. 9 shows mitochondrial staining of compound Nos. 16 and 74, respectively, in HeLa cells.
Figure 9:
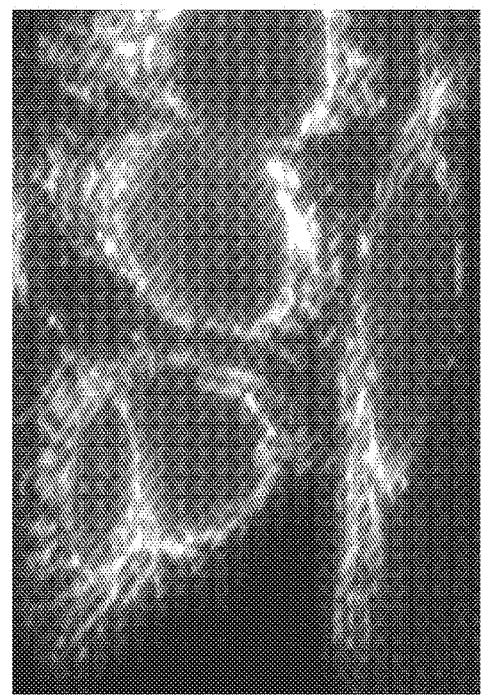

In order to achieve the maximal fluorescence possible, a protein may be labeled with as many molecules of the same fluorescent group as possible, to the degree that the biological activity of the protein is minimally affected by the labeling. In other cases it may be desirable to avoid fluorescence quenching resulting from multiple fluorescent group molecules on the protein interacting with each other. Dye-dye interactions may be physical, such as dye aggregation, or may be a spectral, such as FRET-based energy transfer, or a combination of both. Either type of interaction may lead to fluorescence quenching, which can be characterized by a slow rise of the total fluorescence of the labeled protein as the degree of labeling increases. Another factor affecting the fluorescence brightness of a protein conjugate is the intrinsic fluorescence or quantum yield of the single dye. A dye of poor fluorescence quantum yield will likely result in a weakly fluorescent protein conjugate, even if the dye has a relatively low tendency to aggregate on protein. Finally, when the fluorescently labeled protein is applied to biological detections, the sensitivity of the detection also depends on the optical compatibility of the dye with a given instruments. For fluorescent dyes with absorption wavelength in the 600-650 nm range, the 633 nm HeNe red laser is typically used as the excitation source. For example, this laser is widely equipped in fluorescence microscopes and flow cytometers. Ideally, dyes designed for this laser should have their absorption maxima wavelength as close to the 633 nm laser line as possible for optimal excitation. FIG. 1 shows compound No. 6, which has an absorption peak at about 633 nm, making the dye ideal for the 633 nm laser. Traditionally, cyanine-based dyes such as Cy5, Alexa Fluor 647 and more recently DyLight 647, are used for the 633 nm laser. However, all of these cyanine dyes have an absorption wavelength closer to 650 nm, which is well off the laser emission line. More recently, Alexa Fluor 633 dye and DyLight 633 dye have been developed as dyes specifically designed for the HeNe laser. However, these dyes either have serious dye aggregation problem on protein or poor fluorescence quantum yield, making them less widely used in applications. FIG. 2 compares secondary antibody conjugates prepared from compound No. 6 of the invention (Table 2) and Alexa Fluor 633 in fluorescence immunostaining by flow cytometry using 633 nm laser excitation. Compound No. 6 is significantly brighter than Alexa Fluor 633 at several different degrees of labeling. Also significantly, the signal-to-noise ratio using the compound No. 6-labeled antibody is much higher than that using the Alexa Fluor-labeled antibody (FIG. 3). The superior brightness of antibody labeled with compound No. 6 over that labeled with Alexa Fluor 633 is also confirmed by microscopy study of cells staining (FIG. 4). FIG. 5 compares the photostability of compound No. 6, Alexa Fluor 633 and DyLight 633. Both compound No. 6 and Alexa Fluor 633, which is a very photostable dye, are significantly more photostable than DyLight 633, and compound No. 6 has approximately similar stability to that of Alexa Fluor 633.

Use of the Compounds for Staining Mitochondria and Other Cellular Compartments

Certain compounds of the invention can also stain cellular targets via non-covalent labeling, such as via hydrophobic interaction with cell membranes. Compounds of the invention that are capable of acting as cell membrane stains, particularly mitochondrial membrane stains, generally have an overall positive charge. In general, this positive charge is the delocalized positive charge inherent to the xanthene ring. This means compounds of the invention suitable for staining mitochondrial membranes generally have a formula of formula 1a wherein substituents $R_1$, $R_{1a}$, $R_2$, $R_3$, $R_4$, $R_{4a}$, $R_5$, $R_6$, $R_7$, $R_8$ and $R_9$ are as described and neutral (not charged), such that the only positive charge is from the delocalized positive charge on the xanthene ring. Examples of such dyes include, but are not limited to, compounds No. 9, 16 and 74 of Table 2. Compound No. 9 also possesses a chloromethyl reactive group, which can crosslink the dye to mitochondrial membrane proteins having a thiol group (i.e., cysteine residue). Mitochondrial dyes having a thiol-reactive group can make the dyes fixable following staining as described in U.S. Pat. No. 6,291,203.

Figure 10:
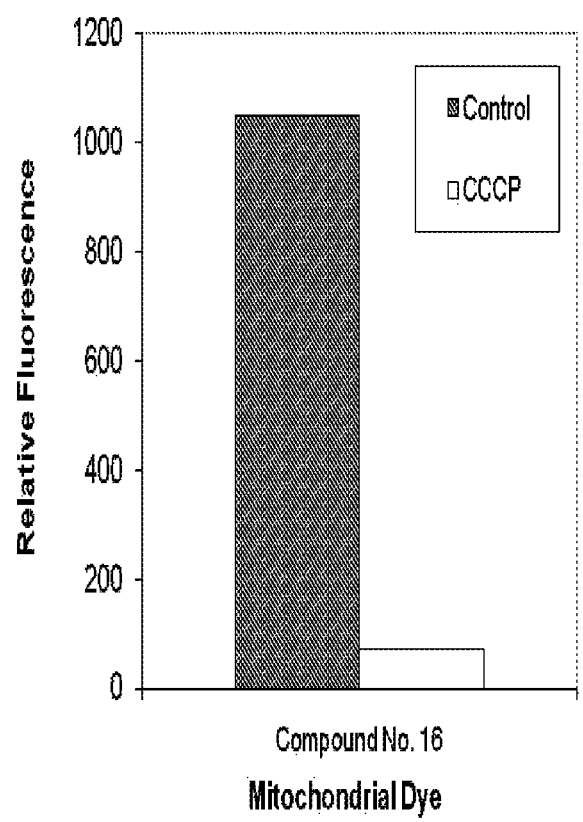
FIG. 10 is a histogram showing the relative mitochondrial staining intensities of compound No. 16 in HeLa cells before and after applying carbonyl cyanide m-chlorophenyl hydrazone (CCCP), a mitochondrial membrane potential decoupler agent.
Figure 11:
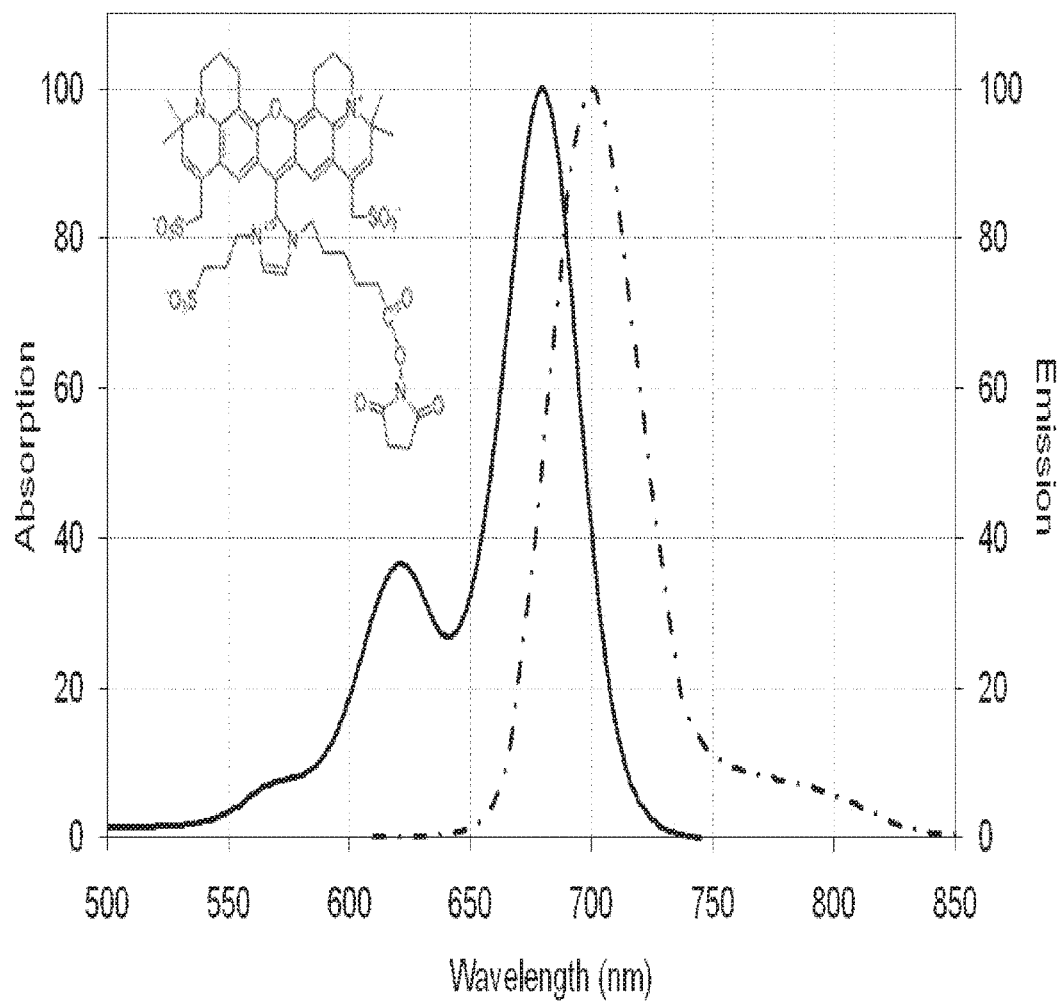
FIG. 11 is a graphical representation of the absorption and emission spectra of compound No. 75 conjugated to goat anti-mouse IgG in PBS. Also shown is the structure of Compound No. 75.

In general, mitochondrial dyes of the invention are not required to have a reactive group. Such mitochondrial dyes include, for example, compound No. 16, which does not have a reactive group. Such mitochondrial dyes lacking a reactive group, though non-fixable, may associate with mitochondria in a membrane-potential-dependent manner, thus reflecting the health of the mitochondria or cells. (See FIG. 10). For example, cells undergoing apoptosis lose their mitochondrial membrane potential. Thus, compound No. 16 is useful to distinguish apoptotic cells from normal healthy cell by virtue of their mitochondrial fluorescence intensity.

Compounds of the invention can also be used to stain aqueous cellular compartments via physical trapping or confinement by the cellular membranes. Suitable dyes for this application generally have at least two negative charges, making the dyes highly polar and water-soluble. This type of fluorescent dyes is typically referred to as fluorescent polar tracers for tracing the morphology of cells, such as neurons, or for tracing cell lineage as cells divide and differentiate. Because this type of dyes are generally small in size, highly water soluble and nontoxic, they can rapidly diffuse into the entire cell cytoplasm, making it possible for one to visualize the morphology of one single cell or a few selected cells in a complex environment, such as in a tissue. For example, fluorescent polar tracers enable one to visualize the fine structures of dendrites and axon of a neuron and its interaction with another neighboring neuron in a cell culture or tissue. A polar tracer is usually introduced into cells via microinjection or other suitable techniques. One of the early generation of fluorescent polar tracers is Lucifer Yellow (Stewart, W W, Nature 292, 17(1981)). More recently, Alexa Fluor 488 hydrazide (available from Invitrogen Co., cat #10436) and CF647 hydrazide (available from Biotium, Inc. cat #92136). Preferably, fluorescent polar tracer also comprise at least one reactive group that can crosslink the dye to intracellular proteins during formaldehyde or glutaldehyde fixation, when necessary. Preferred reactive group are selected from hydrazide, an aliphatic amine and aminooxy groups. Thus, compounds of the invention suitable as polar tracers generally have the formula of formula 1a, wherein at least any one of, or any combination of $R_1$, $R_{1a}$, $R_2$, $R_3$, $R_4$, $R_{4a}$, $R_5$, $R_6$, $R_7$, $R_8$ and $R_9$ comprise two negative charges. Preferably, the negative charges are sulfonates ($-SO_3^-$). More preferably, at least one of $R_1$, $R_{1a}$, $R_2$, $R_3$, $R_4$, $R_{4a}$, $R_5$, $R_6$, $R_7$, $R_8$ and $R_9$ also comprises a hydrazide, an aliphatic amine or an aminooxy group.

(2) Uses of Covalently Labeled Biomolecules of the Invention

The subject compounds provide an effective tool for covalently labeling biomolecules for a wide variety of applications. Labeling allows one to discern interactions involving biomolecules such as proteins, glycoproteins, nucleic acids, and lipids, as well as inorganic chemicals, or any combinations thereof. The interactions may be between nucleic acid molecules, between nucleic acid and protein, and between protein and small molecules. The interactions may be discerned in a cell-free biological system, in a cellular system (including intracellular and extracellular systems), or in vivo. Delineating the various interactions is often a significant step in scientific research and development, drug design, screening and optimization, phylogenetic classification, genotyping individuals, parental and forensic identification, environmental studies, diagnosis, prognosis, and/or treatment of disease conditions.

Biomolecules labeled according to the methods of the invention may be used as binding agents to detect their binding partners, the targets of their biological interaction, as described above. For example, a protein can be labeled with the label of the invention and used to bind to a cell surface receptor. In some embodiments of the invention, a binding agent is labeled with a xanthene dye of the invention having at least one reactive group under conditions effective to crosslink the dye and the binding agent. A binding agent so labeled is contacted with its binding partner, and the fluorescent label is detected.

General Applications

Labeled molecules of the invention may be used as part of FRET pairs in a variety of biological assays and methods, whether as donor or acceptor molecules. A person skilled in the art will know to select a suitable FRET partner based on the specific application. Such applications include, but are not limited to, assays involving molecular beacons, FRET protease assays, flow cytometry, nucleic acid hybridization and any other applications where the relative spatial localization of two or more moieties must be probed. FRET is generally useful on scales of 10 to 100 Å. In one embodiment, both the donor and the acceptor of a FRET pair are labeled molecules of the invention. In another embodiment, one member of a FRET pair is a labeled oligonucleotide of the invention which is capable of annealing to a complementary oligonucleotide labeled with a second member of the FRET pair, such that annealing leads to an increase in the efficiency of energy transfer. In this example, the second member of the FRET pair may be a fluorophore of the invention or may be a different fluorophore.

In some applications, it is desirable to quench the labeled molecules of the invention. A variety of quenchers known in the art may be used. Non-limiting examples include Black Hole Quencher™ moieties, DABCYL, Reactive Red 4 (Cibacron Brilliant Red 3B-A), Malachite Green, 4-Dimethylaminophenylazophenyl-4'-isothiocyanate (DABITC), and 4,4'-Diisothiocyanaitodihydro-stilbene-2,2'-disulfonic acid. By way of example, a molecular beacon may be labeled with a compound of the invention as well as with a suitable quencher. In the closed conformation of the beacon, the fluorophore is quenched. When the beacon opens as a result of a recognition or binding event, the fluorescence of the fluorophore increases significantly.

In still another embodiment, the invention provides an energy transfer fluorescent group comprising a first donor fluorescent group and second acceptor fluorescent group wherein: the donor fluorescent group and acceptor fluorescent group are covalently linked to form a FRET pair; at least one of the donor fluorescent group and acceptor fluorescent group is a fluorescent group of the invention; and the energy transfer fluorescent group optionally comprises a reactive group. Methods for preparing energy transfer fluorescent groups and uses thereof have been previously described. See U.S. Pat. No. 6,479,303 and WO 00/13026.

In one embodiment, a fluorescent group of the invention is used to label a fluorescent protein to form a so-called tandem dye, wherein the fluorescent group of the invention and the fluorophore of the fluorescent protein form an energy transfer pair (i.e., FRET pair). In such a FRET pair, the fluorescent group of the invention is either the donor fluorescent group or the acceptor fluorescent group and, likewise, the fluorophore of the protein is either the acceptor fluorescent group or the donor fluorescent group, such that the FRET pair can be excited at or near the absorption maxima of the donor fluorescent group and the fluorescence collected at the emission maxima of the acceptor fluorescent group, resulting in a large Stokes shift. Suitable fluorescent proteins for preparing tandem dyes include, but are not limited to, various phycobiliproteins such as Allophycocyanin B, Allophycocyanin (APC), C-Phycocyanin, R-Phycocyanin, Phycoerythrocyanin, C-Phycoerythrin, b-Phycoerythrin, B-Phycoerythrin, R-Phycoerythrin (R-PE), and the likes. Phycobiliproteins are proteins comprising bilin as prosthetic groups, which are also the fluorophores of the proteins. Preferably, the phycobiliproteins are R-PE or APC. To achieve suitable FRET efficiency, one may choose a fluorescent group of proper wavelengths so that the emission of the donor fluorescent group and the absorption of the acceptor fluorescent group have sufficient spectral overlap. Detailed methods for fluorescent group selection and for preparing tandem dyes are disclosed in U.S. Pat. Nos. 4,520,110 and 5,714,386. Because of their large Stokes shift, tandem dyes of the invention may be useful for multi-color detections where only a limited number of excitation light sources may be available. In particular, tandem dyes of the invention may be useful for fluorescence-activated cell sorting (FACS) or flow cytometry studies. Commercial flow cytometers are typically equipped with 1 to 3 excitation light sources, more commonly 1 to 2 excitation light sources. For example, some of the commercial flow cytometers are equipped with a 488 nm argon laser and a 633 nm He—Ne laser or a 635 nm red diode laser, and a significant number of flow cytometers have only the 488 nm argon laser. Thus, in order to detect multiple targets, each target may be stained with a different fluorescent group having a different emission and the different fluorescent groups all need to be efficiently excited by a common excitation source. Tandem dyes of the invention can fill this need as different tandem dyes having the same excitation maxima but different emission maxima can be readily prepared. For example, R-PE may be labeled with compound No. 6 of Table 2 to result in a tandem dye where the tandem dye is excitable at 488 nm with emission at about 645 nm.

In one embodiment, a compound of the invention is applied to a biological sample comprising a plurality of polypeptides and optionally other biological molecules under a condition facilitating the covalent labeling of said polypeptides. In some embodiments, the reactive group of the compound is an activated ester, a maleimide, an iodoacetamide, a bromoacetamide, a hydrazide, an amine or an aminooxy group. The biological sample may be a cell lysate or a tissue lysate. The resulting labeled polypeptides or cellular components may be analyzed and/or purified by any of a variety of known tools or techniques, including, but not limited to, protein microarrays, chromatography and gel electrophoresis.

The present invention also provides kits comprising compounds of the invention and/or fluorescent group-substrate conjugates of the invention for various assays as selectively described above. A kit of the invention may comprise one or more compounds of the invention and instructions instructing the use of said compound. For example, a kit may comprise one or more compounds of the invention for labeling a substrate, one or more buffers for the labeling reaction and product purification, a chromatography column for purifying the resulting fluorescent group-substrate conjugate, a protocol for carrying out the procedure, optionally any additional reagents and optionally any reference standard. In another embodiment, a kit comprises one or more fluorescent group-substrate conjugates of the invention, one or more buffers, a protocol for the use of said conjugate(s), optionally any other reagents for an assay, and optionally any calibration standard(s). The kit may further contain other materials or devices of use in purifying the conjugation products.

The signals produced by the fluorescent groups of the invention may be detected in a variety of ways. Generally, a change of signal intensity can be detected by any methods known in the art and is generally dependent on the choice of fluorescent group used. It can be performed with the aid of an optical system. Such system typically comprises at least two elements, namely an excitation source and a photon detector. Numerous examples of these elements are available in the art. An exemplary excitation source is a laser, such as a polarized laser. The choice of laser light will depend on the fluorescent group attached to the probe. For most of the fluorescent groups, the required excitation light is within the range of about 300 nm to about 1200 nm, or more commonly from about 350 nm to about 900 nm. Alternatively, compounds of the invention may be excited using an excitation wavelength of about 300 to about 350 nm, 350 to 400 nm, 400 to 450 nm, 450 to 500 nm, 500 to 550 nm, 550 to 600 nm, 600 to 650 nm, 650 to 700 nm, 750 nm to 800 nm, or from 800 nm to 850 nm, merely by way of example. Those skilled in the art can readily ascertain the appropriate excitation wavelength to excite a given fluorophore by routine experimentation (see e.g., The Handbook—'A Guide to Fluorescent Probes and Labeling Technologies, Tenth Edition' (2005) (available from Invitrogen, Inc./Molecular Probes) previously incorporated herein by reference). Where desired, one can employ other optical systems. These optical systems may comprise elements such as optical reader, high-efficiency photon detection system, photo multiplier tube, gate sensitive FET's, nano-tube FET's, photodiode (e.g. avalanche photo diodes (APD)), camera, charge couple device (CCD), electron-multiplying charge-coupled device (EMCCD), intensified charge coupled device (ICCD), and confocal microscope. These optical systems may also comprise optical transmission elements such as optic fibers, optical switches, mirrors, lenses (including microlens and nanolens), collimators. Other examples include optical attenuators, polarization filters (e.g., dichroic filter), wavelength filters (low-pass, band-pass, or high-pass), wave-plates, and delay lines. In some embodiments, the optical transmission element can be planar waveguides in optical communication with the arrayed optical confinements. See, e.g., U.S. Pat. Nos. 7,292,742, 7,181,122, 7,013,054, 6,917,726, 7,267,673, and 7,170,050. These and other optical components known in the art can be combined and assembled in a variety of ways to effect detection of distinguishable signals.

Use of Labeled Nucleic Acids

Fluorescently labeled polynucleotides of the invention find use in a variety of applications. Such applications can involve interactions between nucleic acids, e.g., interactions between DNA and DNA, DNA and RNA, and RNA and RNA, or any other non-naturally occurring nucleic acids PNA, LNA, and/or TNA. Various applications can also involve interactions between nucleic acids and proteins, lipids or combinations thereof. Non-limiting examples of specific nucleic acid assays include nucleic acid amplification, both quantitative or end-point amplification, hybridization in solution or on a substrate (e.g., array hybridization), gel shifts, and nucleic acid sequencing. The fluorescently labeled polynucleotides can be used in solution phase or immobilized on a substrate.

In one embodiment, the labeled polynucleotides are used as hybridization probes. One application of hybridization probes is fluorescent in situ hybridization (FISH). In this technique, a labeled polynucleotide complementary to a sequence of interest is annealed to fixed chromosomes preparations, and the presence of the sequence of interest as well as the chromosomal localization is detected by microscopy. FISH can be performed by immobilizing the nucleic acids of interest on a substrate including without limitation glass, silicon, or fiber. FISH may also be used quantitatively (Q-FISH) to detect the presence and length of repetitive sequences such as telomeres. This may be done by quantitating the intensity of emitted fluorescence as measured by microscopy. FISH assays utilizing the subject fluorescent compounds can be performed for detecting a specific segment of a DNA molecule or a chromosome. These features can be used in genetic counseling (e.g., prenatal-screens), medicine, and species identification.

In some embodiments, labeled polynucleotides can be used as primers in amplification reactions such as PCR. In yet another embodiment, a compound of the invention may be used to label a polynucleotide which is subsequently used as a probe may be a hybridization probe or a real-time PCR probe. Such a probe may be labeled with a second fluorescent group to form a FRET pair with the first fluorescent group of the invention. Methods for the preparation and use of PCR probes are well known to one skilled in the art.

In one embodiment of the invention, a method is provided for detecting or quantifying a target nucleic acid, the method comprising the steps of: a) providing a labeled polynucleotide ("probe") of the present invention; b) contacting said labeled polynucleotide with the nucleic acid target so as to allow for hybridization of the probe with the nucleic acid target; and c) detecting or quantifying said nucleic acid target by measuring a change in the fluorescence of the probe upon the hybridization of the nucleic acid probe with the nucleic acid target.

As used herein, hybridization occurs when the probe form a complex with the target nucleic acid. In general, the complex is stabilized, at least in part, via hydrogen bonding between the bases of the nucleotide residues. The hydrogen bonding may occur by Watson-Crick base pairing, Hoogstein binding, or in any other sequence-specific manner. Hybridization may constitute a step in a more extensive process, such as the initiation of a PCR reaction, or the enzymatic cleavage of a polynucleotide by a ribozyme.

After hybridization between the probe and the target has occurred, a change in the intensity of the fluorescence of the probe may be measured. Such change before and after hybridization can yield a positive gain or negative reduction in the detected signal intensity. Depending on the specific hybridization assay that is run, more than one event after hybridization may contribute to the generation of a change in signal intensity. For example, an increase in reporter signal may result by way of spatial extension or separation of the reporter fluorescent group from the quencher group while both are still attached to the probe. In addition, either the reporter or the quencher of the probe can be separated by way of cleavage via an enzyme (e.g., a polymerase having a 5' to 3' exonuclease), thereby generating a reporter signal that is detected. As noted above, both the reporter and the quencher are defined in functional terms, such that these groups can be identical though serving, relative to each other, a different function when used in a hybridization reaction. For example, a group attached to a probe is a quencher because it reduces the emission of an optical signal when the probe is not hybridized with the target nucleic acid (typically when the probe assumes a random state). The same group can become a reporter fluorescent group upon being cleaved by an enzyme after hybridization with the target nucleic acid as the signal of the fluorescent group is now detected during the assay. In some PCR probe design, the oligonucleotide probe may be labeled with two identical dye molecules of the invention according to the US patent application 20050272053, wherein the essentially nonfluorescently labeled probe releases two reporter dyes following 5'-exonuclease-mediated cleavage of the probe during PCR.

The signal detection methods described previously can be applied to nucleic acid amplification in which the target nucleic acid is increased in copy number. Such increase may occur in a linear or in an exponential manner. Amplification may be carried out by natural or recombinant DNA polymerases such as Taq polymerase, Pfu polymerase, T7 DNA polymerase, Klenow fragment of E. coli DNA polymerase, Tma DNA polymerase, exo-Tli DNA polymerase, exo-KOD DNA polymerase, exo-JDF-3 DNA polymerase, exo-PGB-D DNA polymerase, U1Tma (N-truncated) Thermatoga martima DNA polymerase, Sequenase, and/or RNA polymerases such as reverse transcriptase.

A preferred amplification method is polymerase chain reaction (PCR). General procedures for PCR are taught in U.S. Pat. No. 4,683,195 (Mullis) and U.S. Pat. No. 4,683,202 (Mullis et al.). Briefly, amplification of nucleic acids by PCR involves repeated cycles of heat-denaturing the DNA, annealing two primers to sequences that flank the target nucleic acid segment to be amplified, and extending the annealed primers with a polymerase. The primers hybridize to opposite strands of the target nucleic acid and are oriented so that the synthesis by the polymerase proceeds across the segment between the primers, effectively doubling the amount of the target segment. Moreover, because the extension products are also complementary to and capable of binding primers, each successive cycle essentially doubles the amount of target nucleic acids synthesized in the previous cycle. This results in exponential accumulation of the specific target nucleic acids at approximately a rate of $2^n$, where n is the number of cycles.

A typical conventional PCR thermal cycling protocol comprises 30 cycles of (a) denaturation at a range of 90° C. to 95° C. for 0.5 to 1 minute, (b) annealing at a temperature ranging from 50° C. to 65° C. for 1 to 2 minutes, and (c) extension at 68° C. to 75° C. for at least 1 minute. Other protocols including but not limited to universal protocol as well as fast cycling protocol can be performed the subject probes as well.

A variant of the conventional PCR is a reaction termed "Hot Start PCR". Hot Start PCR techniques focus on the inhibition of polymerase activity during reaction preparation. By limiting polymerase activity prior to PCR cycling, non-specific amplification is reduced and the target yield is increased. Common methods for Hot Start PCR include chemical modifications to the polymerase (see, e.g., U.S. Pat. No. 5,773,258), inhibition of the polymerase by a polymerase-specific antibody (see, e.g., U.S. Pat. No. 5,338,671), and introduction of physical barriers in the reaction site to sequester the polymerase before the thermal cycling takes place (e.g., wax-barrier methods). The reagents necessary for performing Hot Start PCR are conveniently packaged in kits that are commercially available (see, e.g., Sigma's JumpStart Kit).

Another variation of the conventional PCR that can be performed with the subject probes is "nested PCR" using nested primers. The method is preferred when the amount of target nucleic acid in a sample is extremely limited for example, where archival, forensic samples are used. In performing nested PCR, the nucleic acid is first amplified with an outer set of primers capable of hybridizing to the sequences flanking a larger segment of the target nucleic acid. This amplification reaction is followed by a second round of amplification cycles using an inner set of primers that hybridizes to target sequences within the large segment.

The subject probes can be employed in reverse transcription PCR reaction (RT-PCR), in which a reverse transcriptase first coverts RNA molecules to double stranded cDNA molecules, which are then employed as the template for subsequent amplification in the polymerase chain reaction. In carrying out RT-PCR, the reverse transcriptase is generally added to the reaction sample after the target nucleic acids are heat denatured. The reaction is then maintained at a suitable temperature (e.g., 30° C.-45° C.) for a sufficient amount of time (e.g., 5-60 minutes) to generate the cDNA template before the scheduled cycles of amplification take place. Such reaction is particularly useful for detecting the biological entity whose genetic information is stored in RNA molecules. Non-limiting examples of this category of biological entities include RNA viruses such as HIV and hepatitis-causing viruses. Another important application of RT-PCR embodied by the present invention is the simultaneous quantification of biological entities based on the mRNA level detected in the test sample.

The subject probes can also be employed to perform ligase chain polymerase chain reaction (LCR-PCR). The method involves ligating the target nucleic acids to a set of primer pairs, each having a target-specific portion and a short anchor sequence unrelated to the target sequences. A second set of primers containing the anchor sequence is then used to amplify the target sequences linked with the first set of primers. Procedures for conducting LCR-PCR are well known to artisans in the field, and hence are not detailed herein (see, e.g., U.S. Pat. No. 5,494,810).

The subject probes are particularly suited for use in a homogeneous assay. In such an assay, a target nucleic acid is detected and/or quantified without the requirement of post-assay processing to record the result of the assay. For example, a homogeneous PCR reaction can be carried out in a closed sample holder (e.g., a tube, a sample capillary or thermalchip), and no further addition or removal of reagents is necessary to record the result once the assay is started. Homogeneous assays allow recordation of the result of the assay in real time. Where desired, in practicing the subject methods, the result of the assay can be continuously recorded as the assay progresses in time or recorded intermittently at one or more point during the assay or upon completion of the assay.

Where desired, homogeneous assays can be multiplexed, i.e., more than one target nucleic acid can be detected in one assay. In a multiplex assay, two or more specific nucleic acid probes, which differ in the nature of their covalently attached fluorescent groups, are added to the mixture to be assayed. The fluorescent groups are chosen to produce distinguishable fluorescent signals from each specific nucleic acid probe. The signals of the different fluorescent group combinations of the nucleic acid probes can be recorded simultaneously to detect and/or quantify the corresponding target nucleic acids. Multiplexing greatly reduces the cost of analysis and can tremendously increase throughput in high volume settings.

The subject probes can be used to detect single mutations. Accordingly, methods are provided to use the probes of the invention to detect as few as a single mismatch between the probe sequence and a target sequence. Such high specificity in nucleic acid detection by PCR is highly valuable in clinical diagnosis and genetic research. For example, many diseases are associated with single mutations at different sites in the human genome. Although in theory this type of genetic variations, also called single nucleotide polymorphism or SNP, may be detected by sequencing, such sequencing method is not expected to be practical on a large scale due to high cost and low efficiency. Detection of SNP by an amplification reaction is feasible with the use of the subject probes.

The subject probes are also particularly suited for monitoring nucleic acid amplification reactions. In a related embodiment, the present invention provides a method of monitoring the increase in a target nucleic acid during amplification of said target. The method typically involves a) providing an amplification reaction mixture that comprises said target nucleic acid, at least one primer that hybridizes to the target nucleic acid, a labeled oligonucleotide probe of the present invention that provides a detectable signal, the intensity of which is proportional to the increase in the target nucleic acid in the amplification; (b) treating said mixture under conditions for amplifying said target nucleic acid; and (c) measuring the amount of said signal produced by said mixture during said treating step (c). Where desired, the amount of signal is determined continuously throughout the amplification reaction or determined intermittently during the amplification reaction. The amplification can be exponentially with the use of a primer pair or linearly with the use of one primer of the pair.

The increase in signal intensity during the amplification reaction may due to the step of hybridization of the probe to the target nucleic acid and also the step of cleavage via the action of the polymerase utilized in the amplification reaction.

In one aspect, the subject methods exploit the 5' to 3' nuclease activity of a polymerase when used in conjunction with PCR. When the subject probe is added concomitantly with the primer at the start of PCR, and the signal generated from hydrolysis of the labeled nucleotide(s) of the probe provides a means for detection of the target sequence during its amplification. Numerous polymerases are suited to catalyze primer and template-dependent nucleic acid synthesis and possess the 5' to 3' nuclease activity. Non-limiting examples include DNA polymerases such as *E. coli* DNA polymerase I, *Thermus thermophilus* (Tth) DNA polymerase, *Bacillus stearothermophilus* DNA polymerase, *Thermococcus littoralis* DNA polymerase, and *Thermus aquaticus* (Taq) DNA polymerase. Where desired, temperature stable polymerases can be employed in a nucleic acid amplification reaction. See, e.g., U.S. Pat. No. 4,889,818 that discloses a representative thermostable enzyme isolated from *Thermus aquaticus*. Additional representative temperature stable polymerases include without limitation, e.g., polymerases extracted from the thermostable bacteria *Thermus flavus*, *Thermus ruber*, *Thermus thermophilus*, *Bacillus stearothermophilus* (which has a somewhat lower temperature optimum than the others listed), *Thermus lacteus*, *Thermus rubens*, *Thermotoga maritima*, *Thermococcus littoralis*, and *Methanothermus fervidus*.

In another embodiment, nucleic acid amplification can be performed with polymerases that exhibit strand-displacement activity (also known as rolling circle polymerization). Strand displacement can result in the synthesis of tandem copies of a circular DNA template, and is particularly useful in isothermal PCR reaction. Non-limiting examples of rolling circle polymerases suitable for the present invention include but are not limited to T5 DNA polymerase (Chatterjee et al., Gene 97:13-19 (1991)), and T4 DNA polymerase holoenzyme (Kaboord and Benkovic, Curr. Biol. 5:149-157 (1995)), phage M2 DNA polymerase (Matsumoto et al., Gene 84:247 (1989)), phage PRD1 DNA polymerase (Jung et al., Proc. Natl. Aced. Sci. USA 84:8287 (1987), and Zhu and Ito, Biochim. Biophys. Acta. 1219:267-276 (1994)), Klenow fragment of DNA polymerase I (Jacobsen et al., Eur. J. Biochem. 45:623-627 (1974)).

A preferred class of rolling circle polymerases utilizes protein priming as a way of initiating replication. Exemplary polymerases of this class are modified and unmodified DNA polymerase, chosen or derived from the phages Φ29, PRD1, Cp-1, Cp-5, Cp-7, Φ15, Φ1, Φ21, Φ25, BS 32 L17, PZE, PZA, Nf, M2Y (or M2), PR4, PR5, PR722, B 103, SF5, GA-1, and related members of the Podoviridae family. Specifically, the wildtype bacteriophage Φ29 genome consists of a linear double-stranded DNA (dsDNA) of 19,285 base pairs, having a terminal protein (TP) covalently linked to each 5'end. To initiate replication, a histone-like viral protein forms anucleoprotein complex with the origins of replication that likely contributes to the unwinding of the double helix at both DNA ends (Serrano et al., The EMBO Journal 16(9): 2519-2527 (1997)). The DNA polymerase catalyses the addition of the first dAMP to the hydroxyl group provided by the TP. This protein-primed event occurs opposite to the second 3' nucleotide of the template, and the initiation product (TP-dAMP) slides back one position in the DNA to recover the terminal nucleotide After initiation, the same DNA polymerase replicates one of the DNA strands while displacing the other. The high processivity and strand displacement ability of Φ29 DNA polymerase makes it possible to complete replication of the Φ29 TP-containing genome (TP-DNA) in the absence of any helicase or accessory processivity factors (reviewed by Serrano et al., The EMBO Journal 16(9): 2519-2527 (1997)).

Strand displacement can be enhanced through the use of a variety of accessory proteins. They include but are not limited to helicases (Siegel et al., J. BioL Chem. 267:13629-13635 (1992)), herpes simplex viral protein ICP8 (Skaliter and Lehman, Proc. Natl, Acad. Sci. USA 91(22): 10665-10669 (1994)), single-stranded DNA binding proteins (Rigler and Romano, J. Biol. Chem. 270:8910-8919 (1995)), adenovirus DNA-binding protein (Zijderveld and van der Vliet, J. Virology 68(2): 1158-1164 (1994)), and BMRF1 polymerase accessory subunit (Tsurumi et al., J. Virology 67(12):7648-7653 (1993)).

The subject probes can be utilized in an isothermal amplification reaction. Such amplification reaction does not rely solely upon thermal cycling. The procedure can be applied at a wide range of ambient temperatures. In particular, denaturation of the double-stranded template sequence is not accomplished solely through an increase in temperature above the melting temperature of the double stranded sequence. Rather, the denaturation process involves physical or mechanical force that separates the strand to allow primer annealing and extension. Various mechanisms for conducting isothermal amplification reaction including isothermal PCR are described in US. Patent Publication No 20060019274 and U.S. Pat. Nos. 5,824,477 and 6,033,850, which are incorporated herein by reference.

Nucleic acid amplification is generally performed with the use of amplification reagents. Amplification reagents typically include enzymes, aqueous buffers, salts, primers, target nucleic acid, and nucleoside triphosphates. Depending upon the context, amplification reagents can be either a complete or incomplete amplification reaction mixture.

The choice of primers for use in nucleic acid amplification will depend on the target nucleic acid sequence. Primers used in the present invention are generally oligonucleotides, e.g., 10 to 100 or 10 to 25 bases in length, that can be extended in a template-specific manner via the action of a polymerase. In general, the following factors are considered in primer design: a) each individual primer of a pair preferably does not self-hybridize in an amplification reaction; b) the individual pairs preferably do not cross-hybridize in an amplification reaction; and c) the selected pair must have the appropriate length and sequence homology in order to anneal to two distinct regions flanking the nucleic acid segment to be amplified. However, not every nucleotide of the primer must anneal to the template for extension to occur. The primer sequence need not reflect the exact sequence of the target nucleic acid. For example, a non-complementary nucleotide fragment may be attached to the 5' end of the primer with the remainder of the primer sequence being complementary to the target. Alternatively, non-complementary bases can be interspersed into the primer, provided that the primer sequence has sufficient complementarily with the target for annealing to occur and allow synthesis of a complementary nucleic acid strand.

A nucleic acid amplification reaction typically comprises a target nucleic acid in a buffer compatible with the enzymes used to amplify the target. The buffer typically contains nucleotides or nucleotide analogs (ATP, TTP, CTP, GTP, or analogs thereof including without limitation pentaphosphates having the respective base unit) that are capable of being incorporated into a replica strand of the template sequence.

Where desired, amplification reaction is carried out as an automated process. Numerous thermocyclers are available in the art that are capable of holding 48, 96 or more samples. A suitable optical system moves the excitation light from the source to the reaction sites and measures the emission light from each sample. For example, multiple fiber optic leads simultaneously read all PCR tubes undergoing thermocycling. However, only a single fluorometer may be needed to read fluorescence from the reaction sites. An analogous detection scheme is suitable in a 96-well microtiter format. This type of format is frequently desirable in clinical laboratories for large scale sample screening, for example, for genetic analysis such as screening for AIDS virus in blood bank screening procedures.

Accordingly, the present invention also provides an apparatus for detecting the signal generated by the subject probe, which can be used to detect, measure, and quantify the signal before, during, and after amplification. The apparatus comprises a thermal unit (e.g., a thermocycler) capable of holding an amplification reaction mixture comprising the subject probes and effecting an amplification of the target sequence, and a detector that detects the signal generated from the subject probes.

In another embodiment of the present invention, the subject probes are employed in assays that are conducted on nucleic acid microarrays to detect or quantify nucleic acid targets. In such assays, a fluorescent signal is generated on a nucleic acid microarray upon the presence of a complementary target nucleic acid.

Nucleic acid microarrays including gene chips comprise ordered arrays of nucleic acids that are covalently attached to a solid surface, see e.g., U.S. Pat. Nos. 5,871,928, 6,040,193, 6,262,776, 6,403,320, and 6,576,424. The fluorescent signal that is generated in the assay can be monitored and quantified with optical detectors including but not limited to fluorescence imagers, e.g. commercial instruments supplied by Hitachi Corp., San Bruno, Calif. or confocal laser microscopes (confocal fluorescence scanners), e.g. commercial instruments from General Scanning, Inc., Watertown, Mass.

In assays that are conducted on nucleic acid microarrays, the target nucleic acids may be provided as a mixture of nucleic acid sequences derived from any suitable biological sources. They can be derived from body fluid, solid tissue samples, tissue cultures or cells derived therefrom and the progeny thereof, and sections or smears prepared from any of these sources, or any other samples that contain nucleic acids.

Where expression pattern is assayed, the mRNA sequences are first typically amplified by reverse transcription PCR with universal primers prior to their use as the target sequences in the assay. In one embodiment, all nucleic acid sequences present in the test sample are simultaneously applied to the microarray for analysis, thus allowing the interaction of all target nucleic acid sequences with all nucleic acids that are present on the array. In another embodiment, the target nucleic acids applied to the array are pre-selected to yield a subset for refined hybridization analysis utilizing a microarray. For example, a limited number of target sequences can contain more than one stretch of specific nucleotide sequence to be analyzed, e.g. more than one single nucleotide polymorphism. The nucleic acid sequences of this setting may be amplified by PCR with the aid of specific primers prior to their analysis on the microarray.

In assaying for expression of multiples genes of a subject, target polynucleotides are allowed to form stable complexes with probes on the aforementioned arrays in a hybridization reaction. It will be appreciated by one of skill in the art that where antisense RNA is used as the target nucleic acid, the sequence immobilized on the array are chosen to be complementary to sequences of the antisense nucleic acids. Conversely, where the target nucleic acid pool is a pool of sense nucleic acids, the sequence immobilized on the array are selected to be complementary to sequences of the sense nucleic acids. Finally, where the nucleic acid pool is double stranded, the probes may be of either sense and/or antisense as the target nucleic acids include both sense and antisense strands.

In one embodiment, labeled probes are utilized to perform a competitive hybridization on a microarray. In this assay format, a target nucleic acid from a test sample competes with a probe of the present invention for binding of a known sequence immobilized on the microarray. The amount of labeled probes that will bind to the immobilized known sequences is inversely proportional to the concentration of corresponding target nucleic acids in the test sample.

A variant hybridization assay involves the use of polymerases on a microarray to enhance the signals of the probes by performing cleavage of the reporters. For example, a mixture of target sequences are first allowed to hybridize with known sequences immobilized on the array. Unhybridized sequences are then washed away. Thereafter, probes corresponding to the target sequences are allowed to hybridize to different regions on the targets. Upon washing of the excessive unbound probes, the reporter fluorescent groups on the hybridized probes are cleaved via the action of polymerases, thereby generating a detectable signal that is indicative of the presence and/or quantity of a target sequence initially present in the test sample.

Suitable hybridization conditions for use of the labeled probes of the invention are such that the recognition interaction between the sequence on the array and target is both sufficiently specific and sufficiently stable. As noted above, hybridization reactions can be performed under conditions of different "stringency". Relevant conditions include temperature, ionic strength, time of incubation, the presence of additional solutes in the reaction mixture such as formamide, and the washing procedure. Higher stringency conditions are those conditions, such as higher temperature and lower sodium ion concentration, which require higher minimum complementarity between hybridizing elements for a stable hybridization complex to form. Conditions that increase the stringency of a hybridization reaction are widely known and published in the art. See, for example, (Sambrook, et al., (1989), supra).

In general, there is a tradeoff between hybridization specificity (stringency) and signal intensity. In a preferred embodiment, washing the hybridized array prior to detecting the target-probe complexes is performed to enhance the signal to noise ratio. Typically, the hybridized array is washed at successively higher stringency solutions and signals are read between each wash. Analysis of the data sets thus produced will reveal a wash stringency above which the hybridization pattern is not appreciably altered and which provides adequate signal for the particular polynucleotide probes of interest. Parameters governing the wash stringency are generally the same as those of hybridization stringency. Other measures such as inclusion of blocking reagents (e.g. sperm DNA, detergent or other organic or inorganic substances) during hybridization can also reduce non-specific binding.

Imaging specific hybridization event on a microarray is typically performed with the aid of an optical system. Non-limiting examples of suitable systems include camera, charge couple device (CCD), electron-multiplying charge-coupled device (EMCCD), intensified charge coupled device (ICCD), and confocal microscope.

The microarray provides a positional localization of the sequence where hybridization has taken place. The position of the hybridized region correlates to the specific sequence, and hence the identity of the target expressed in the test sample. The detection methods also yield quantitative measurement of the level of hybridization intensity at each hybridized region, and thus a direct measurement of the level of expression of a given gene transcript. A collection of the data indicating the regions of hybridization present on an array and their respective intensities constitutes a hybridization pattern that is representative of a multiplicity of expressed gene transcripts of a subject. Any discrepancies detected in the hybridization patterns generated by hybridizing target polynucleotides derived from different subjects are indicative of differential expression of a multiplicity of gene transcripts of these subjects.

In one aspect, the hybridization patterns to be compared can be generated on the same array. In such case, different patterns are distinguished by the distinct types of detectable labels. In a separate aspect, the hybridization patterns employed for the comparison are generated on different arrays, where discrepancies are indicative of a differential expression of a particular gene in the subjects being compared.

The test nucleic acids for a comparative hybridization analysis can be derived from (a) cells from different organisms of the same species (e.g. cells derived from different humans); (b) cells derived from the same organism but from different tissue types including normal or disease tissues, embryonic or adult tissues; (c) cells at different points in the cell-cycle; (d) cells treated with or without external or internal stimuli. Thus, the comparative hybridization analysis using the arrays of the present invention can be employed to monitor gene expression in a wide variety of contexts. Such analysis may be extended to detecting differential expression of genes between diseased and normal tissues, among different types of tissues and cells, amongst cells at different cell-cycle points or at different developmental stages, and amongst cells that are subjected to various environmental stimuli or lead drugs. Therefore, the expression detecting methods of this invention may be used in a wide variety of circumstances including detection of disease, identification and quantification of differential gene expression between at least two samples, linking the differentially expressed genes to a specific chromosomal location, and/or screening for compositions that upregulate or downregulate the expression or alter the pattern of expression of particular genes.

The subject amplification and any other hybridization assays described herein can be used to detect any target nucleic acids from any sources suspected to contain the target. It is not intended to be limited as regards to the source of the sample or the manner in which it is made. Generally, the test sample can be biological and/or environmental samples. Biological samples may be derived from human or other animals, body fluid, solid tissue samples, tissue cultures or cells derived therefrom and the progeny thereof, sections or smears prepared from any of these sources, or any other samples that contain nucleic acids. Preferred biological samples are body fluids including but not limited to urine, blood, cerebrospinal fluid, spinal fluid, sinovial fluid, semen, ammoniac fluid, cerebrospinal fluid (CSF), and saliva. Other types of biological sample may include food products and ingredients such as dairy items, vegetables, meat and meat by-products, and waste. Environmental samples are derived from environmental material including but not limited to soil, water, sewage, cosmetic, agricultural and industrial samples, as well as samples obtained from food and dairy processing instruments, apparatus, equipment, disposable, and non-disposable items.

Polynucleotides labeled according to the invention may also be used in gel shift assays. Such an assay, also known as electrophoretic mobility shift assay (EMSA), gel mobility shift assay, band shift assay, or gel retardation assay, is a common technique used to study protein-DNA or protein-RNA interactions. This procedure can determine if a protein or mixture of proteins is capable of binding to a given DNA or RNA sequence, and can sometimes indicate if more than one protein molecule is involved in the binding complex. Labeled oligonucleotides may be used in gel shift assays by peforming electrophoresis and subsequently determining the extent of migration of the labeled oligonucleotides in the gel by visualizing the emission of the fluorescent label. Gel shift assays may be performed in vitro concurrently with DNase footprinting, primer extension, and promoter-probe experiments when studying transcription initiation, DNA replication, DNA repair or RNA processing and maturation. Methods of performing gel shift assays are known. See, e.g. Garner, M. M. and Revzin, A. (1981) "A gel electrophoresis method for quantifying the binding of proteins to specific DNA regions: application to components of the *Escherichia coli* lactose operon regulatory system." Nucleic Acids Res. 9:3047-3060 or Fried, M. and Crothers, D. M. (1981) "Equilibria and kinetics of lac repressor-operator interactions by polyacrylamide gel electrophoresis." Nucleic Acids Res., 9:6505-6525.

Use of Labeled Polypeptides

Fluorescently labeled polypeptides of the invention are useful in a wide variety of assays. Such assays can be performed to discern specific protein-protein interactions, protein-nucleic acid interaction, interactions between a protein of interest and candidate inhibitors or activators. Candidate inhibitors or activators include but are not limited to antisense oligonucleotides, double stranded RNAs, ribozymes, a ribozyme derivatives, antibodies, liposomes, small molecules, inorganic or organic compounds. The subject assays can also be performed to study enzymatic kinetics, for e.g., drug design, screen and/or optimization and can be performed using the fluorescently labeled polypeptides in solution or immobilized on a solid substrate.

Of particular interest is a specific interaction between a cell surface receptor and its corresponding ligand. Cell surface receptors are molecules anchored on or inserted into the cell plasma membrane. They constitute a large family of proteins, glycoproteins, polysaccharides and lipids, which serve not only as structural constituents of the plasma membrane, but also as regulatory elements governing a variety of biological functions. In another aspect, the specific protein-protein interaction involves a cell surface receptor and an immunoliposome or an immunotoxin. In yet another aspect, the specific protein-protein interaction may involve a cytosolic protein, a nuclear protein, a chaperon protein, or proteins anchored on other intracellular membranous structures. In yet another aspect, the specific protein-protein interaction is between a target protein (e.g., an antigen) and an antibody specific for that antigen.

A specific interaction between a labeled polypeptide and an interacting entity is assayed by mixing the two entities under conditions such interaction is suspected to occur. Typically, the interaction is visualized with the aid of an optical device. Where desired, these entities can be placed within an optical confinement (see, e.g., U.S. Pat. Nos. 7,267,673, and 7,170,050). Where single molecule is to be detected, each optical confinement contains only one target that is being investigated. This can be achieved by diluting a minute amount of target in a large volume of solution, such that deposition over an array of confinements results in a primary distribution, or a majority of confinements will have a single target molecule disposed there. The labeled polypeptide and the interacting entity can be immobilized onto the inner surface of the optical confinement by any of the methods available in the art. Such methods encompass the uses of covalent and noncovalent attachments effected by a variety of binding moieties. The choice of the binding moieties will depend on the nature of the labeled polypeptide and/or the interacting entity. One way to immobilize the labeled polypeptide or the proteinaceous probe involves the use of the streptavidin or avidin/biotin binding pair.

In one embodiment, the polypeptide to be reacted with a compound of the invention comprises 3 to about 80 amino acids. Examples of such polypeptides include, but are not limited to, neuropeptides, cytokines, toxins and peptidase or protease substrates. Fluorescently labeled-neuropeptides, -cytokines and -toxins may be used to map or visualize the distribution of the receptors specific to the respective peptides. As an example, when labeled with a compound of the invention, phalloidin, which is a toxin with a cyclic peptide structure, can be used to stain F-actin filaments in cells. As another example, when labeled with a fluorescent group of the invention, α-bungarotoxin, a peptide-based snake toxin, can be used to detect acetylcholine receptor. Peptidase or protease substrates labeled with a fluorescent group of the invention may be used to assay the activities of the peptidases or proteases, and used in screening drugs designed as inhibitors of the peptidases or proteases. For example, a peptide comprising a peptide sequence cleavable by a peptidase may be labeled at one end of the peptide sequence with a first fluorescent group, a fluorescence donor fluorescent group, selected from a fluorescent group of the invention and at the other end of the peptide sequence with a second fluorescent group, a fluorescence acceptor fluorescent group (such as another fluorescent group from the invention or a quencher), where the first dye and second dye form a fluorescence resonance energy transfer (FRET) pair. By detecting the fluorescence difference of either the donor fluorescent group or the acceptor fluorescent group of the FRET pair before and after the peptide is cleaved by said peptidase, the level of enzyme activity can be assessed.

Other polypeptide conjugates that can be prepared according to the invention include those of antibodies, lectins, enzymes, lipoproteins, albumins, avidin, streptavidin, annexins, protein A, protein G, transferrin, apotransferrin, phycobiliproteins and other fluorescent proteins, toxins, growth factors, tubulins, hormones, various receptors and ion channels.

In one embodiment, compounds of the invention may be reacted with antibodies. Such antibodies may be primary or secondary depending on the desired application. If the antigen to be detected is present in very small amounts, a secondary antibody may be used in order to provide signal amplification. Various secondary antibody isotypes may be labeled. Non-limiting examples of secondary antibody isotypes are Anti-mouse IgG, Anti-mouse IgM, Anti-rabbit IgG, Anti-rat IgG, Anti-rat IgM, Anti-guinea pig IgG, Anti-chicken IgG, Anti-hamster IgG, Anti-human IgG, Anti-human IgM, Anti-goat IgG, Anti-mouse IgG, Anti-rabbit IgG, Anti-rat IgG, Anti-sheep IgG, Anti-goat IgG, Anti-mouse IgG, Anti-human IgG, Anti-rat IgG, Anti-mouse IgG, Anti-human IgG, Anti-rat IgG, Anti-goat IgG, and Anti-rabbit IgG.

Alternatively, Fab fragments may be labeled with the compounds of the invention. Such fragments may be superior to whole antibody conjugates because they lack the Fc region, which would reduce nonspecific interactions with Fc receptor-bearing cell membranes and would allow better penetration into tissues.

Labeled secondary antibodies of the invention may be used in signal amplification kits such as those commercialized by Molecular Probes, Inc. Such kits could each provide two labeled antibodies specific to a primary antibodies, such as a mouse antibody. In one embodiment, a rabbit anti-mouse IgG antibody conjugate of the invention is first used to bind to the mouse-derived primary antibody. The fluorescence is then dramatically enhanced by the addition of a second conjugate of a goat anti-rabbit IgG antibody.

In yet another embodiment, the compounds of the invention may be used to label protein A and/or protein G. Protein A and protein G are bacterial proteins that bind with high affinity to the Fc portion of various classes and subclasses of immunoglobulins from a variety of species, such as Bovine, Cat, Chicken, Dog, Goat, Guinea pig, Horse, Human IgG1, IgG2, IgG3, IgG4, Human IgM, IgA, IgE, Human IgD, Mouse IgG1 or others, Pig, Rabbit, Rat or Sheep, which may be used in the detection of immunoglobulins. Alternatively, immunoglobins can be labeled with a compound of the invention having a structure of Formula I, II, III, IV, or V and retains binding specificity to its target after such labeling. These labeled immunoglobins can be used for in-vitro or in-vivo detection of the target antigen of the immunoglobin. In some embodiments, the labeled immunoglobins comprise a fluorophore that has an absorption maximal wavelength equal to or greater than 750 nm. In other embodiments labeled immunoglobins comprise a fluorophore that has an absorption maximal wavelength equal to or greater than 685 nm, In various embodiments of the invention, such labeled immunoglobins bind to an antigen on a cancer cell. In some embodiments, the labeled immunoglobin binds to erb2.

Labeled antibodies prepared according to the invention may be primary antibodies for various applications. While secondary detection methods can provide significant signal amplification, a directly labeled primary antibody often produces lower background fluorescence and less nonspecific binding. Using primary antibodies also allows multiple primary antibodies of the same isotype or derived from the same species to be used in the same experiment when they are directly labeled.

Examples of such primary antibodies include polyclonal antibodies specific for reporter gene products. These include Anti-Green-Fluorescent Protein Antibodies, Anti-Glutathione S-Transferase Antibody, Anti-beta-Glucuronidase Antibody, Anti-beta-Galactosidase Antibody, Monoclonal Antibodies Specific for Epitope Tags, Penta-His Antibody, Anti-HA Antibody and Anti-c-myc Antibody.

Organelle-specific labeled antibodies may also be prepared to label various subcellular organelles and components such as the endoplasmic reticulum, peroxisomes, mitochondria, or cytochrome c. Labeled antibodies may also be specific for proteins in the oxidative phosphorylation system, such as antibodies against cytochrome oxidase (Complex IV) or antibodies against Complexes I, II, III and V, or other mitochondrial proteins such as anti-mitochondrial porin antibodies or anti-pyruvate dehydrogenase antibodies.

In other embodiments, labeled antibodies specific for proliferation markers and cell-cycle control proteins may be prepared. Such antibodies include Anti-Bromodeoxyuridine Antibody (Anti-BrdU Antibody), which may for example be used in TUNEL assays, Anti-Human mRNA-Binding Protein HuR Antibody (Anti-HuR Antibody), Anti-Human Neuronal Protein HuC/HuD Antibody (Anti-Hu Antibody), Anti-cdc6 Peptide Antibody, Anti-CD Antibodies, Antibodies against D Cyclins/Cyclin-Dependent Kinase Inhibitors, and Anti-Phosphoinositide Antibodies.

Some labeled antibodies may be specific for structural cellular proteins. Examples of such antibodies are Anti-alpha-Tubulin Monoclonal Antibody, Anti-Glial Fibrillary Acidic Protein (GFAP) Antibody, Anti-Desmin Antibody, or Anti-Fibronectin Antibody. Additional antibodies suitable for use in the invention include antibodies specific for neuronal proteins such as Anti-Synapsin I Antibody or Anti-NMDA Receptor Antibodies. Other Polyclonal and Monoclonal Antibodies that may be labeled according to the invention include Anti-Human Golgin-97 Antibody, Anti-Human Transferrin Receptor Antibody, Antibodies against Matrix Metalloproteinases and Anti-Bovine Serum Albumin Antibody.

The specific interaction between an antigen and an antibody has been explored in the context of immunoassays utilizing the subject fluorescent compounds. The immunoassays can permit single-molecule detection or ensemble detection. The subject immunoassays can be performed to characterize biological entities, screen for antibody therapeutics, and determine the structural conformations of a target antigen. For instance, immunoassays involving antibodies that are specific for the biological entity or specific for a by-product produced by the biological entity have been routinely used to identify the entity by forming an antibody-entity complex. Immunoassays are also employed to screen for antibodies capable of activating or down-regulating the biological activity of a target antigen of therapeutic potential. Immunoassays are also useful for determining structural conformations by using anti-idotypic antibodies capable of differentiating target proteins folded in different conformations.

According to one embodiment of the invention, biomolecules labeled with a fluorescent group of the invention such as proteins are suitable for in vivo imaging, including without limitation imaging a cell, tissue, organ or a whole subject. The fluorescent groups of the invention and/or the labeled biomolecules of the present invention can be administered to a subject in a variety of forms adapted to the chosen route of administration, i.e., orally, or parenterally. Parenteral administration in this respect includes, but is not limited to, administration by the following routes: intravenous, intramuscular, subcutaneous, parenteral, intraocular, intrasynovial, transepithelially including transdermal, opthalmic, sublingual, and buccal; topically including opthalmic, dermal, ocular, rectal and nasal inhalation via insufflation and aerosol and rectal systemic. In particular, proteins labeled with a fluorescent group of the invention comprising an mPEG as a water soluble polymer group may be advantageous. In vivo imaging may provide means for early detection, screening, diagnosis, image-guided surgical intervention, and treatment of various diseases. For example, Near IR fluorescent group-labeled toxin (Veiseh, et al. Cancer Res. 67(14), 6882 (2007)) and antibody (Kulbersh, et al. *Arch Otolaryngol Head Neck Surg.* 133(5), 511 (2007) have been used to detect and guide the surgical removal of tumors. In in-vivo imaging, a fluorescent probe, such as an antibody labeled with a fluorescent group, is first administered to an animal (such as a mammal). The animal is then imaged by applying an excitation light with a wavelength appropriate for the absorption of the fluorescent group and collecting the fluorescence signal at another wavelength appropriate for the emission of the fluorescent group. Typically, for efficient tissue penetration of both the excitation and emission lights, the absorption and emission wavelengths of the fluorescent group may be greater than 470 nm, greater than 550 nm, greater than 600 nm, or greater than 640 nm. Absorption and emission wavelengths may be less than 1,200 nm. Fluorescent groups with wavelengths in the 640 nm-1,200 nm range may be referred to as near infrared dyes, or near IR dyes, which are preferred for tissue or in vivo imaging. An important challenge for in vivo imaging using antibodies has been the relatively short half-life of the fluorescently labeled antibodies. It has been reported that antibodies labeled with more than 3 fluorescent group molecules were rapidly cleared from the body by translocating into the liver, where they became metabolized (BioProbes 52, 10-11, March 2007, by Molecular Probes, Inc). In order to extend the half-life of the labeled antibodies so that enough of the antibodies were available over time for detecting the target, it was necessary to lower the number of fluorescent group molecules per antibody (i.e., degree of labeling or DOL) to about 2. However, the lowering of DOL was obtained at the expense of fluorescence brightness of the individual labeled antibody molecules. Thus, it would be desirable to have antibodies that are labeled with 3 or more fluorescent group molecules and that have a relatively long half-life in vivo. PEG is a known biocompatible material often used in functionalizing the surface of implantable medical devices (Balakrishanan, et al. Biomaterials 26(17), 3495 (2005)) and in modifying drugs (Mehvar, et al. Pharm. Pharmaceut. Sci. 3, 125(2000); Wang, et al. J. Biochem. Cell Biology 34, 396(2002)). In practice of the subject invention, proteins, such as antibodies, may be labeled with single or multiple, such as more than 3, 4, 5, 6 or more fluorescent dye molecules of the invention and the antibodies labeled in such a manner can have a relatively long half-life in the body. In particular, the PEG group(s) in the fluorescent group can mask the fluorescent group such that an antibody labeled with multiple molecules of the fluorescent group is less immunogenic as compare to the same antibody labeled with a conventional fluorescent dye (such as Cy5.5, Cy7 or Alexa Fluor 750). In some aspects, PEG group(s) on the fluorescent group can mask or protect the antibody itself, making the antibody more resistant to hydrolysis by proteases.

In other embodiments of the invention, a method of in-vivo imaging of a subject is provided comprising the steps of administering to a subject in need thereof a biomolecule comprising a label having at least one PEG moiety and/or at least one —$SO_3^-$ wherein the at least one reactive moiety of label has undergone a reaction which attached the label to the biomolecule and wherein the biomolecule further comprises a targeting moiety that binds to a binding partner on a cell of the subject which is indicative of the cell; binding the binding partner on the cell with the targeting moiety of the biomolecule thereby differentially labeling the cell relative to neighboring cells; directing exciting wavelength to the cell; and detecting emitted fluorescence from the cell of the subject thereby detecting the differentially labeled cell of the subject. The biomolecule may be an antibody, fragment of an antibody, protein, peptide, lipid or carbohydrate.

The compounds of the invention may also be used to produce labeled biomolecules for use in immunohistochemistry and immunocytochemistry experiments. In immunohistochemistry (IHC), the presence and location of proteins is determined within a tissue section by exploiting the principle of an antibody binding specifically to an antigens present in a biological tissue. Such experiments may, for example, be used in the diagnosis and treatment of cancer. Specific molecular markers are characteristic of particular cancer types and are known to persons skilled in the art. IHC can also be used in basic research to determine the distribution and localization of biomarkers in different parts of a tissue. Visualization of antibody-antigen interactions can be accomplished by reacting an antibody with a reactive fluorescent compound of the invention and using the labeled antibody to stain tissue sections. In immunocytochemistry, the labeled antibody is used to stain populations of cultured cells. These techniques can be combined with confocal laser scanning microscopy, which is highly sensitive and can also be used to visualise interactions between multiple proteins. Subcellular localization of proteins may also be possible using confocal microscopy.

Of particular interest is the use of the labeled polypeptide for conducting immunocytochemistry. Fluorescence immunocytochemistry combined with fluorescence microscopy provides visualization of biomolecules such as proteins and nucleic acids within a cell. One method uses primary antibodies hybridized to the desired target. Then, secondary antibodies conjugated with the subject fluorescent dyes and targeted to the primary antibodies are used to tag the complex. The complex is visualized by exciting the dyes with a wavelength of light matched to the dye's excitation spectrum.

Immunocytochemistry can also be employed to discern subcellular localization of a given protein or nucleic acid. For instance, colocalization of biomolecules in a cell is performed using different sets of antibodies for each cellular target. For example, one cellular component can be targeted with a mouse monoclonal antibody and another component with a rabbit polyclonal antibody. These are designated as the primary antibody. Subsequently, secondary antibodies to the mouse antibody or the rabbit antibody, conjugated to different fluorescent dyes of the present invention having different emission wavelengths, are used to visualize the cellular target.

The compounds of the invention or the covalently labeled biomolecules of the invention can also be used to label cells or particles for a variety of applications. Accordingly, the present invention provides a method of individually labeling a cell within a population of cells whereby the cell is differentially labeled relative to neighboring cells within the population. The method typically comprises contacting the cell with a labeled biomolecule of the present invention, wherein said biomolecule comprises a targeting moiety that binds to a binding partner that is indicative of said cell, and thereby differentially labeling the cell relative to neighboring cells within the population. The targeting moiety can be any biomolecules that recognize a binding partner on the cell to be detected. The choice of the targeting moiety will vary depending on the cell that is to be labeled. For example, for detecting a cancer cell, a targeting moiety is selected such that its binding partner is differentially expressed on a cancer cell. A vast number of cancer markers are known in the art. They include without limitation cell surface receptors such as erb2, PDGF receptor, VEGF receptors, a host of intracellular proteins such as phosphatidylinositol 3-kinases, c-ab1, raf, ras, as well as a host of nuclear proteins including transcription factors and other nucleic acid binding molecules. In some other embodiments, the cancer marker is Immunoglobulin epsilon Fc receptor II, Alk-1, CD20, EGF receptor, FGF receptor, NGF receptor, EpCam, CD3, CD4, CD11a, CD19, CD22, CD30, CD33, CD38, CD40, CD51, CD55, CD80, CD95, CCR2, CCR3, CCR4, CCR5, CTLA-4, Mucin 1, Mucin 16, Endoglin, Mesothelin receptor, Nogo receptor, folate receptor, CXCR4, insulin-like growth factor receptor, Ganglioside GD3, and alpha or beta Integrins. To differentially label various cell types, targeting moieties recognizing a cell-specific binding partner can be used. For example, there are a host of protein markers differentially expressed on T cells as opposed on B cells or other cells of different lineage. Neuronal markers, muscle cell markers, as well as markers indicative of cells of ectodermal, mesodermal or endodermal origins are also known in the art, all of which can be used depending on the intended applications. The targeting moieties can be antibodies, receptors, cytokines, growth factors, and any other moieties or combinations thereof that are recognized by a binding partner on the cell to be labeled. The cell which is labeled may be labeled intracellularly.

The differentially labeled cells can be imaged by directing exciting wavelength to the cell and detecting emitted fluorescence from the cell, in a number of in-vitro formats, either in solution or immobilized on a substrate.

The labeled cells and/or the intensity of the fluorescence may be detected or quantified by performing flow cytometry. Cells or particles labeled with the compounds of the invention or stained with labeled biomolecules of the invention may also be separated and isolated based on the specific properties of the label using fluorescence activated cell sorting (FACS). Such techniques are known in the art. Briefly, cells are labeled with a subject fluorescent dye and then passed, in a suspending medium, through a narrow dropping nozzle so that each cell is typically in a small droplet. A laser based detector system is used to excite fluorescence and droplets with positively fluorescent cells are given an electric charge. Charged and uncharged droplets are separated as they fall between charged plates and so collect in different tubes. The machine can be used either as an analytical tool, counting the number of labeled cells in a population or to separate the cells for subsequent growth of the selected population. Further sophistication can be built into the system by using a second laser system at right angles to the first to look at a second fluorescent label or to gauge cell size on the basis of light scatter.

Additional guidance for performing fluorescent cell sorting can be found in publications such as the following: Darzynkiewicz, Z., Crissman, H. A. and Robinson, J. P., Eds., Cytometry, Third Edition Parts A and B (Methods in Cell Biology, Volumes 63 and 64), Academic Press (2001); Davey, H. M. and Kell, D. B., "Flow cytometry and cell sorting of heterogeneous microbial populations: the importance of single-cell analyses," Microbiological Rev 60, 641-696 (1996); Givan, A. L., Flow Cytometry: First Principles, Second Edition, John Wiley and Sons (2001); Herzenberg, L. A., Parks, D., Sahaf, B., Perez, O., Roederer, M. and Herzenberg, L. A., "The history and future of the fluorescence activated cell sorter and flow cytometry: a view from Stanford," Clin Chem 48, 1819-1827 (2002); Jaroszeski, M. J. and Heller, R., Eds., Flow Cytometry Protocols (Methods in Molecular Biology, Volume 91), Humana Press (1997); Ormerod, M. G., Ed., Flow Cytometry: A Practical Approach, Third Edition, Oxford University Press (2000); Robinson, J. P., Ed., Current Protocols in Cytometry, John Wiley and Sons (1997); Shapiro, H. M., "Optical measurement in cytometry: light scattering, extinction, absorption and fluorescence," Meth Cell Biol 63, 107-129 (2001); Shapiro, H. M., Practical Flow Cytometry, Fourth Edition, Wiley-Liss (2003); Weaver, J. L., "Introduction to flow cytometry," Methods 21, 199-201 (2000).

Fluorescent compounds of the invention may also be used for fluorescence lifetime imaging (FLIM). FLIM is a useful technique for producing images based on the variation in the fluorescence decay characteristics of a fluorescent sample. It can be used as an imaging technique in confocal microscopy and other microscope systems. The lifetime of the fluorophore signal, rather than its intensity, is used to create the image in FLIM, which has the advantage of minimizing the effect of photon scattering in thick layers of sample. FLIM may be useful for biomedical tissue imaging, allowing to probe greater tissue depths than conventional fluorescence microscopy.

The compounds of the invention may be used in single molecule applications. Removal of ensemble averaging by observing individual molecules of fluorescent group may allow the determination of the mechanism of biological and chemical processes. Such processes may include the translocation of protein motors such as kinesin or myosin, formation, dissolution and translocation of cellular protein complexes and the mechanism of action of DNA or RNA polymerases. In such experiments, the present compounds may be used, for example, to label biomolecules which are attached to a surface such as a microscopy slide or flow chamber. Individual fluorophores may subsequently be observed using total internal reflection fluorescence microscopy.

The present compounds may also be used for the labeling of lipids. Lipids are involved in many biological processes, and the labeling of lipids and lipid rafts may is often a valuable method for studying their properties. Various lipid monolayers and bilayers may be labeled in live cells or artificial systems such as liposomes and micelles. For example, a live cell population may be labeled with a fluorescent conjugate prepared by reacting a compound of the invention and cholera toxin subunit B, which specifically interacts with lipid rafts. Such lipid rafts may then be crosslinked into distinct membrane patches by the use of an anti-cholera toxin antibody, which may be labeled with one of the present compounds.

The labeled polypeptides of the present invention find use as biosensors in prokaryotic and eukaryotic cells, e.g. as calcium ion indicators, as pH indicators, as phorphorylation indicators, as indicators of other ions including without limiting to magnesium, sodium, potassium, chloride and halides. For example, for detection of calcium ion, proteins containing an EF-hand motif are known to translocate from the cytosol to membranes upon binding to calcium ion. These proteins contain a myristoyl group that is buried within the molecule by hydrophobic interactions with other regions of the protein. Binding of calcium ion induces a conformational change exposing the myristoyl group which then is available for the insertion into the lipid bilayer. Labeling such an EF-hand containing protein with a subject fluorescent dye makes it an indicator of intracellular calcium ion concentration by monitoring the translocation from the cytosol to the plasma membrane. Such monitoring can be performed with the use of an optical detector, e.g., a confocal microscope. EF-hand proteins suitable for use in this system include, but are not limited to: recoverin (1-3), calcineurin B, troponin C, visinin, neurocalcin, calmodulin, parvalbumin, and the like.

For use as a pH indicator, a system based on hisactophilins may be employed. Hisactophilins are myristoylated histidine-rich proteins known to exist in Dictyostelium. Their binding to actin and acidic lipids is sharply pH-dependent within the range of cytoplasmic pH variations. In living cells membrane binding seems to override the interaction of hisactophilins with actin filaments. At pH of approximately 6.5 they typically locate to the plasma membrane and nucleus. In contrast, at pH 7.5 they evenly distribute throughout the cytoplasmic space. This change of distribution is reversible and is attributed to histidine clusters exposed in loops on the surface of the molecule. The reversion of intracellular distribution in the range of cytoplasmic pH variations is in accord with a pK of 6.5 of histidine residues. The cellular distribution is independent of myristoylation of the protein. By conjugating the subject fluorescent dye to hisactophilin, the intracellular distribution of the labeled hisactophilin can be followed by laser scanning, confocal microscopy or standard fluorescence microscopy. Quantitative fluorescence analysis can be done by performing line scans through cells (laser scanning confocal microscopy) or other electronic data analysis (e.g., using metamorph software (Universal Imaging Corp) and averaging of data collected in a population of cells.

The subject fluorescent proteins also find use in applications involving the automated screening of arrays of cells by using microscopic imaging and electronic analysis. Screening can be used for drug discovery and in the field of functional genomics: e.g., where the subject proteins are used as markers of whole cells to detect changes in multicellular reorganization and migration, e.g., formation of multicellular tubules (blood vessel formation) by endothelial cells, migration of cells through Fluoroblok Insert System (Becton Dickinson Co.), wound healing, neurite outgrowth; where the proteins are used as markers fused to peptides (e.g., targeting sequences) and proteins that allow the detection of change of intracellular location as indicator for cellular activity, for example: signal transduction, such as kinase and transcription factor translocation upon stimuli, such as protein kinase C, protein kinase A, transcription factor NFkB, and NFAT; cell cycle proteins, such as cyclin A, cyclin B 1 and cyclinE; protease cleavage with subsequent movement of cleaved substrate, phospholipids, with markers for intracellular structures such as endoplasmic reticulum, Golgi apparatus, mitochondria, peroxisomes, nucleus, nucleoli, plasma membrane, histones, endosomes, lysosomes, microtubules, actin.

The subject fluorescent proteins also find use in high through-put screening assays. The subject fluorescent proteins are typically more stable than proteins lacking the subject fluorescent dyes. In some aspects, the fluorescent proteins can exhibit a serum half-life of more than 1 hour, 2 hours, 5 hours, or 24 hours or more.

The subject fluorescent proteins can be used as second messenger detectors, e.g., by conjugating the subject fluorescent dyes to specific signaling domains, e.g., calcium binding SH2-, SH3-, PH-, PDZ-domain and etc.

The examples below are for the purpose of illustrating the practice of the invention. They shall not be construed as being a limitation on the scope of the invention or claims.

EXAMPLES

Example 1

Preparation of 1-(5-ethoxycarbonylpentyl)-imidazole-2-carboxaldehyde (Compound No. 31)

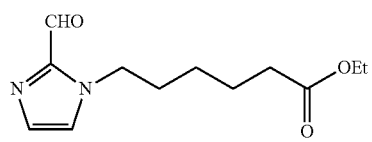

Compound No. 31

A mixture of imidazole-2-carboxaldehyde (Ig), potassium carbonate (6 g) and 6-bromohexanoic acid ethyl ester (1.84 mL) was stirred at 70° C. for 12 hours. The mixture was cooled to room temperature and then partitioned between water (100 mL) and ether (150 mL). The ether layer was washed with water twice (2×100 mL) and saturated NaCl (150 mL), followed by drying over anhydrous Na2SO4. The solvent was removed by rotary evaporation to give the product, which was used in the subsequent synthesis without further purification.

Example 2

Preparation of Compound No. 32

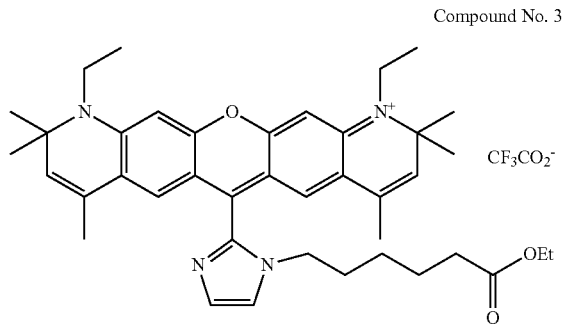

Compound No. 32

To a mixture of 7-hydroxy-1-ethyl-2,2,4-trimethyl-1,2-dihydroquinoline (Ig, 4.6 mmol) (U.S. Pat. No. 5,750,409) and compound No. 31 (0.48 g, 2 mmol) in CH$_2$Cl$_2$ was added trifluoroacetic acid (0.15 mL). The mixture was stirred at room temperature overnight and then concentrated to dryness in vacuo. The residue was dissolved in CHCl$_3$ (5 mL) and MeOH (5 mL). p-Chloranil (0.5 g, 2 mmol) and molecule sieve (2 g) were added to the above solution. The mixture was stirred at room temperature for 3 days. The solution was concentrated to dryness in vacuo and the residue was purified by column chromatography on silica gel to give a blue solid (80 mg).

Example 3

Preparation of Compound No. 33

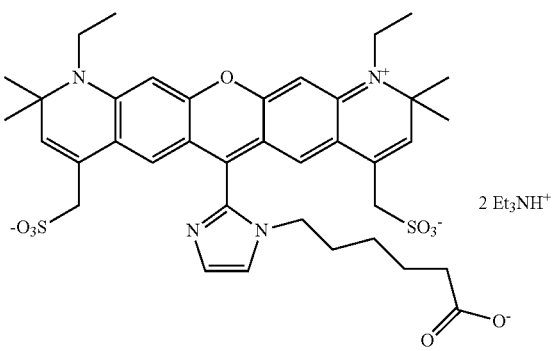

Compound No 33

To concentrated H$_2$SO$_4$ (2 mL) with 30% fuming H$_2$SO$_4$ (0.1 mL) at 0° C. was added compound No. 32 (80 mg, 0.11 mmol) in one portion. The mixture was stirred at 0° C. for 2 hrs and then at room temperature for 2 days. The mixture was added dropwise to a vigorously stirred Et$_2$O (30 mL) at 0° C. The precipitate was collected by centrifuge and the solid was purified by preparative HPLC to give a blue solid (40 mg).

Example 4

Preparation of Compound No. 5

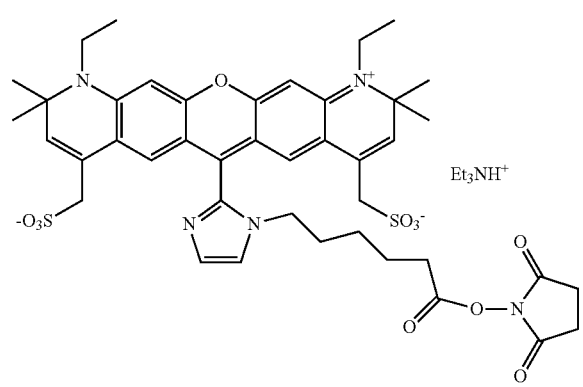

Compound No. 5

To a solution of compound No. 33 (40 mg, 0.046 mmol) in DMF (1 mL) was added Et$_3$N (20 μL) and TSTU (14 mg, 0.046 mmol). The mixture was stirred at room temperature for 30 minutes and concentrated to dryness in vacuo to give a blue solid, which was used for labeling without further purification.

Example 5

Preparation of Compound No. 34

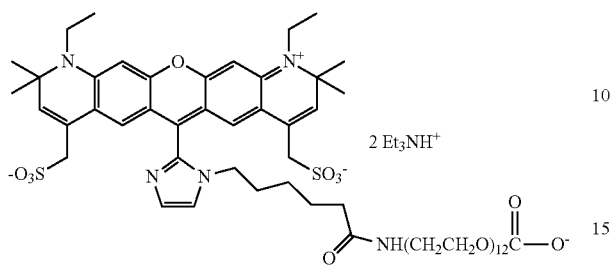

Compound No. 34

To a solution of compound No. 5 (10 mg, 0.01 mmol) in DMF (0.5 mL) was added Et$_3$N (5 µL) and amino-dPEG$_{12}$-acid (10 mg, 0.016 mmol)(Quanta Biodesign, cat #10287). The mixture was stirred at room temperature for 1 hr and then concentrated to dryness in vacuo. The residue was purified by LH-20 column to give a blue solid (12 mg).

Example 6

Preparation of Compound No. 6

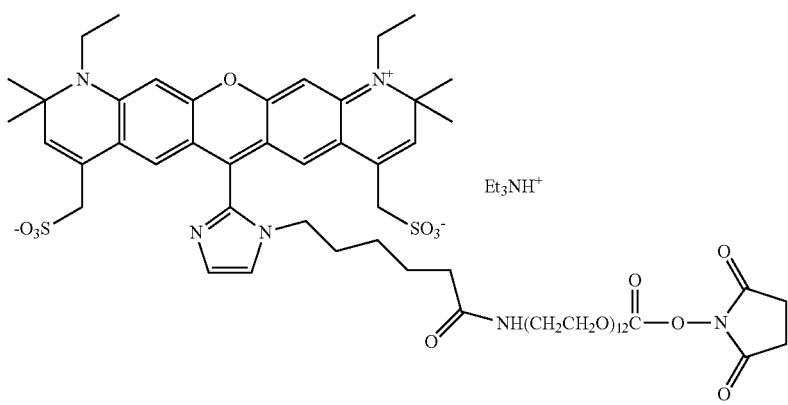

Compound No 6

To a solution of Compound No. 34 (2.3 mg, 0.001 mmol) in DMF (0.4 mL) was added Et$_3$N (1 µL) and TSTU (0.47 mg, 0.001 mmol). The mixture was stirred at room temperature for 30 minutes and then concentrated to dryness in vacuo. The residue was used for protein labeling without further purification.

Example 7

Preparation of Compound No. 35

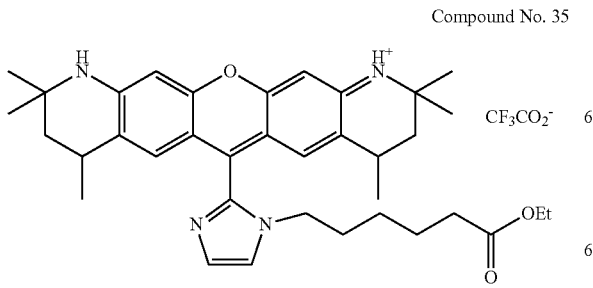

Compound No. 35

To a mixture of 7-hydroxy-2,2,4-trimethyl-1,2,3,4-tetrahydroquinoline (1.85 g, 9.7 mmol) and compound No. 31 (lg, 4.2 mmol) in CH$_2$Cl$_2$ was added trifluoroacetic acid (0.32 mL). The mixture was stirred at room temperature overnight and then concentrated to dryness in vacuo. The residue was dissolved in CHCl$_3$ (10 mL) and MeOH (10 mL), followed by the addition of p-chloranil (1.1 g, 4.2 mmol) and molecule sieve (4 g). The mixture was stirred at room temperature for 3 days. The solution was concentrated to dryness in vacuo and the residue was purified by column chromatography on silica gel to give a dark red solid.

Example 8

Preparation of Compound No. 36

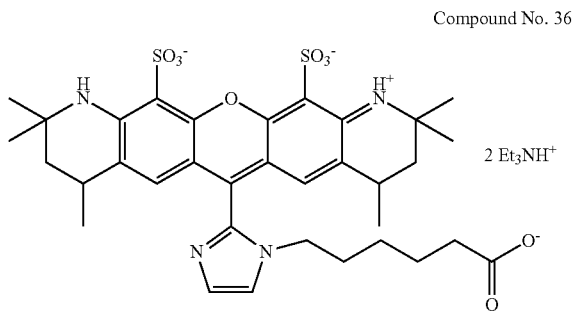

Compound No. 36

To 30% fuming H$_2$SO$_4$ (1 mL) at 0° C. was added Compound 35 (30 mg, 0.043 mmol). The mixture was kept stirring at 0° C. for 24 hrs and added dropwise to a vigorously stirred Et$_2$O (20 mL) at 0° C. The precipitate was collected by centrifuge and then purified by preparative HPLC to give a dark red solid.

Example 9

Preparation of Compound No. 2

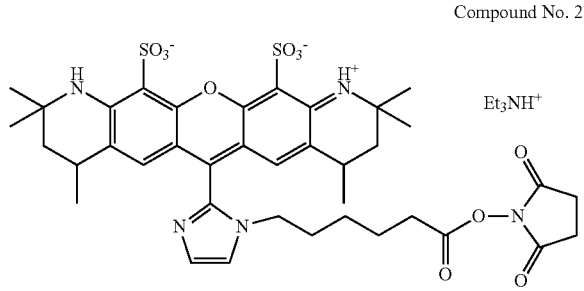

Compound No. 2

To solution of Compound No. 36 (3 mg, 0.004 mmol) in DMF (0.5 mL) was added Et$_3$N (3 μL) and TSTU (1.3 mg, 0.004 mmol). The mixture was stirred at room temperature for 15 minutes and then concentrated to dryness in vacuo. The residue was used for protein labeling without further purification.

Example 10

Preparation of Compound Nos. 21 and 22

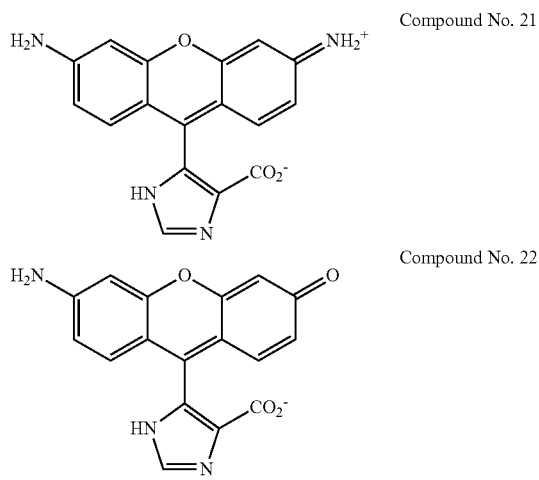

Compound No. 21

Compound No. 22

A mixture of 3-(ethoxycarbonylamino)phenol (6.58 g) and imidazole-4,5-dicarboxylic acid (½ equivalent) in 20 mL methanesulfonic acid was stirred at room temperature for 24 hours to obtain a homogeneous solution. About 2.5 g P$_2$O$_5$ was added and the mixture was continued to stir at 50° C. for 12 hours. The reaction mixture was poured over ice. The solid was collected by suction filtration and then dried under vacuum. The solid was suspended in 48% HBr (60 mL) and stirred at 110° C. for 5 hours. The mixture was cooled to room temperature and then poured into ice water. The solid was collected and dried under vacuum. The products were separated by HPLC using C18 reverse phase column and triethylammonium acetate buffer.

Example 11

Preparation of Compound No. 24

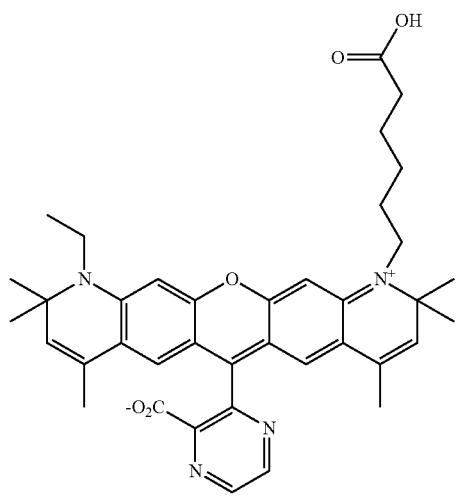

Compound No. 24

A mixture of 1-ethyl-7-hydroxy-2,2,4-trimethyl-1,2-dihydroquinoline (1.15 mmole), 1-(5-carboxypentyl)-7-hydroxy-2,2,4-trimethyl-1,2-dihydroquinoline (1.15 mmole), 2,3-pyrazinedicarboxylic anhydride (1.15 mmole) and 50 mg p-toluenesulfonic acid is stirred in propionic acid (80 mL) at 140° C. for 24 hours. The solvent is removed under vacuum and the product is purified by a silica gel column eluting with MeOH/CHCl$_3$.

Example 12

Preparation of Protein Dye-conjugates

Fluorescent conjugates of goat anti-mouse IgG (GAM), goat anti-rabbit IgG (GAR), and streptavidin were prepared from the respective proteins and a reactive dye, following published procedures (U.S. Pat. No. 6,974,873; Haugland et al., *Meth. Mol. Biol.* 45, 205(1995); Haugland et al., *Meth. Mol. Biol.* 45, 223(1995); Haugland et al., *Meth. Mol. Biol.* 45, 235(1995); Haugland et al., *Current Protocols in Cell Biology*, 16.5.1-16.5.22 (2000)). Briefly, an antibody or streptavidin at 1 mg/mL in 0.1 mM pH 8.5 sodium bicarbonate buffer was mixed with one of the reactive dye at various ratio of dye molecules/protein molecule. After incubating for about an hour at room temperature, the reaction mixture was separated by gel filtration using Sephadex G-25 equilibrated with PBS (pH 7.4). The various dye molecules/protein ratios used in the labeling reactions produced protein conjugates with different degree of dye labeling (DOL) as listed in Table 3 below for each dye/protein pair.

TABLE 3

List of selected antibody and streptavidin conjugates prepared using dyes of the invention and commercial dyes.

| Protein | Dye | Degree of Labeling (DOL) |
| --- | --- | --- |
| Streptavidin | Compound No. 5 | 2.5; 3.8; 4.6; 7.8 |
| Goat anti-mouse IgG | Compound No. 2 | 2.2; 4.2; 5.8; 7.5 |
| Goat anti-mouse IgG | Compound No. 6 | 2.28; 3.03; 4.01; 4.36 |
| Goat anti-mouse IgG | Alexa Fluor 633 | 0.95; 1.58; 2.11; 2.34 |
| Goat anti-mouse IgG | Compound No. 29 | 1.61; 2.85; 4.14; 5.33 |
| Goat anti-mouse IgG | Compound No. 30 | 1.79; 2.95; 4.81; 5.61; 6.47 |
| Goat anti-mouse IgG | Alexa Fluor 680 | 1.6; 2.7; 3.5; 4.9 |
| Goat anti-mouse IgG | Cy5.5 | 1.8; 2.6; 3.9; 7.6 |
| Goat anti-mouse IgG | Compound No. 75 | 2.0; 3.2; 4.3; 5.6 |

The fluorescence of the conjugates was measured using a Hitachi fluorescence spectrophotometer and was then plotted against the DOL.

Example 13

Preparation of a Phalloidin Dye-conjugate

To aminophalloidin (1 mg) and compound No. 6 (1.5 equivalents) in DMF (200 μL) was added N,N-diisopropylethylamine (3 equivalents) and the mixture was stirred at room temperature overnight. The solution was concentrated to dryness under vacuum and the residue was purified by column chromatography by LH-20 column (1.5 mg). The product is an effective stain for F-actin filaments in fixed-cell preparations.

Example 14

Preparation and Use of a Fluorescent α-bungarotoxin Dye-conjugate

To a solution of α-bungarotoxin (1 mg) in 0.1 M sodium bicarbonate (25 μL) was added compound No. 5 (1.5 equivalents) in one portion and the mixture was stirred at room temperature for 2 hours. The product was purified by G-25 size exclusion column and then by reverse-phase HPLC. Staining of acetylcholine receptors and detection of their resulting fluorescence, although detected at longer wavelength, was comparable to that obtained with Texas Red α-bungarotoxin conjugate.

Example 15

Preparation of Aminodextran-dye Conjugate

To a solution of 70000 MW aminodextran with an average of 13 amino groups in 0.1M sodium bicarbonate (400 µL) is added compound No. 2 so as to give a dye/dextran ratio of about 12. After 6 hours the conjugate is purified on SEPHADEX G-50 with water as eluent. Typically 4-6 moles of dye are conjugated to 70000 MW dextran.

Example 16

Preparation of Dye-bacteria Conjugates

Heat killed *Escherichia coli* are suspended in pH 8-9 buffer (10 mg/mL) and then incubated with 0.5-1.0 mg/mL of an amine-reactive dye such as compound No. 2. After 30-60 minutes the labeled bacteria are centrifuged and washed several times with buffer to remove any free dye. The labeled bacteria is analyzed by flow cytometry.

Example 17

Preparation of Nucleotide-dye Conjugates

To a solution of 5-(3-aminoallyl)-2-deoxyuridine 5'-triphosphate (2 mg, Sigma Chemical) in $H_2O$ (100 µL) is added compound No. 2 or compound No. 23 in DMF and triethylamine (5 µL). The mixture is stirred at room temperature for 3 hours and then concentrated to dryness in vacuo. The residue is purified by preparative HPLC. The product fractions are lyophilized to give a dark blue nucleotide conjugate.

Additionally, 2'-(or 3')-2-aminoethylaminocarbonyladenosine 5'-triphosphate is reacted with slight excess of compound No. 2 and following the precipitation with ethanol, the ribose-modified product is purified by preparative HPLC. Additional nucleotides conjugates with the dyes of invention can readily prepared by someone skilled in the art following the published procedures such as Nimmakayalu M. et al., *Biotechniques*, 2000, 28, 518; Muhlegger K. et al., *Biol. Chem.* Hoppe Seyler, 1990, 371, 953; Giaid A. et al. *Histochemistry*, 1989, 93, 191.

Example 18

Preparation of an Oligonucleotide Dye-conjugate

To a 5'-amine-modified, 18-base M13 primer sequence (100 µg) in $H_2O$ (4 µL) is added a solution of compound No. 10 (500 µg) in 0.1M sodium borate pH=8.5 buffer (200 µL). The mixture is stirred at room temperature overnight and 3 volumes of cold ethanol are added. The mixture is cooled to −20° C., centrifuged, the supernatant is decanted, the pellet is rinsed with ethanol and then dissolved in $H_2O$ (100 µL). The labeled oligonucleotide is purified by preparative HPLC. The desired peak is collected and evaporated to give the fluorescent oligonucleotide.

Example 19

Flow Cytometry Analysis of Cells Intracellularly Stained with Dye-antibody Conjugates One million Jurkat cells were fixed, permeabilized and stained with IgG1 isotype or intracellular mouse anti-human CD3 primary antibody (0.375 ug) followed by 1 ug of goat-anti-mouse conjugated to AlexaFluor633 or Compound No. 6. Fluorescence was detected on a BD FACS Calibur flow cytometer using the FL4 channel. The results are shown in FIG. 2, where the bars represent the fluorescence geometric means of the populations stained with isotype control (black bars) or CD3 (white bars) antibody. The data are also plotted as signal-to-noise ratio (i.e., relative fluorescence geometric means of the CD3 stained cell population over the respective isotype controls) vs. DOL in FIG. 3.

Example 20

Labeling β-galactosidase with a Thiol Reactive Dye

A solution of β-galactosidase, a protein rich in free thiol groups, is prepared in PBS buffer (1 mg in 200 µL) and then treated with a solution of thiol reactive compound No. 2 (5 mg) in DMF (100 µL). Unreactive dye is removed by centrifugation using Nanosep centrifugal device. The degree of substitution by the dye is estimated using the method cited in Example 2.

Example 21

Photostability Comparison Among Compound No. 6, Alexa Fluor 633, Dylight 633, Alexa 647 and DvLight649

Jurkat cells were fixed and stained with intracellular mouse anti-human CD3 primary antibody (0.375 ug) followed by 1 ug of goat-anti-mouse IgG conjugated to AlexaFluor633 (DOL 2.3), compound No. 6 (DOL 2.3), DyLight649 (DOL~6), or Alexa Fluor 647 (DOL~6). The DOL for each conjugate was the optimal value for each dye. Images were taken on an Olympus mercury arc lamp microscope using a Cy5 filter set. The relative fluorescence vs. time for each sample was plotted (FIG. 5). Traditionally, sulfonated cyanine dyes, such as Alexa Fluor 647 and DyLight 647, have been used for the 633 nm excitation by the HeNe laser with red emission. More recently, rhodamine-based Alexa Fluor 633 dye has become commercially available. As shown in the figure, cyanine-based dyes (i.e., Alexa Fluor 647, Dylight 633 and DyLight 649) have poor photostability, being essentially totally bleached in about 1 minute. On the other hand, the rhodamine-based Alexa Fluor 633 and compound No. 6 of the invention are very photostable. However, compound No. 6 of the invention is superior to Alexa Fluor 633 because of its significantly brighter fluorescence on protein (See FIG. 4 and Example 22).

Example 22

Comparison of Compound No. 6 and Alexa Fluor 633 by Microscopy

Jurkat cells were fixed and stained with intracellular mouse anti-human CD3 primary antibody (0.375 ug) followed by 1 ug of goat-anti-mouse conjugated to AlexaFluor633 (DOL 2.3) or compound No. 6 (DOL 2.3). Images were taken on an Olympus mercury arc lamp microscope using a Cy5 filter set at the same exposure conditions. The compound No. 6 staining is bright than that of AlexaFluor633 as assessed by microscopic analysis.

Example 23

Measurement of Absorption and Emission Spectra of Free Dyes or Dye-protein Conjugates The absorption spectra of free dyes or dye-antibody conjugates were measured on Beckman Coulter DU800 in pH 7.4 PBS. The concentrations of the dyes or conjugates were adjusted so that the maximal absorbance was around 1.0. The fluorescence emission spectra of the free dyes and conjugates were measured on a Hitachi F4500.

Example 24

Preparation of Compound No. 37

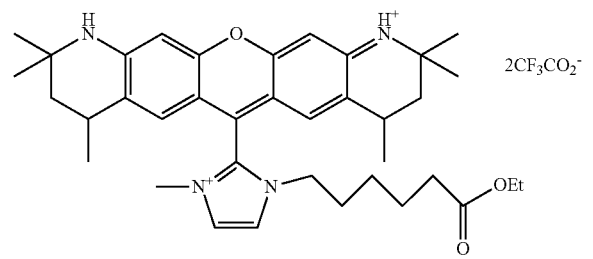

Compound No. 37

A mixture of compound No. 35 (100 mg, 0.17 mmol) and methyl p-toluenesulfonate (300 mg, 1.61 mmol) was heated at 60° C. for 1 hr. After cooling down to room temperature, EtOAc (5 mL) was added and the suspension was stirred at room temperature for 2 hrs. The precipitate (90 mg) was collected by centrifugation and dried to a constant weight.

Example 25

Preparation of Compound No. 38

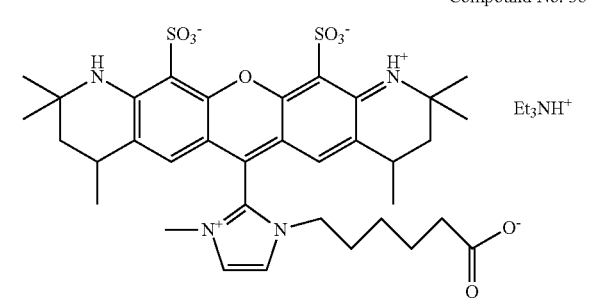

Compound No. 38

To 30% fuming $H_2SO_4$ (1 mL) at 0° C. was added Compound No. 37 (70 mg, 0.09 mmol). The mixture was stirred at 0° C. for 24 hrs and then added dropwise to a vigorously stirred $Et_2O$ (20 mL) at 0° C. The precipitate was collected by centrifugation and then purified by preparative HPLC to give a blue solid (10 mg).

Example 26

Preparation of Compound No. 29

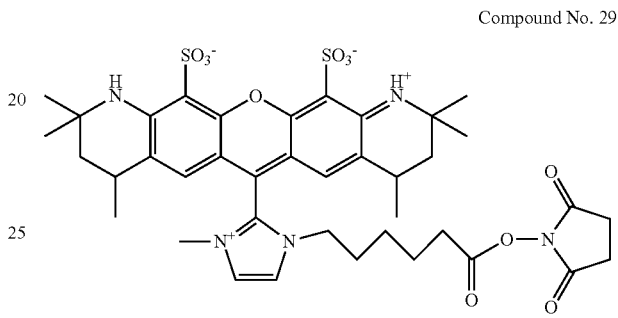

Compound No. 29

To a solution of Compound No. 38 (5 mg, 0.006 mmol) in DMF (0.5 mL) was added $Et_3N$ (3 μL) and TSTU (1.8 mg, 0.006 mmol). The mixture was stirred at room temperature for 15 minutes and then concentrated to dryness in vacuo. The residue was used for protein labeling without further purification.

Example 27

Preparation of Compound No. 39

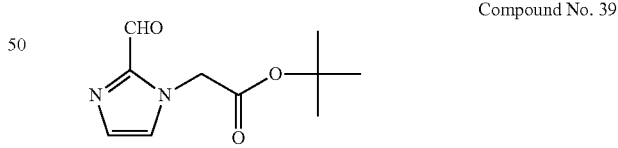

Compound No. 39

A mixture of imidazole-2-carboxaldehyde (1g), t-butyl bromoacetate (1 equivalent) and potassium carbonate (1.5 equivalent) in 30 mL DMF was stirred at room temperature for 24 hours. The mixture was poured into water (50 mL) and then extracted with EtOAc two times (2×60 mL). The combined organic layer was washed with water and then brine, followed by drying over anhydrous Na2SO4. Evaporation of the solvent gave the product, which was used in the next step without further purification.

Example 28

Preparation of Compound No. 40

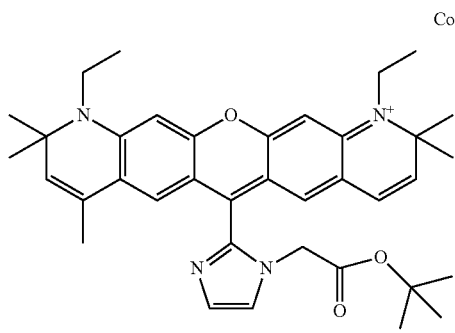

Compound No. 40

To a mixture of 7-hydroxy-1-ethyl-2,2,4-trimethyl-1,2-dihydroquinoline (1g, 4.6 mmol) and compound No. 39 (0.46 g, 2.1 mmol) in $CH_2Cl_2$ was added trifluoroacetic acid (0.15 mL). The mixture was stirred at room temperature overnight and then concentrated to dryness in vacuo. The residue was dissolved in $CHCl_3$ (5 mL) and MeOH (5 mL). To the resulting solution were added p-chloranil (0.5 g, 2 mmol) and molecule sieve (2 g). The mixture was stirred at room temperature for 3 days. The solution was concentrated to dryness in vacuo and the residue was purified by column chromatography on silica gel to give a blue solid (120 mg).

Example 29

Preparation of Compound No. 41

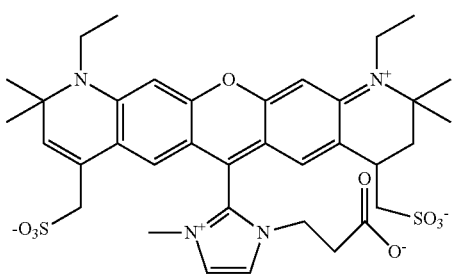

Compound No. 41

To concentrated $H_2SO_4$ (2 mL) with 30% fuming $H_2SO_4$ (0.1 mL) at 0° C. was added compound No. 40 (90 mg, 0.12 mmol) in one portion. The mixture was stirred at 0° C. for 2 hrs and then at room temperature for 2 days. The mixture was added dropwise to a vigorously stirred $Et_2O$ (30 mL) at 0° C. The precipitate was collected by centrifugation and the solid was purified by preparative HPLC to give a blue solid (47 mg).

Example 30

Preparation of Compound No. 42

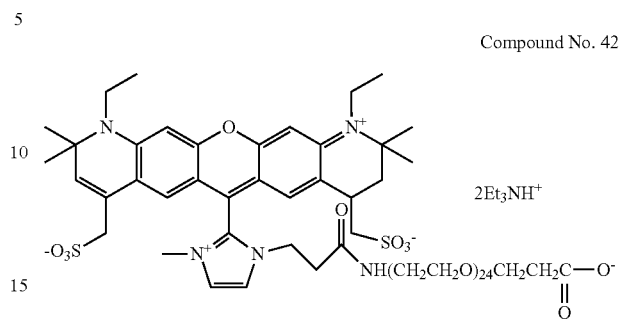

Compound No. 42

To a solution of compound No. 41 (4 mg, 0.005 mmol) in DMF (0.2 mL) was added $Et_3N$ (2.3 µL) and amino-dPEG$_{24}$-acid (6.3 mg, 0.005 mmol)(Quanta Biodesign, cat #10317). The mixture was stirred at room temperature for 1 hr and then concentrated to dryness in vacuo. The residue was purified by LH-20 column to give a blue solid (5 mg).

Example 31

Preparation of Compound No. 30

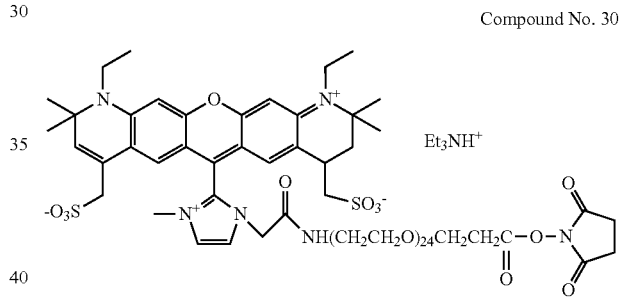

Compound No. 30

To a solution of Compound No. 42 (2 mg, 0.001 mmol) in DMF (0.25 mL) was added $Et_3N$ (0.45 µL) and TSTU (0.33 mg, 0.001 mmol). The mixture was stirred at room temperature for 30 minutes and then concentrated to dryness in vacuo. The residue was used for protein labeling without further purification.

Example 32

Preparation of Compound No. 16

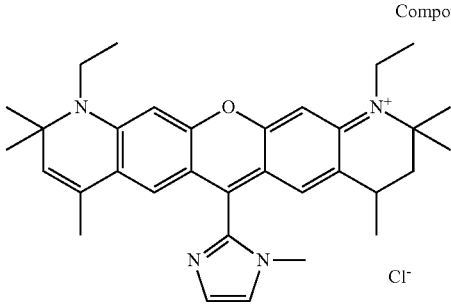

Compound No. 16

To a mixture of 7-hydroxy-1-ethyl-2,2,4-trimethyl-1,2-dihydroquinoline (2 g, 9.2 mmol) and 1-methyl-2-imidazocarboxaldehyde (0.5 g, 4.5 mmol) in $CH_2Cl_2$ (20 mL) was added trifluoroacetic acid (0.34 mL). The mixture was stirred at room temperature overnight and then concentrated to dryness in vacuo. The residue was dissolved in $CHCl_3$ (10 mL) and MeOH (10 mL). To this solution were then added p-chloranil (1.1 g, 4.5 mmol) and molecular sieve (4 g). The mixture was stirred at room temperature for 3 days. The solution was concentrated to dryness in vacuo and the residue was purified by column chromatography on silica gel to give a blue solid. The solid was redissolved in DMF (5 mL) and then poured into saturated sodium chloride. The solid was collected by centrifugation (50 mg). Compound No. 16 is a mitochondrion-staining dye, which stains mitochondria in a membrane potential-dependent fashion.

Example 33

Preparation of Compound No. 70

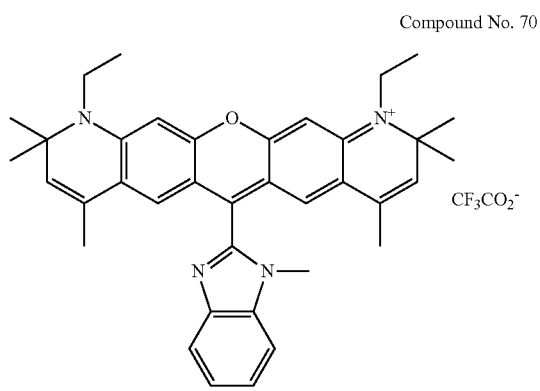

Compound No. 70

Compound No. 70 (35 mg), which is a mitochondrial dye, was prepared according to the synthesis of compound No. 16 from 7-hydroxy-1-ethyl-2,2,4-trimethyl-1,2-dihydroquinoline (1.42 g, 6.5 mmol) and 1-methyl-2-benzimidazocarboxaldehyde (0.5 g, 3.12 mmol).

Example 34

Preparation of Compound No. 74

Compound No. 16 (100 mg) was quarternized with methyl p-toluenesulfonate using the procedure of Example 24. The reaction mixture was redissolved in DMF (2 mL), and the resulting solution was poured into saturated sodium chloride. The precipitate was collected by centrifugation to give compound No. 74, which is a mitochondrial dye.

Example 35

Mitochondrial Staining Using Compound Nos. 16 and 74

HeLa cells were cultured for 2 days at 37° C., 5% CO2. Live cells were stained with 200 nM compound No. 16 or 10 uM compound No. 74 in DMEM media for 30 minutes at 37° C., 5% CO2. Cells were washed in fresh medium and cells were viewed on a mercury arc lamp microscope using a Cy5 filter set. Images were taken using a CCD camera and Image Pro Express software. Localization of dyes are concentrated in the mitochondria as depicted by punctuate staining.

Example 36

Mitochondrial Staining as a Function of Membrane Potential

Live Jurkat cells were stained with 50 nM Compound No. 16 with and without 50 uM carbonyl cyanide m-chlorophenyl hydrozone (CCCP) for 30 minutes prior to analysis by flow cytometry on the FL4 channel of a BD FACS Calibur. Treatment with CCCP disrupts the mitochondrial membrane potential. The graph depicts the relative geometric mean fluorescence of the stained population treated without (Control) or with 50 uM CCCP. The dye is sensitive to disruption of the mitochondrial membrane potential as exhibited by the lower fluorescence intensity of the CCCP treated population of cells. The membrane potential-dependent mitochondrial staining by compound No. 16 makes the dye useful for assessing the health of cells as only healthy cells have functional mitochondria and have normal membrane potential. For example, cells undergoing apoptosis are known to lose membrane potential.

Example 37

Preparation of Compound No. 89

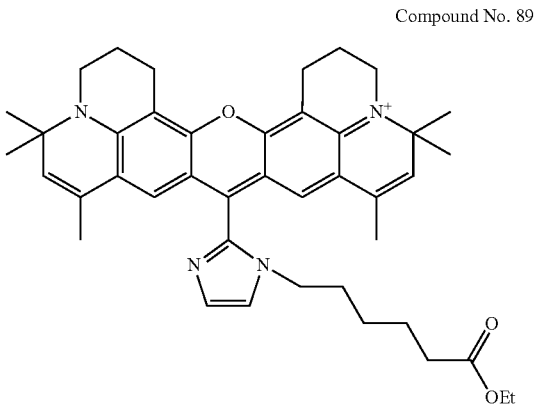 [SMILES: CCOC(=O)CCCCCn1ccnc1C1=c2cc3c4c(c2Oc2c1cc1c5c2CCCN5C(C)(C)C=C1C)CCC[N+]=4C(C)(C)C=C3C]

Compound No. 89

Compound No. 89 was prepared according to the synthesis of compound No. 32 from the bicyclic aminophenol (U.S. Pat. No. 6,191,278, which is hereby incorporated by reference in its entirety) and compound No. 31.

Example 38

Preparation of Compound No. 90

Compound No. 90

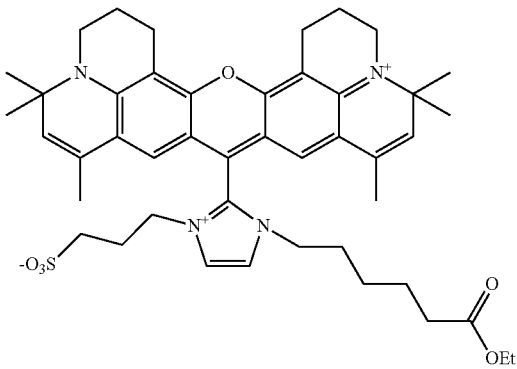

Compound No. 90 was prepared according to the synthesis of compound No. 37 by quarternizing Compound No. 89 with neat propanesultone.

Example 39

Preparation of Compound No. 91

Compound No. 91

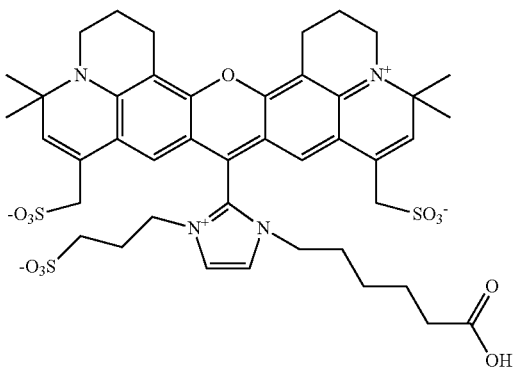

Compound No. 91 was prepared according to the synthesis of compound No. 33 from compound No. 90.

Example 40

Preparation of Compound No. 75

Compound No. 75

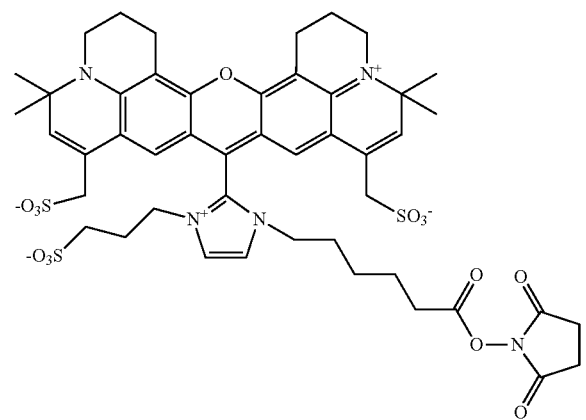

Compound No. 75 was prepared according to the synthesis of compound No. 5 from compound No. 91. This compound was conjugated to goat anti-mouse IgG antibody as described in Example 12.

Example 40

Photostability Comparison Among Compound No. 75, Alexa Fluor 680 and Cy5.5

Figure 12:
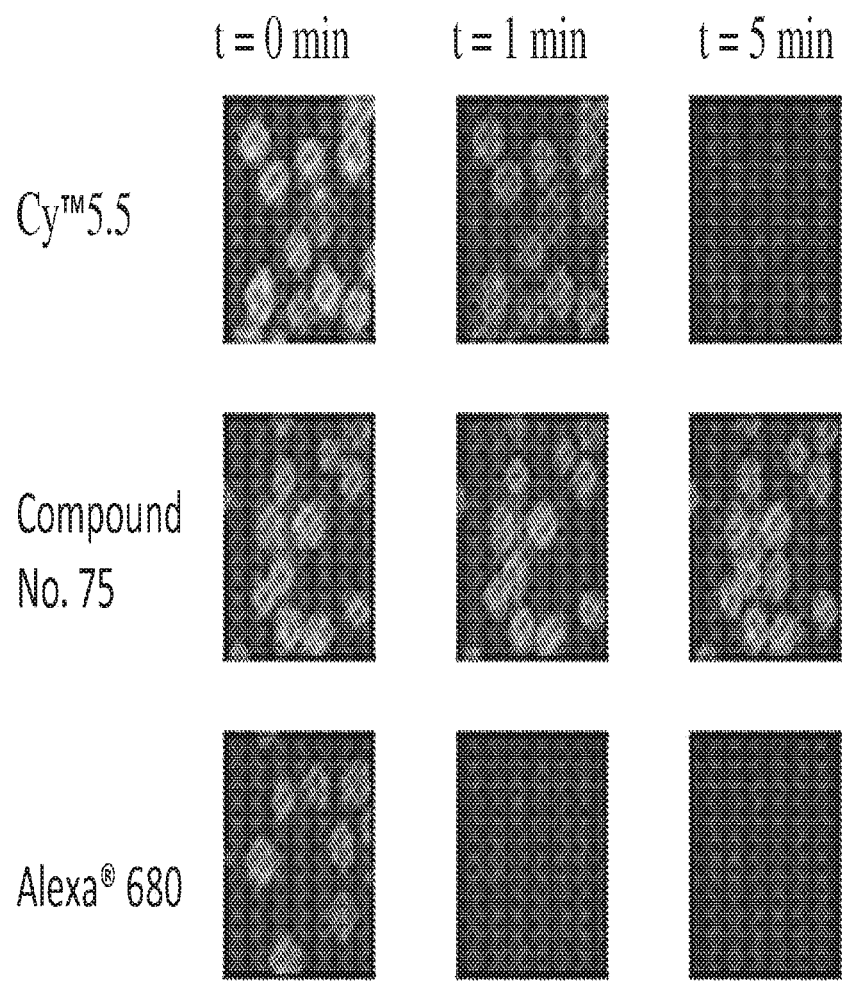
FIG. 12 shows microscopic images of Jurkat cells fixed and stained with intracellular mouse anti-human CD3 primary antibody followed by goat-anti-mouse conjugated to AlexaFluor680, Cy5.5 or compound No. 75. Images were taken at time 0.0, 1.0 and 5.0 min with continuous illumination using a Cy5 filter set.

Intracellular mouse anti-human CD3 primary antibody and three goat anti-mouse conjugates were prepared from Compound No. 75, Alexa Fluor 680 and Cy5.5, respectively, each with a DOL of ~4. The conjugates were used to stain fixed Jurkat cells as described in Example 21. Cell images were taken as in Example 21 using a Cy5 filter set at time 0.0, 1.0 and 5.0 minutes. The results of photobleaching experiments are shown in FIG. 12.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:
1. A compound of Formula 1a:

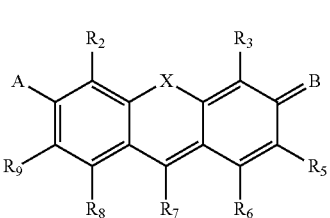

Formula 1a wherein:
X is O, S, or —C(CH$_3$)$_2$—;
A is —NR$_1$R$_{1a}$;
B is =N$^+$R$_4$R$_{4a}$;
C is —OR$_4$ or —NR$_4$R$_{4a}$;
R$_1$, R$_{1a}$, R$_4$, and R$_{4a}$ are each independently H or alkyl, unsubstituted or substituted with -L-SO$_3^-$, -L-PO$_3^{2-}$, a water-soluble polymer, or with -L-R$_x$; or one or more pair of R$_1$ and R$_{1a}$ or R$_4$ and R$_{4a}$ together with the nitrogen to which they are attached form a saturated or unsaturated ring optionally substituted by any of -L-SO$_3^-$, -L-PO$_3^{2-}$ and -L-R$_x$; or at least one of R$_1$, R$_{1a}$, R$_4$, or R$_{4a}$ is an enzyme substrate or a protecting group;
R$_7$ is a 5-membered monocyclic heteroaryl group, optionally substituted with one or more substituents selected independently from halogen, CO$_2^-$, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-PO$_3^{2-}$, L-SO$_3^-$, and -L-R$_x$;
R$_2$, R$_3$, R$_5$, R$_6$, R$_8$, R$_9$, are each independently H, halogen, CN, alkyl, alkenyl, alkoxy, aryl, heteroaryl, -L-PO$_3^{2-}$, -L-SO$_3^-$, or -L-R$_x$; or one or more pair of R$_2$ and R$_{1a}$, $R_3$ and $R_{4a}$, $R_4$ and $R_5$, $R_5$ and $R_6$, $R_8$ and $R_9$, or $R_9$ and $R_1$, together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-$PO_3^{2-}$, L-$SO_3^-$, or -L-$R_x$;

$R_x$ is a reactive group;

L is a bond or $(Q)_n$, each Q is independently $NR_d$, $S(O)_t$, O, C(=X), (C=X), substituted or unsubstituted alkyl, substituted or unsubstituted heteroalkyl, substituted or unsubstituted aryl, substituted or unsubstituted heteroaryl, substituted or unsubstituted cycloalkyl, or substituted or unsubstituted heterocycloalkyl, wherein t is 0-2, and no more than two $NR_d$ are adjacent and no two O are adjacent;

n is 1-20; and each $R_d$ is H, substituted or unsubstituted alkyl; wherein $R_7$ is substituted with -L-$R_x$ or at least one of $R_2$ and $R_3$ is -L-$SO_3^-$; and wherein at least one pair of $R_1$ and $R_9$ or $R_4$ and $R_5$ taken together with the atoms to which they are attached forms a fused saturated or unsaturated ring that is optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-$PO_3^{2-}$, L-$SO_3^-$, or -L-$R_x$.

2. The compound of claim 1, wherein X is O.

3. The compound of claim 1, wherein said fused saturated or unsaturated ring formed by $R_1$ and $R_9$ and/or $R_4$ and $R_5$ ring is substituted by -L-$PO_3^{2-}$ or -L-$SO_3^-$.

4. The compound of claim 1, wherein said fused saturated or unsaturated ring formed by $R_1$ and $R_9$ and/or $R_4$ and $R_5$ is substituted by at least one alkyl.

5. The compound of claim 1, wherein at least one of $R_2$ and $R_3$ is -L-$SO_3^-$.

6. The compound of claim 5, wherein at least one of $R_2$ and $R_3$ is —$SO_3^-$.

7. The compound of claim 1, wherein $R_7$ is pyrazolyl substituted with -L-$R_x$, and optionally further substituted with halogen, $CO_2^-$, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-$PO_3^{2-}$, L-$SO_3^-$, or -L-$R_x$.

8. The compound of claim 1, wherein $R_7$ is a pyrazolyl substituted with -L-$R_x$, and an aryl.

9. The compound of claim 8, wherein the aryl is substituted with one or more substituent selected from the group consisting of —OH, oxo, halo, alkoxy, dialkylamino, —$PO_3^{2-}$, —$SO_3^-$, —$CO_2^-$, a reactive group, and a heterocyclyl.

10. The compound of claim 8, wherein the aryl is substituted with a halo and a —$SO_3^-$.

11. The compound of claim 10, wherein $R_x$ is a carboxylic acid.

12. The compound of claim 1, wherein at least one or more pair of $R_2$ and $R_{1a}$, $R_3$ and $R_{4a}$, $R_4$ and $R_5$, $R_5$ and $R_6$, $R_8$ and $R_9$, or $R_9$ and $R_1$, together with the atoms to which they are attached form one or more fused saturated or unsaturated rings that are optionally substituted by at least one halogen, CN, alkyl, alkenyl, alkoxy, alkylthio, alkylamino, dialkylamino, alkylaminocarbonyl, dialkylaminocarbonyl, alkylaminosulfonyl, dialkylaminosulfonyl, aminosulfonyl, aryl, heteroaryl, -L-$PO_3^{2-}$, L-$SO_3^-$, or -L-$R_x$.

13. A kit comprising: i) a compound of claim 1; and ii) instructions instructing the use of the compound.

14. The kit of claim 13, wherein the kit additionally comprises a buffer and optionally materials or devices for purifying conjugation products.

15. A biomolecule comprising a label having a structure of a compound of claim 1, comprising at least one reactive moiety, wherein the at least one reactive moiety of the compound has undergone a reaction which attaches the label to the biomolecule.

16. The biomolecule of claim 15, wherein the biomolecule comprises a polynucleotide or a polypeptide.

17. An immunoglobin comprising a label having a structure of a compound of claim 1, comprising at least one reactive moiety, wherein at least one reactive moiety of the compound has undergone a reaction which attaches the label to the immunoglobin.

* * * * *

UNITED STATES PATENT AND TRADEMARK OFFICE
CERTIFICATE OF CORRECTION

PATENT NO. : 10,053,484 B2  
APPLICATION NO. : 15/375649  
DATED : August 21, 2018  
INVENTOR(S) : Fei Mao et al.

Page 1 of 1

It is certified that error appears in the above-identified patent and that said Letters Patent is hereby corrected as shown below:

On the Title Page

Attorney, Agent, or Firm, item (74), delete "Wison Sonsini Goodrich & Rosati" and insert -- Wilson Sonsini Goodrich & Rosati --.

Signed and Sealed this  
Fourth Day of June, 2019

Andrei Iancu  
*Director of the United States Patent and Trademark Office*